United States Patent
Liu et al.

(10) Patent No.: US 11,746,148 B2
(45) Date of Patent: Sep. 5, 2023

(54) ANTIBODY MOLECULES COMPRISING A SINGLE-DOMAIN ANTIGEN-BINDING SITE AND FAB FRAGMENTS

(71) Applicant: INNOVENT BIOLOGICS (SUZHOU) CO., LTD., Jiangsu (CN)

(72) Inventors: Junjian Liu, Jiangsu (CN); Xiaoniu Miao, Jiangsu (CN); Zhihui Kuang, Jiangsu (CN)

(73) Assignee: INNOVENT BIOLOGICS (SUZHOU) CO., LTD., Jiangsu (CN)

( * ) Notice: Subject to any disclaimer, the term of this patent is extended or adjusted under 35 U.S.C. 154(b) by 229 days.

(21) Appl. No.: 16/965,229

(22) PCT Filed: Mar. 26, 2019

(86) PCT No.: PCT/CN2019/079671
§ 371 (c)(1),
(2) Date: Jul. 27, 2020

(87) PCT Pub. No.: WO2019/184909
PCT Pub. Date: Oct. 3, 2019

(65) Prior Publication Data
US 2022/0041702 A1 Feb. 10, 2022

(30) Foreign Application Priority Data
Mar. 27, 2018 (CN) .......................... 201810259102.3
Mar. 15, 2019 (CN) .......................... 201910196438.4

(51) Int. Cl.
*C07K 16/28* (2006.01)
*C07K 16/24* (2006.01)
*C07K 16/22* (2006.01)

(52) U.S. Cl.
CPC .......... *C07K 16/22* (2013.01); *C07K 16/2827* (2013.01); *C07K 16/2878* (2013.01);
(Continued)

(58) Field of Classification Search
None
See application file for complete search history.

(56) References Cited

U.S. PATENT DOCUMENTS

| 6,277,375 B1 | 8/2001 | Ward |
| 6,689,607 B2 | 2/2004 | Ni et al. |

(Continued)

FOREIGN PATENT DOCUMENTS

| CN | 105143270 A1 | 9/2014 |
| CN | 104428315 A | 3/2015 |

(Continued)

OTHER PUBLICATIONS

Armour et al. "Recombinant human IgG molecules lacking Fcγ receptor I binding and monocyte triggering activities." European Journal of Immunology, 1999, 29(8): 2613-2624.

(Continued)

*Primary Examiner* — Claire Kaufman
(74) *Attorney, Agent, or Firm* — Leason Ellis LLP

(57) ABSTRACT

The present invention provides an artificially designed antibody molecule comprising four polypeptide chains, where each of the first polypeptide chain and the third polypeptide chain comprises an immunoglobulin light chain, and each of the second polypeptide chain and the fourth polypeptide chain comprises, from the N-terminus to the C-terminus, an immunoglobulin heavy chain variable region, an immunoglobulin CH1 domain, a VHH, an immunoglobulin CH2 domain, an immunoglobulin CH3 domain, and optionally an immunoglobulin CH4 domain.

The present invention also provides a polynucleotide encoding the antibody molecule, a vector comprising the polynucleotide, a host cell comprising the polynucleotide or the vector, an immunoconjugate and a pharmaceutical compo- (Continued)

Antibody Bi-2-51 sition comprising the antibody molecule, and use of the antibody molecule in the immunotherapy, prevention and/or diagnosis of diseases.

8 Claims, 13 Drawing Sheets

Specification includes a Sequence Listing.

(52) U.S. Cl.
CPC ...... *C07K 2317/22* (2013.01); *C07K 2317/24* (2013.01); *C07K 2317/31* (2013.01); *C07K 2317/53* (2013.01); *C07K 2317/55* (2013.01); *C07K 2317/565* (2013.01); *C07K 2317/569* (2013.01)

(56) References Cited

U.S. PATENT DOCUMENTS

| | | | |
|---|---|---|---|
| 7,025,962 B1 | 4/2006 | Gorman et al. | |
| 7,618,632 B2 | 11/2009 | Collins et al. | |
| 7,812,135 B2 | 10/2010 | Smith et al. | |
| 7,959,925 B2 | 6/2011 | Weinberg et al. | |
| 8,388,967 B2 | 3/2013 | Smith et al. | |
| 8,591,886 B2 | 11/2013 | Ponath et al. | |
| 8,709,424 B2 | 4/2014 | Schebye et al. | |
| 10,308,720 B2 * | 6/2019 | Timmer | C07K 16/2878 |
| 2014/0072566 A1 | 3/2014 | Kwon | |
| 2016/0145354 A1 * | 5/2016 | Bacac | C07K 16/2809 435/254.2 |
| 2019/0023793 A1 * | 1/2019 | Shen | A61K 47/6849 |
| 2019/0202935 A1 * | 7/2019 | Chou | C07K 16/24 |
| 2020/0140562 A1 * | 5/2020 | Tsun | A61K 47/6803 |

FOREIGN PATENT DOCUMENTS

| | | | | |
|---|---|---|---|---|
| CN | 104884473 A | 9/2015 | | |
| CN | 107686520 A | 2/2018 | | |
| CN | 107750164 A | 3/2018 | | |
| CN | 108623685 A | 10/2018 | | |
| EP | 1866339 B1 | 5/2013 | | |
| EP | 1947183 B1 | 7/2013 | | |
| EP | 2961773 B1 * | 3/2019 | ............. | A61P 35/00 |
| WO | 199734631 A1 | 9/1997 | | |
| WO | 199823289 A1 | 6/1998 | | |
| WO | 9920758 A1 | 4/1999 | | |
| WO | 9940196 A1 | 8/1999 | | |
| WO | 0103720 A2 | 1/2001 | | |
| WO | 2004060319 A2 | 7/2004 | | |
| WO | 2005007190 A1 | 1/2005 | | |
| WO | 2005055808 A2 | 6/2005 | | |
| WO | 2005115451 A2 | 12/2005 | | |
| WO | 2006083289 A2 | 8/2006 | | |
| WO | 2006121810 A2 | 11/2006 | | |
| WO | 2007005874 A2 | 1/2007 | | |
| WO | 2007/095338 A2 | 8/2007 | | |
| WO | 2007133822 A1 | 11/2007 | | |
| WO | 2010077634 A1 | 7/2010 | | |
| WO | 2011028683 A1 | 3/2011 | | |
| WO | 2011051726 A2 | 5/2011 | | |
| WO | 2012027328 A2 | 3/2012 | | |
| WO | 2012138475 A1 | 10/2012 | | |
| WO | 2013039954 A1 | 3/2013 | | |
| WO | 2014012479 A1 | 1/2014 | | |
| WO | 2015026684 A1 | 2/2015 | | |
| WO | 2016/065038 A1 | 4/2016 | | |
| WO | WO-2016200835 A1 * | 12/2016 | ......... | A61K 39/3955 |
| WO | 2017/123673 A2 | 7/2017 | | |
| WO | 2018/014855 A1 | 1/2018 | | |

OTHER PUBLICATIONS

Brinkmann et al., "The making of bispecific antibodies." MAbs. 2017, vol. 9. No. 2, 182-212.

Carter et al. "PD-1: PD-L inhibitory pathway affects both CD4+ and CD8+ T cells and is overcome by IL-2." European journal of immunology 2002, 32(3): 634-643.

Chelius et al. "Structural and functional characterization of the trifunctional antibody catumaxomab." MAbs 2010, vol. 2. No. 3. 309-319.

Coe et al. "Depletion of regulatory T cells by anti-GITR mAb as a novel mechanism for cancer immunotherapy" Cancer Immunology, Immunotherapy, 2010, 59(9): 1367-1377.

Cohen et al. "Agonist anti-GITR monoclonal antibody induces melanoma tumor immunity in mice by altering regulatory T cell stability and intra-tumor accumulation." PloS one 5.5 (2010): e10436.

Cuzzocrea et al. "Genetic and pharmacological inhibition of GITR-GITRL interaction reduces chronic lung injury induced by bleomycin instillation." The FASEB Journal, 2007, 21(1): 117-129.

DeNardo et al. "Comparison of 1,4,7,10-tetraazacyclododecane-N,N',N'',N'''-tetraacetic acid (DOTA)-peptide-ChL6, a novel immunoconjugate with catabolizable linker, to 2-iminothiolane-2-[p-(bromoacetamido)benzyl]-DOTA-ChL6 in breast cancer xenografts." Clinical cancer research, 1998, 4(10): 2483-90.

Estep et al. "High throughput solution-based measurement of antibody-antigen affinity and epitope binning." MAbs. 2013, vol. 5. No. 2, 270-278.

Gentz et al., "Bioassay for trans-activation using purified human immunodeficiency virus tat-encoded protein: trans-activation requires mRNA synthesis." Proceedings of the National Academy of Sciences, 1989, 86(3): 821-824.

Gramaglia et al. "Ox-40 ligand: a potent costimulatory molecule for sustaining primary CD4 T cell responses." The Journal of Immunology, 1998, 161(12): 6510-6517.

Gramaglia et al. "The OX40 costimulatory receptor determines the development of CD4 memory by regulating primary clonal expansion." The Journal of Immunology, 2000, 165(6): 3043-3050.

Iwai et al. "Involvement of PD-L1 on tumor cells in the escape from host immune system and tumor immunotherapy by PD-L1 blockade." Proceedings of the National Academy of Sciences, 2002, 99(19): 12293-12297.

Ridgway et al., "Knobs-into-holes' engineering of antibody CH3 domains for heavy chain heterodimerization." Protein Engineering, Design and Selection, 1996, 9(7): 617-621.

Latchman et al. "PD-L2 is a second ligand for PD-1 and inhibits T cell activation." Nature immunology, 2001, 2(3): 261-268.

Mallett et al., "Characterization of the MRC OX40 antigen of activated CD4 positive T lymphocytes—a molecule related to nerve growth factor receptor." The EMBO Journal, 1990, 9(4): 1063-1068.

Nocentini et al. "A new member of the tumor necrosis factor/nerve growth factor receptor family inhibits T cell receptor-induced apoptosis." Proceedings of the National Academy of Sciences, 1997, 94(12): 6216-6221.

Ohigashi et al. "Clinical significance of programmed death-1 ligand-1 and programmed death-1 ligand-2 expression in human esophageal cancer." Clinical Cancer Research, 2005, 11(8): 2947-2953.

Okazaki et al., "PD-1 and PD-1 ligands: from discovery to clinical application." International immunology, 2007, 19(7): 813-824.

Orcutt et al. "A modular IgG-scFv bispecific antibody topology." Protein Engineering, Design & Selection, 2010, 23(4): 221-228.

Paterson et al. "Antigens of activated rat T lymphocytes including a molecule of 50,000 Mr detected only on CD4 positive T blasts." Molecular Immunology, 1987, 24(12): 1281-1290.

Thompson et al. "Tumor B7-H1 is associated with poor prognosis in renal cell carcinoma patients with long-term follow-up." Cancer research, 2006, 66(7): 3381-3385.

Tone et al. "Mouse glucocorticoid-induced tumor necrosis factor receptor ligand is costimulatory for T cells." Proceedings of the National Academy of Sciences, 2003, 100(25): 15059-15064.

Yao et al., "Advances in targeting cell surface signalling molecules for immune modulation." Nature Reviews Drug Discovery, 2013, 12(2): 130-146.

Nagorsen et al., Immunomodulatory therapy of cancer with T cell-engaging BiTE antibody blinatumomab, Exp Cell Res., 317,1255-1260, 2011.

(56) References Cited

OTHER PUBLICATIONS

Padlan, Anatomy of the antibody molecule, Mol. Immun., 31: 169-217, 1994.
Atwell, et al., Stable heterodimers form remodeling the domain interface of a homodimer using a phage display library. J. Mol. Biol, 270: 26-35, 1997.
Paterson et al., Antigens of activated Rat T lymphocytes including a molecule of 50,000 M(r) detected only on CD4 positive T blasts, Molecular Immunology, 24(12): 1281-1290, 1987.
Senger et al., Tumor cells secrete a vascular permeability factor that promotes accumulation of ascites fluid, Science, 219 (4587): 983-985, 1983.
Lapeyre-Prost A, et al., Immunomodulatory Activity of VEGF in Cancer, Int Rev Cell Mol Biol., 330: 295-342, 2017.
Shimizu et al., Stimulation of CD25(+)CD4(+) regulatory T cells through GITR breaks immunological self-tolerance, Nature Immunology, 3: 135-142, 2002.
Yazaki et al., Expression of Recombinant Antibodies in Mammalian Cell Lines, Methods in Molecular Biology, vol. 248, 255-268; 2003.
Shen et al., Single variable domain-IgG fusion. A novel recombinant approach to Fc domain-containing bispecific antibodies, J Biol Chem., 2006; 281(16):10706-14.
International Search Report and Written Opinion in PCT/2019/079671 dated Jun. 25, 2019.

\* cited by examiner

Antibody Bi-110-112HC

Antibody Bi-113-112HC

Antibody Bi-119-112LC

Antibody Bi-122-112LC

Binding of anti-OX40/PD-L1 bispecific antibody to CHO cells overexpressing PD-L1

Binding of anti-OX40/PD-L1 bispecific antibody to CHO cells overexpressing OX40

ANTIBODY MOLECULES COMPRISING A SINGLE-DOMAIN ANTIGEN-BINDING SITE AND FAB FRAGMENTS

FIELD OF THE INVENTION

The present invention generally relates to the field of immunology and antibody engineering. Specifically, the present invention relates to various novel artificial antibody molecules, polynucleotides encoding the antibody molecules, vectors comprising the polynucleotides, host cells comprising the polynucleotides or vectors, immunoconjugates and pharmaceutical compositions comprising the antibody molecules, and use of the antibody molecules for immunotherapy, prevention and/or diagnosis of diseases.

SEQUENCE LISTING

The application contains a Sequence Listing which has been submitted electronically in ASCII format and is hereby incorporated by reference in its entirety. Said ASCII copy, created on Nov. 3, 2022, is named 11275_008843-US0_ST25-V3.txt and is 63,531 bytes in size.

BACKGROUND OF THE INVENTION

Antibody molecules capable of targeted specific binding to corresponding antigens thereof are becoming important therapeutic agents, preventive agents, and/or diagnostic agents for a variety of diseases such as cancers, autoimmune diseases, inflammatory diseases, infectious diseases, etc. However, monospecific antibodies against a single target have some limitations in clinical applications. Patients may develop resistance or no response after receiving monospecific antibody therapy. With researches on cancers and many other diseases, it is recognized that there are often multiple signal transduction pathways involved in the development and progression of diseases, and a single-target immunotherapy is usually insufficient to play a therapeutic role in many diseases.

Because multispecific antibodies such as bispecific antibodies can specifically bind to different antigens, when one antigen is located on a specific immune cell and another antigen is located on a diseased cell, multispecific antibodies such as bispecific antibodies can redirect specific immune cells to diseased cells to enhance the killing of immune cells to diseased cells. In addition, multispecific antibodies such as bispecific antibodies can also be designed to act on signal transduction pathways of two or more different mediators simultaneously. These advantages have expanded the application of multispecific antibodies such as bispecific antibodies.

A large number of imaginative patterns of multispecific antibodies (such as bispecific antibodies) have been developed through antibody engineering and their suitability in therapeutic applications has been studied (Brinkmann U. and Kontermann R. E., *The making of bispecific antibodies, Mabs*, 2017, 9(2): 182-212). Currently, two bispecific antibody products approved for marketing are Blinatumomab developed by Micromet and Amgen, and Catumaxomab developed by Trion Pharma. Blinatumomab is the first single-chain bispecific antibody approved for marketing in the United States for the treatment of B-cell non-Hodgkin's lymphoma (NHL) and B precursor acute lymphoblastic leukemia (ALL) with a molecular weight of about 55 KDa. It is a fusion of two single-chain Fv molecules against CD19 and CD3 respectively via a flexible linker peptide. Through CD19 expressed in almost all B lymphocyte tumors and CD3 expressed on T cells, Blinatumomab connects T cells and targeting cells (tumor cells) tightly together, allows T cells to release perforin and telomerase into synaptic space, and causes a series of chemical reactions in the tumor cells, thereby destroying the tumor cells (Nagorsen D. and Baeuerle P. A., *Immunomodulatory therapy of cancer with T cell-engaging BiTE antibody blinatumomab, Exp. Cell Res.*, 2011, 317: 1255-1260). Catumaxomab is a chimera composed of two incomplete antibodies derived from a mouse IgG2a isotype and a rat IgG2b isotype respectively. Each incomplete antibody has one light chain and one heavy chain. The anti-CD3 rat IgG2b portion is used for T cell recognition, and anti-tumor cell surface antigen EpCAM (epithelial cell adhesion molecule) mouse IgG2a portion is used for tumor cell recognition (Chelius D et al., *Structural and functional characterization of the trifunctional antibody Catumaxomab, MAbs*, 2010, 2: 309-319). Catumaxomab (Removab®) was approved in Europe in April, 2009 for the treatment of malignant ascites caused by EpCAM-positive epithelial-derived metastases.

Multispecific antibodies such as bispecific antibodies can be categorized based on different components and construction methods. For example, based on the substantial bilateral symmetry of multispecific antibody structures, they can be categorized into symmetrical antibodies and asymmetric antibodies; based on the presence or absence of IgG Fc region in multispecific antibodies, they can be categorized into antibody patterns with Fc region and antibody patterns without Fc region; based on the amount of antigen-binding sites in multispecific antibodies, they can be categorized into bivalent, trivalent, or tetravalent antibodies or those of greater valencies, and the like.

Multispecific antibody patterns in the prior art have their own advantages and disadvantages in preparation and application. For example, although Blinatumomab can be produced on a large scale using recombinant Chinese hamster ovary (CHO) cells, it is likely to form aggregates and has a short half-life in vivo, and an additional continuous infusion device is required in practice; Catumaxomab manufacturing process is complex and mouse heterologous antibodies are more likely to cause immunogenicity issues in humans.

Accordingly, there is still a need in the art for alternative multispecific antibody patterns having improved properties. The present invention provides a novel multispecific antibody pattern which is functioned as a building block by using single-domain antigen-binding sites having smaller molecular weights and high stability, and linked to N-terminus or C-terminus of Fab fragments. After the resulting linker is re-linked to the Fc region, it is easy to express effectively in cultivated cells in vitro without requiring complex manufacturing process. Moreover, the presence of the Fc region in the antibody pattern of the present invention allows to obtain purified antibodies using single-step affinity chromatography after expressing the antibodies of the present invention in cultivated cells, which have a longer serum half-life in vivo and can evoke effector functions, such as antibody-dependent cell-mediated cytotoxicity (ADCC), antibody-dependent cellular phagocytosis (ADCP) and complement-dependent cytotoxicity (CDC). The multispecific antibody pattern of the present invention can retain the affinity of each antigen-binding site in the multispecific antibody for binding to corresponding different epitopes, and generates no steric hindrance when binding to different epitopes, resulting in good druggability. Further, the multispecific antibody pattern of the present invention is physically stable and biologically stable, which provides the antibody with better productivity and developability.

SUMMARY OF THE INVENTION

Disclosed herein is a novel antibody molecule constructed by an antibody engineering technique. The antibody molecule is capable of binding to one or more antigens and preferably to two or more antigens with high affinity and high specificity. The present invention also provides a nucleic acid molecules encoding the antibody molecule, and an expression vector, a host cell and a method for producing the antibody molecule. The present invention also provides an immunoconjugate and a pharmaceutical composition comprising the antibody molecule disclosed herein. The antibody molecule disclosed herein may be used alone or in combination with other drugs or other treatment modalities to treat, prevent and/or diagnose diseases such as autoimmune diseases, acute and chronic inflammatory diseases, infectious diseases (e.g., chronic infectious diseases or sepsis), and tumors, etc.

Therefore, in one aspect, the present invention provides antibody molecules having one or more of the following characteristics:

(a) specifically binding to one or more antigens with high affinity, for example, with an affinity constant of at least about $10^7$ $M^{-1}$, preferably about $10^8$ $M^{-1}$ and more preferably about $10^9$ $M^{-1}$ or greater;

(b) easily expressed in cultivated cells in vitro, and chains of the antibody molecule can correctly couple or pair;

(c) having good physical stability, in particular, having good long-term thermal stability, and being capable of maintaining biological activities for a long time;

(d) exerting biological functions through regulating (e.g., inhibiting or activating) signaling pathways involving one or more antigens to which the antibody specifically binds; and (e) exerting effector functions through the Fc region after specifically binding to one or more antigens.

In one embodiment, the antibody molecule of the present invention comprises: (i) single-domain antigen-binding sites; (ii) antigen-binding Fab fragments, wherein the single-domain antigen-binding site is located at the N-terminus of a light chain variable domain (VL) of the antigen-binding Fab fragment or the C-terminus of a light chain constant region (CL) of the antigen-binding Fab fragment or the single-domain antigen-binding site is located at the N-terminus of a heavy chain variable domain (VH) or the C-terminus of an immunoglobulin CH1 domain of the antigen-binding Fab fragment, the single-domain antigen-binding site and the antigen-binding Fab fragment bind to the same antigen or different antigens, and the single-domain antigen-binding site and the antigen-binding Fab fragment have or do not have a linker peptide therebetween; and (iii) immunoglobulin Fc domains located at the C-terminus of the single-domain antigen-binding site or the antigen-binding Fab fragment.

In one embodiment, the antibody molecule of the present invention comprises at least four antigen-binding sites (at least two single-domain antigen-binding sites and at least two antigen-binding sites in Fab fragments) binding to at least four, three and two different antigens, or one antigen. With respect to each antigen to which the antibody molecule binds, the antigen-binding sites in the antibody molecule of the present invention binds to the same or different epitopes in antigen molecule. In one embodiment, the antibody molecule of the present invention comprises four antigen-binding sites, wherein two single-domain antigen-binding sites bind to the same or different epitopes in a first antigen, and two Fab fragments bind to the same or different epitopes in a second antigen, and the first antigen is different from the second antigen.

In one embodiment, the antibody molecule of the present invention comprises glycine and/or serine residues used alone or in combination that work as a linker peptide between the single-domain antigen-binding sites and the antigen-binding Fab fragments. For example, the linker peptide comprises an amino acid sequence $(Gly_4Ser)n$, wherein the n is a positive integer equal to or greater than 1, for example, a positive integer from 1 to 7, such as 2, 3, 4, 5, and 6.

In one embodiment, the single-domain antigen-binding sites in the antibody molecule of the present invention are selected from a heavy chain variable domain (VH), a light chain variable domain (VL), a heavy chain variable domain of an antibody naturally devoid of a light chain (e.g., a heavy chain variable domain of a heavy chain antibody naturally existing in the Camelidae species), a VH-like single domain in an immunoglobulin known as a novel antigen receptor (NAR) in fish (e.g., IgNAR naturally existing in shark serum), and a recombinant single-domain antigen-binding site derived therefrom (e.g., a camelized human VH domain or a humanized Camelidae antibody heavy chain variable domain). In one preferred embodiment, the single-domain antigen-binding sites in the antibody molecule of the present invention are selected from a heavy chain variable domain of a heavy chain antibody naturally existing in the Camelidae species, a camelized human VH domain, and a humanized Camelidae antibody heavy chain variable domain. The heavy chain variable domain derived from a heavy chain antibody naturally devoid of light chains is also referred to as VHH herein to distinguish it from the conventional VHs of a four-chain immunoglobulin. Such a VHH molecule may be derived from antibodies produced in Camelidae species such as camels, alpacas, dromedaries, llamas, and guanacos. Species other than Camelidae may also produce heavy chain antibodies naturally devoid of light chains, and such VHHs are also within the scope of the present invention.

In one embodiment, the present invention provides such an antibody molecule comprising four polypeptide chains, wherein each of a first polypeptide chain and a third polypeptide chain comprises an immunoglobulin light chain and a single-domain antigen-binding site (such as VHH) located at the N-terminus of the immunoglobulin light chain variable domain (VL); and each of a second polypeptide chain and a fourth polypeptide chain comprises an immunoglobulin heavy chain. Preferably, the immunoglobulin is an IgG1, an IgG2 or an IgG4, and more preferably, the immunoglobulin is a human IgG1.

In one embodiment, the present invention provides such an antibody molecule comprising four polypeptide chains, wherein each of a first polypeptide chain and a third polypeptide chain comprises an immunoglobulin light chain and a single-domain antigen-binding site (such as VHH) located at the C-terminus of the immunoglobulin light chain constant region (CL); and each of a second polypeptide chain and a fourth polypeptide chain comprises an immunoglobulin heavy chain. Preferably, the immunoglobulin is an IgG1, an IgG2 or an IgG4, and more preferably, the immunoglobulin is a human IgG1.

In one embodiment, the present invention provides such an antibody molecule comprising four polypeptide chains, wherein each of a first polypeptide chain and a third polypeptide chain comprises an immunoglobulin light chain; and each of a second polypeptide chain and a fourth polypeptide chain comprises an immunoglobulin heavy chain and a single-domain antigen-binding site (such as VHH) located at the N-terminus of the immunoglobulin heavy chain.

Preferably, the immunoglobulin is an IgG1, an IgG2 or an IgG4, and more preferably, the immunoglobulin is a human IgG1.

In one embodiment, the present invention provides such an antibody molecule comprising four polypeptide chains, wherein each of a first polypeptide chain and a third polypeptide chain comprises an immunoglobulin light chain; and each of a second polypeptide chain and a fourth polypeptide chain comprises, from N-terminus to C-terminus, an immunoglobulin heavy chain variable region, an immunoglobulin CH1 domain, a single-domain antigen-binding site (e.g., VHH), an immunoglobulin CH2 domain, an immunoglobulin CH3 domain, and optionally an immunoglobulin CH4 domain. Preferably, the immunoglobulin is an IgG1, an IgG2 or an IgG4, and more preferably, the immunoglobulin is a human IgG1.

In one embodiment, the present invention provides such an antibody molecule comprising four polypeptide chains, wherein each of a first polypeptide chain and a third polypeptide chain comprises, from N-terminus to C-terminus, a single-domain antigen-binding site (e.g., VHH), an immunoglobulin heavy chain variable domain (VH), and an immunoglobulin light chain constant region (CL); and each of a second polypeptide chain and a fourth polypeptide chain comprises, from N-terminus to C-terminus, an immunoglobulin light chain variable domain (VL), an immunoglobulin CH1 domain, an immunoglobulin CH2 domain, an immunoglobulin CH3 domain, and optionally an immunoglobulin CH4 domain. Preferably, the immunoglobulin is an IgG1, an IgG2 or an IgG4, and more preferably, the immunoglobulin is a human IgG1.

In one embodiment, the present invention provides such an antibody molecule comprising four polypeptide chains, wherein each of a first polypeptide chain and a third polypeptide chain comprises, from N-terminus to C-terminus, an immunoglobulin heavy chain variable domain (VH), an immunoglobulin light chain constant region (CL), and a single-domain antigen-binding site (e.g., VHH); and each of a second polypeptide chain and a fourth polypeptide chain comprises, from N-terminus to C-terminus, an immunoglobulin light chain variable domain (VL), an immunoglobulin CH1 domain, an immunoglobulin CH2 domain, an immunoglobulin CH3 domain, and optionally an immunoglobulin CH4 domain. Preferably, the immunoglobulin is an IgG1, an IgG2 or an IgG4, and more preferably, the immunoglobulin is a human IgG1.

In one embodiment, the present invention provides such an antibody molecule comprising four polypeptide chains, wherein each of a first polypeptide chain and a third polypeptide chain comprises, from N-terminus to C-terminus, an immunoglobulin heavy chain variable domain (VH) and an immunoglobulin light chain constant region (CL); and each of a second polypeptide chain and a fourth polypeptide chain comprises, from N-terminus to C-terminus, a single-domain antigen-binding site (e.g., VHH), an immunoglobulin light chain variable domain (VL), an immunoglobulin CH1 domain, an immunoglobulin CH2 domain, an immunoglobulin CH3 domain, and optionally an immunoglobulin CH4 domain. Preferably, the immunoglobulin is an IgG1, an IgG2 or an IgG4, and more preferably, the immunoglobulin is a human IgG1.

In one embodiment, the present invention provides such an antibody molecule comprising four polypeptide chains, wherein each of a first polypeptide chain and a third polypeptide chain comprises, from N-terminus to C-terminus, an immunoglobulin heavy chain variable domain (VH) and an immunoglobulin light chain constant region (CL); and each of a second polypeptide chain and a fourth polypeptide chain comprises, from N-terminus to C-terminus, an immunoglobulin light chain variable domain (VL), an immunoglobulin CH1 domain, a single-domain antigen-binding site (e.g., VHH), an immunoglobulin CH2 domain, an immunoglobulin CH3 domain, and optionally an immunoglobulin CH4 domain. Preferably, the immunoglobulin is an IgG1, an IgG2 or an IgG4, and more preferably, the immunoglobulin is a human IgG1.

In one embodiment, the present invention provides such an antibody molecule comprising four polypeptide chains, wherein each of a first polypeptide chain and a third polypeptide chain comprises, from N-terminus to C-terminus, a single-domain antigen-binding site (e.g., VHH), an immunoglobulin light chain variable domain (VL), and an immunoglobulin CH1 domain; and each of a second polypeptide chain and a fourth polypeptide chain comprises, from N-terminus to C-terminus, an immunoglobulin heavy chain variable domain (VH), an immunoglobulin light chain constant region (CL), an immunoglobulin CH2 domain, an immunoglobulin CH3 domain, and optionally an immunoglobulin CH4 domain. Preferably, the immunoglobulin is an IgG1, an IgG2 or an IgG4, and more preferably, the immunoglobulin is a human IgG1.

In one embodiment, the present invention provides such an antibody molecule comprising four polypeptide chains, wherein each of a first polypeptide chain and a third polypeptide chain comprises, from N-terminus to C-terminus, an immunoglobulin light chain variable domain (VL), an immunoglobulin CH1 domain, and a single-domain antigen-binding site (e.g., VHH); and each of a second polypeptide chain and a fourth polypeptide chain comprises, from N-terminus to C-terminus, an immunoglobulin heavy chain variable domain (VH), an immunoglobulin light chain constant region (CL), an immunoglobulin CH2 domain, an immunoglobulin CH3 domain, and optionally an immunoglobulin CH4 domain. Preferably, the immunoglobulin is an IgG1, an IgG2 or an IgG4, and more preferably, the immunoglobulin is a human IgG1.

In one embodiment, the present invention provides such an antibody molecule comprising four polypeptide chains, wherein each of a first polypeptide chain and a third polypeptide chain comprises, from N-terminus to C-terminus, an immunoglobulin light chain variable domain (VL) and an immunoglobulin CH1 domain; and each of a second polypeptide chain and a fourth polypeptide chain comprises, from N-terminus to C-terminus, a single-domain antigen-binding site (e.g., VHH), an immunoglobulin heavy chain variable domain (VH), an immunoglobulin light chain constant region (CL), an immunoglobulin CH2 domain, an immunoglobulin CH3 domain, and optionally an immunoglobulin CH4 domain. Preferably, the immunoglobulin is an IgG1, an IgG2 or an IgG4, and more preferably, the immunoglobulin is a human IgG1.

In one embodiment, the present invention provides such an antibody molecule comprising four polypeptide chains, wherein each of a first polypeptide chain and a third polypeptide chain comprises, from N-terminus to C-terminus, an immunoglobulin light chain variable domain (VL) and an immunoglobulin CH1 domain; and each of a second polypeptide chain and a fourth polypeptide chain comprises, from N-terminus to C-terminus, an immunoglobulin heavy chain variable domain (VH), an immunoglobulin light chain constant region (CL), a single-domain antigen-binding site (e.g., VHH), an immunoglobulin CH2 domain, an immunoglobulin CH3 domain, and optionally an immunoglobulin CH4 domain. Preferably, the immunoglobulin is an IgG1, an IgG2 or an IgG4, and more preferably, the immunoglobulin is a human IgG1.

In an antibody molecule comprising four polypeptide chains provided by the present invention, the inventor also designs amino acid residues which may stabilize the antibody molecule structure and facilitate the correct coupling or pairing between the chains. For example, Fc domains of a second polypeptide chain and a fourth polypeptide chain of the antibody molecule comprise a hinge region having "CPPC" amino acid residues (SEQ ID NO: 32), thereby the second polypeptide chain and the fourth polypeptide chain are stably associated with each other via disulfide bonds formed between the amino acid residues at the hinge region. In one embodiment, the second polypeptide chain and the fourth polypeptide chain of the antibody molecule of the present invention respectively comprise Y349C and S354C, or S354C and Y349C in their Fc domains (numbered by EU index according to Kabat et al., *Sequences of Proteins of Immunological Interest*, 5th edition, Public Health Service, National Institutes of Health, Bethesda, Md. (1991), hereinafter referred to as "EU numbering"), thereby the second polypeptide chain and the fourth polypeptide chain further form inter-chain disulfide bonds in the Fc domains to stabilize correct pairing of the second polypeptide chain and the fourth polypeptide chain.

In one embodiment, the Fc domains of the second polypeptide chain and/or the fourth polypeptide chain of the antibody molecule of the present invention comprise an amino acid mutation which affects the effector function of the antibody. In one specific embodiment, the effector function is antibody-dependent cell-mediated cytotoxicity (ADCC). In one embodiment, the amino acid mutation occurs in a CH2 domain of the Fc region. For example, the antibody molecule comprises amino acid replacements at positions 234 and 235 (EU numbering) of a second polypeptide chain and/or a fourth polypeptide chain. In one specific embodiment, the amino acid replacements are L234A and L235A (hereinafter referred to as "LALA mutations").

In one embodiment, a second polypeptide chain and a fourth polypeptide chain of the antibody molecule of the present invention respectively comprise a protuberance ("knob") and a cavity ("hole") in their Fc domains, or vice versa, and the protuberance or the cavity in Fc domains of the second polypeptide chain may be respectively placed at the cavity or the protuberance of the fourth polypeptide chain, thereby the second polypeptide chain and the fourth polypeptide chain form a stable association of "knob-in-hole" with each other. In one embodiment, the amino acid replacement T366W is contained in one of the second polypeptide chain and the fourth polypeptide chain, and the amino acid replacements T366S, L368A, and Y407V (EU numbering) are contained in the other one of the second polypeptide chain and the fourth polypeptide chain. Thereby the protuberance in one chain can be placed at the cavity in the other chain, which facilitates the correct pairing of the second polypeptide chain and the fourth polypeptide chain.

In one embodiment, the immunoglobulin CL domain and CH1 domain of the first polypeptide chain and the second polypeptide chain of the antibody molecule of the present invention respectively comprise a protuberance and a cavity, or vice versa, and the protuberance or the cavity in the CH1 domain may be respectively placed at the cavity or the protuberance in the CL domain, thereby the first polypeptide chain and the second polypeptide chain also form a stable association of "knob-in-hole" with each other. Likewise, the immunoglobulin CL domain and CH1 domain of the third polypeptide chain and the fourth polypeptide chain of the antibody molecule of the present invention also respectively comprise a protuberance and a cavity, or vice versa, and the protuberance or the cavity in the CH1 domain may be respectively placed at the cavity or the protuberance in the CL domain, thereby the third polypeptide chain and the fourth polypeptide chain also form a stable association of "knob-in-hole" with each other.

In one embodiment, two single-domain antigen-binding sites of the antibody molecule of the present invention bind to the same epitope in a first antigen, and two Fab fragments bind to the same epitope in a second antigen, thereby the antibody molecule is a bispecific antibody against the first antigen and the second antigen.

The type of antigen to which the antibody molecule of the present invention specifically binds is not particularly limited, and the antigen may be, for example, a cytokine, a growth factor, a hormone, a signaling protein, an inflammatory mediator, a ligand, a cell surface receptor, or a fragment thereof. In one embodiment, the antigen to which the antibody molecule of the present invention specifically binds is selected from tumor-associated antigens, immune checkpoint molecules, angiogenesis inducing factors, members of the tumor necrosis factor receptor superfamily and co-stimulatory molecules in the immune system, as well as ligands and/or receptors of such molecules, such as OX40, CD47, PD1, PD-L1, PD-L2, LAG-3, 4-1BB (CD137), VEGF and GITR.

The present invention exemplifies several types of bispecific antibodies as described below.

i) In one embodiment, the antibody molecule of the present invention is an anti-OX40/PD-L1 bispecific antibody that is capable of binding to the Tumor Necrosis Factor (TNF) receptor family member OX40 expressed on the surface of lymphocytes with an affinity constant of at least about $10^7$ $M^{-1}$, preferably about $10^8$ $M^{-1}$ and more preferably about $10^9$ $M^{-1}$ or greater, thereby activating T cells, such as enhancing the immunostimulatory/effector function of effector T cells and/or ensuring the proliferation of these cells and/or down-regulating the immunosuppressive function of regulatory T cells; and binds to PD-L1 on the surface of tumor cells with an affinity constant of at least about $10^7$ $M^{-1}$, preferably about $10^8$ $M^{-1}$ and more preferably about $10^9$ $M^{-1}$ or greater, thereby inhibiting binding of PD-1 on T cells to PD-L1 on the surface of tumor cells, inducing T cell activation and exerting an anti-tumor effect.

In one embodiment, the anti-OX40/PD-L1 bispecific antibody of the present invention consists of 4 polypeptide chains that are substantially bilaterally symmetrical, wherein the 2 polypeptide chains in the left half and the 2 polypeptide chains in the right half comprise (i) single-domain antigen-binding sites; (ii) antigen-binding Fab fragments, wherein the single-domain antigen-binding site is located at the N-terminus of a light chain variable domain (VL) of the antigen-binding Fab fragment or the C-terminus of a light chain constant region (CL) of the antigen-binding Fab fragment or the single-domain antigen-binding site is located at the N-terminus of a heavy chain variable domain (VH) or the C-terminus of an immunoglobulin CH1 domain of the antigen-binding Fab fragment, the single-domain antigen-binding site and the antigen-binding Fab fragment bind to OX40 and PD-L1 respectively or vice versa, and the single-domain antigen-binding site and the antigen-binding Fab fragment have or do not have a linker peptide therebetween; and (iii) immunoglobulin Fc domains located at the C-terminus of the single-domain antigen-binding site or the antigen-binding Fab fragment.

In one embodiment, the single-domain antigen-binding site in the anti-OX40/PD-L1 bispecific antibody of the present invention is a VHH specifically binding to PD-L1, and the Fab fragment is an anti-OX40 antibody Fab fragment specifically binding to OX40.

In one preferred embodiment, the VHH specifically binding to PD-L1 in the anti-OX40/PD-L1 bispecific antibody of the present invention comprises a CDR1 set forth in SEQ ID NO: 3, a CDR2 set forth in SEQ ID NO: 4 and a CDR3 set forth in SEQ ID NO: 5, or sequences having one, two, three, four, five, six or more amino acid alterations (e.g., amino acid replacements or deletions) compared to one or more of the 3 CDRs; the anti-OX40 antibody Fab fragment specifically binding to OX40 in the anti-OX40/PD-L1 bispecific antibody of the present invention comprises all the 6 heavy chain complementarity determining regions (CDRs) and light chain CDRs derived from the paired heavy chain and light chain variable region sequences set forth in SEQ ID NOs: 11 and 7 of the anti-OX40 antibody ADI-20112, or sequences having one, two, three, four, five, six, or more amino acid alterations (e.g., amino acid replacements or deletions) compared to one or more of the 6 CDRs.

In yet another embodiment, the VHH specifically binding to PD-L1 in the anti-OX40/PD-L1 bispecific antibody of the present invention comprises an amino acid sequence set forth in SEQ ID NO: 1 or SEQ ID NO: 2, or a sequence substantially identical (e.g., having at least 80%, 85%, 90%, 92%, 95%, 97%, 98%, 99% or higher identity) thereto; the anti-OX40 antibody Fab fragment specifically binding to OX40 in the anti-OX40/PD-L1 bispecific antibody of the present invention comprises the paired heavy chain and light chain variable region sequences set forth in SEQ ID NOs: 11 and 7 derived from the anti-OX40 antibody ADI-20112, or sequences having at least 90%, 91%, 92%, 93%, 94%, 95%, 96%, 97%, 98%, 99% or higher sequence identity to the paired heavy chain and light chain variable region sequences.

In yet another preferred embodiment, the anti-OX40/PD-L1 bispecific antibody of the present invention consists of 4 polypeptide chains that are substantially bilaterally symmetrical, wherein the 2 polypeptide chains in the left half of the antibody molecule comprise a first polypeptide chain set forth in SEQ ID NO: 6 and a second polypeptide chain set forth in SEQ ID NO: 10, respectively; or a first polypeptide chain set forth in SEQ ID NO: 14 and a second polypeptide chain set forth in SEQ ID NO: 10, respectively; or a first polypeptide chain set forth in SEQ ID NO: 15 and a second polypeptide chain set forth in SEQ ID NO: 16, respectively; or a first polypeptide chain set forth in SEQ ID NO: 15 and a second polypeptide chain set forth in SEQ ID NO: 17, respectively; or sequences substantially identical (e.g., having at least 80%, 85%, 90%, 92%, 95%, 97%, 98%, 99% or higher identity) to any one of the sequences; accordingly, the 2 polypeptide chains in the right half of the antibody molecule comprise a third polypeptide chain set forth in SEQ ID NO: 6 and a fourth polypeptide chain set forth in SEQ ID NO: 10, respectively; or a third polypeptide chain set forth in SEQ ID NO: 14 and a fourth polypeptide chain set forth in SEQ ID NO: 10, respectively; or a third polypeptide chain set forth in SEQ ID NO: 15 and a fourth polypeptide chain set forth in SEQ ID NO: 16, respectively; or a third polypeptide chain set forth in SEQ ID NO: 15 and a fourth polypeptide chain set forth in SEQ ID NO: 17, respectively; or sequences substantially identical (e.g., having at least 80%, 85%, 90%, 92%, 95%, 97%, 98%, 99% or higher identity) to any one of the sequences.

ii) In one embodiment, the antibody molecule of the present invention is an anti-VEGF/GITR bispecific antibody, wherein the antibody can bind to a vascular endothelial growth factor (VEGF) with an affinity constant of at least about $10^7$ $M^{-1}$, preferably about $10^8$ $M^{-1}$, and more preferably about $10^9$ $M^{-1}$ or greater, which blocks the binding of VEGF to receptor thereof (VEGFR) and inactivates VEGFR, thereby exerting an anti-angiogenesis effect, e.g., an anti-tumor angiogenesis effect, and inhibiting tumor growth, and the antibody also binds to glucocorticoid-induced tumor necrosis factor receptor (GITR) on $CD4^+$ and $CD8^+$ T cells with an affinity constant of at least about $10^7$ $M^{-1}$, preferably about $10^8$ $M^{-1}$, and more preferably about $10^9$ $M^{-1}$ or greater, thereby reversing the suppressive effects of regulatory T cells (Treg) and co-stimulating and activating effector T cells to exert an anti-tumor effect.

In one embodiment, the anti-VEGF/GITR bispecific antibody of the present invention consists of 4 polypeptide chains that are substantially bilaterally symmetrical, wherein the 2 polypeptide chains in the left half and the 2 polypeptide chains in the right half both comprise: (i) single-domain antigen-binding sites; (ii) antigen-binding Fab fragments, wherein the single-domain antigen-binding site is located at the N-terminus of a light chain variable domain (VL) of the antigen-binding Fab fragment or the C-terminus of a light chain constant region (CL) of the antigen-binding Fab fragment or the single-domain antigen-binding site is located at the N-terminus of a heavy chain variable domain (VH) or the C-terminus of an immunoglobulin CH1 domain of the antigen-binding Fab fragment, the single-domain antigen-binding site and the antigen-binding Fab fragment bind to VEGF and GITR respectively or vice versa, and the single-domain antigen-binding site and the antigen-binding Fab fragment have or do not have a linker peptide therebetween; and (iii) immunoglobulin Fc domains located at the C-terminus of the single-domain antigen-binding site or the antigen-binding Fab fragment.

In one embodiment, the single-domain antigen-binding site of the anti-VEGF/GITR bispecific antibody of the present invention is a VHH specifically binding to GITR, and the Fab fragment is an anti-VEGF antibody Fab fragment specifically binding to VEGF.

In one preferred embodiment, the VHH specifically binding to GITR in the anti-VEGF/GITR bispecific antibody of the present invention comprises a CDR1 set forth in GFAFGSS (SEQ ID NO: 25), a CDR2 set forth in SGGGFGD (SEQ ID NO: 26) and a CDR3 set forth in ATDWRKP (SEQ ID NO: 27), or sequences having one, two, three, four, five, six or more amino acid alterations (e.g., amino acid replacements or deletions) compared to one or more of the 3 CDRs; the anti-VEGF antibody Fab fragment specifically binding to VEGF in the anti-VEGF/GITR bispecific antibody of the present invention comprises all the 6 heavy chain complementarity determining regions (CDRs) and light chain CDRs in the paired heavy chain and light chain variable region sequences set forth in SEQ ID NOs: 22 and 20 derived from Avastin, an anti-VEGF antibody, or sequences having one, two, three, four, five, six, or more amino acid alterations (e.g., amino acid replacements or deletions) compared to one or more of the 6 CDRs.

In yet another embodiment, the VHH specifically binding to GITR in the anti-VEGF/GITR bispecific antibody of the present invention comprises an anti-GITR VHH amino acid sequence set forth in SEQ ID NO: 24, or a sequence substantially identical (e.g., having at least 80%, 85%, 90%, 92%, 95%, 97%, 98%, 99% or higher identity) thereto; the anti-VEGF antibody Fab fragment specifically binding to VEGF in the anti-VEGF/GITR bispecific antibody of the present invention comprises the paired heavy chain and light chain variable region sequences set forth in SEQ ID NOs: 22 and 20 derived from Avastin, an anti-VEGF antibody, or sequences having at least 90%, 91%, 92%, 93%, 94%, 95%, 96%, 97%, 98%, 99% or higher sequence identity to the paired heavy chain and light chain variable region sequences.

In yet another preferred embodiment, the anti-VEGF/GITR bispecific antibody of the present invention consists of 4 polypeptide chains that are substantially bilaterally symmetrical, wherein the 2 polypeptide chains in the left half of the antibody molecule comprise a first polypeptide chain set forth in SEQ ID NO: 18 and a second polypeptide chain set forth in SEQ ID NO: 21 respectively, or a first polypeptide chain set forth in SEQ ID NO: 18 and a second polypeptide chain set forth in SEQ ID NO: 28 respectively, or sequences substantially identical (e.g., having at least 80%, 85%, 90%, 92%, 95%, 97%, 98%, 99% or higher identity) to any of the sequences and, accordingly, the 2 polypeptide chains in the right half of the antibody molecule comprise a third polypeptide chain set forth in SEQ ID NO: 18 and a fourth polypeptide chain set forth in SEQ ID NO: 21 respectively, or a third polypeptide chain set forth in SEQ ID NO: 18 and a fourth polypeptide chain set forth in SEQ ID NO: 28 respectively, or sequences substantially identical (e.g., having at least 80%, 85%, 90%, 92%, 95%, 97%, 98%, 99% or higher identity) to any of the sequences.

In a second aspect, the present invention provides a polynucleotide encoding any one or more polypeptide chains in the antibody molecule of the present invention.

In a third aspect, the present invention provides a vector, preferably an expression vector, comprising the polynucleotide encoding any one or more polypeptide chains in the antibody molecule of the present invention.

In a fourth aspect, the present invention provides a host cell comprising the polynucleotide or the vector of the present invention. For example, the host cell is a mammalian cell, preferably a CHO cell or a HEK293 cell; and the host cell is a prokaryotic cell, preferably an *E. coli* cell.

In a fifth aspect, the present invention provides a method for producing the antibody molecule of the present invention, which comprises: (i) cultivating the host cell of the present invention under conditions suitable for expressing the antibody molecule, and (ii) isolating the antibody molecule from the host cell or the cultures.

In a sixth aspect, the present invention provides an immunoconjugate and a pharmaceutical composition both comprising the antibody molecule of the present invention. The antibody molecule disclosed herein may be used alone or in combination with other drugs or other treatment modalities to treat, prevent and/or diagnose diseases such as autoimmune diseases, acute and chronic inflammatory diseases, infectious diseases (e.g., chronic infectious diseases or sepsis), and tumors, etc.

In a seventh aspect, the present invention provides the use of the antibody molecule, the immunoconjugate, and the pharmaceutical composition of the present invention as a drug for treating and/or preventing a disease in an individual or as a diagnostic tool for a disease. Preferably, the individual is a mammal, and more preferably a human. In one embodiment, the disease is an autoimmune disease, an acute or chronic inflammatory disease, an infectious disease (e.g., a chronic infectious disease or sepsis), or a tumor.

Unless defined otherwise, all technical and scientific terms used herein have the same meaning as commonly understood by those of ordinary skill in the art to which the present invention belongs. All publications, patent applications, patents, and other references mentioned herein are incorporated by reference in their entireties. In addition, the materials, methods, and examples described herein are illustrative only and are not intended to be limiting. Other features, objectives, and advantages of the present invention will be apparent from the specification and drawings, and from the appended claims.

BRIEF DESCRIPTION OF THE DRAWINGS

The preferred embodiments of the present invention described in detail below will be better understood when read in conjunction with the following drawings. For the purpose of illustrating the present invention, currently preferred embodiments are shown in the drawings. However, it should be understood that the present invention is not limited to accurate arrangement and means of the embodiments shown in the drawings.

DETAILED DESCRIPTION

I. Definitions

Figure 1A:
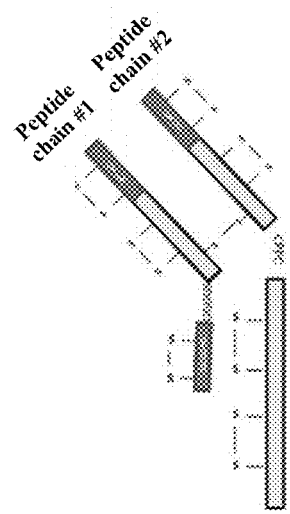
FIGS. 1A-1D illustrate 4 structures of the bispecific antibody of the present invention. The hinge region comprises the amino acid sequence "CPPC" (SEQ ID NO: 32).

The term "about" used in combination with a numerical value is intended to encompass the numerical values in a range from a lower limit less than the specified numerical value by 5% to an upper limit greater than the specified numerical value by 5%.

As used herein, the term "contain" or "comprise" is intended to mean that the elements, integers or steps are included, but not to the exclusion of any other elements, integers or steps.

The term "antibody" is used herein in the broadest sense, refers to a protein comprising an antigen-binding site, and encompasses natural and artificial antibodies with various structures, including but not limited to monoclonal antibodies, polyclonal antibodies, multispecific antibodies (e.g., bispecific antibodies), single-chain antibodies, intact antibodies, and antibody fragments.

The terms "whole antibody", "full-length antibody", "complete antibody" and "intact antibody" are used interchangeably herein to refer to a naturally occurring glycoprotein comprising at least two heavy (H) chains and two light (L) chains interconnected by disulfide bonds. Each heavy chain consists of a heavy chain variable region (abbreviated herein as VH) and a heavy chain constant region. The heavy chain constant region consists of 3 domains CH1, CH2 and CH3. Each light chain consists of a light chain variable region (abbreviated herein as VL) and a light chain constant region. The light chain constant region consists of a domain CL. The VH region and the VL region can be further divided into hypervariable regions (complementarity determining regions, or CDRs), with more conservative regions (framework regions, or FRs) inserted therebetween. Each VH or VL consists of three CDRs and four FRs, arranged from the N-terminus to C-terminus in the following order: FR1, CDR1, FR2, CDR2, FR3, CDR3, FR4. The constant regions are not directly involved in binding of antibodies to antigens, but exhibit a variety of effector functions.

The term "antigen-binding fragment" is a portion or segment of an intact or a complete antibody that has fewer amino acid residues than an intact or a complete antibody, which can bind to an antigen or compete with an intact antibody (i.e., an intact antibody from which the antigen-binding fragment is derived) for binding to an antigen. An antigen-binding fragment may be prepared by recombinant DNA techniques, or by enzymatic or chemical cleavage of an intact antibody. Antigen-binding fragments include, but are not limited to, Fab, Fab', F(ab')$_2$, Fv, single-chain Fv, diabodies, and single-domain antibodies (sdAbs). The Fab fragment is a monovalent fragment consisting of VL, VH, CL and CH1 domains. For example, the Fab fragment can be obtained by papain digestion of a complete antibody. In addition, the F(ab')$_2$, a dimer of Fab', is a bivalent antibody fragment produced by pepsin digestion of the portion below disulfide bonds in the hinge region of a complete antibody. The F(ab')2 can be reduced by disrupting the disulfide bonds in the hinge region under neutral conditions and the F(ab')$_2$ dimer is thus converted into a Fab' monomer. The Fab' monomer is substantially a Fab fragment with a hinge region (for more detailed descriptions of the antibody fragment, see Fundamental Immunology, W. E. Paul (ed.), Raven Press, N.Y. (1993)). The Fv fragment consists of the VL and VH domains of a single arm of an antibody. In addition, although the two domains VL and VH of the Fv fragment are encoded by separate genes, using the recombinant method, the domains can be linked by a synthetic linker peptide capable of making these two domains produced as a single protein chain in which the VL and VH regions pair to form a single chain Fv. The antibody fragment can be obtained by a chemical method, a recombinant DNA method, or a protease digestion method.

The term "single-domain antibody" (sdAb) or "single variable domain (SVD) antibody" generally refers to an antibody in which a single variable domain (e.g., a heavy chain variable domain (VH) or a light chain variable domain (VL), a heavy chain variable domain derived from a Camelidae heavy chain antibody, and a VH-like single domain (v-NAR) derived from fish IgNAR) can impart antigen binding. That is, the single variable domain requires no interaction with other variable domains to recognize target antigen. Examples of single domain antibodies include single domain antibodies derived from Camelidae (Llama and camel) and cartilaginous fishes (e.g., nurse sharks) (WO2005/035572).

The term "camelized human VH domain" refers to transferring key elements derived from a Camelidae VHH to a human VH domain, causing that the camelized human VH domain can alone impart antigen binding specificity without the human VH domain pairing with a VL domain to recognize the target antigen.

The term "binding site" or "antigen-binding site" as used herein refers to a region in an antibody molecule that actually binds to an antigen, which includes VH/VL pairs consisting of light chain variable domains (VL) of antibodies and heavy chain variable domains (VH) of antibodies, heavy chain variable domains derived from Camelidae heavy chain antibodies, VH-like single domains of IgNAR (v-NAR) from sharks, camelized human VH domains, and heavy chain variable domains of humanized Camelidae antibodies. In one embodiment of the present invention, the antibody molecule of the present invention comprises at least four antigen-binding sites, e.g. two single-domain antigen-binding sites (e.g., VHH) and two antigen-binding sites formed by VH/VL pairs in Fab fragments.

The term "single-domain antigen-binding site" refers to a region of an antibody molecule that actually binds to an antigen with a single variable domain (e.g., a heavy chain variable domain (VH), a light chain variable domain (VL), a heavy chain variable domain derived from a Camelidae heavy chain antibody, a v-NAR of IgNAR derived from sharks, a camelized human VH domain, a heavy chain variable domain of a humanized Camelidae antibody, and recombinant single domains thereof). In one embodiment of the present invention, the antibody molecule of the present invention comprises two single-domain antigen-binding sites, which respectively bind to the same and different antigens, or vice versa. In another embodiment of the present invention, the antibody molecule of the present invention comprises two single-domain antigen-binding sites, which respectively bind to the same and different epitopes, or vice versa.

As used herein, the term "monospecific antibody" refers to an antibody having one or more binding sites, each of which binds to the same epitope of the same antigen.

As used herein, the term "multispecific antibody" refers to an antibody having at least two antigen-binding sites, each of which binds to a different epitope of the same antigen or a different epitope of a different antigen. The antibody provided herein is generally a multispecific antibody, such as a bispecific antibody. A multispecific antibody is an antibody having binding specificities for at least two different epitopes. In one embodiment, provided herein is a bispecific antibody having binding specificities for a first antigen and a second antigen.

The term "immunoglobulin molecule" refers to a protein having a structure of a naturally existing antibody. For example, an IgG is a heterotetrameric glycoprotein of about 150,000 Daltons consisting of two light chains and two heavy chains which are disulfide-bonded. Each immunoglobulin heavy chain has a heavy chain variable region (VH), also called a heavy chain variable domain, followed by three heavy chain constant domains (CH1, CH2, and CH3) from N-terminus to C-terminus. Similarly, each immunoglobulin light chain has a light chain variable region (VL), also called a light chain variable domain, followed by a light chain constant domain (CL) from N-terminus to C-terminus. The heavy chains of an immunoglobulin can be assigned to one of five classes, α (IgA), δ (IgD), ε (IgE), γ (IgG), or μ (IgM), in which some classes can be further divided into subclasses such as $\gamma_1$ (IgG$_1$), $\gamma_2$ (IgG$_2$), $\gamma_3$ (IgG$_3$), $\gamma_4$ (IgG$_4$), $\alpha_1$ (IgA$_1$), and $\alpha_2$ (IgA$_2$). The light chains of an immunoglobulin can be divided into one of two categories, κ or λ, based on the amino acid sequence of constant domains thereof. An immunoglobulin consists essentially of two Fab molecules and one Fc domain linked by an immunoglobulin hinge region.

The term "Fc domain" or "Fc region" is used herein to define a C-terminus region of an immunoglobulin heavy chain, which comprises at least a portion of a constant region. The term includes Fc regions of native sequences and variant Fc regions. A native immunoglobulin "Fc domain" comprises two or three constant domains, i.e., a CH2 domain, a CH3 domain, and an optional CH4 domain. For example, in native antibodies, an immunoglobulin Fc domain comprises the second and the third constant domains (CH2 domain and CH3 domain) derived from two heavy chains of IgG, IgA, and IgD antibodies; or comprises the second, the third and the fourth constant domains (CH2 domain, CH3 domain and CH4 domain) derived from two heavy chains of IgM and IgE antibodies. Unless otherwise stated herein, amino acid residues in Fc regions or heavy chain constant regions are numbered according to the EU numbering system (also known as the EU Index) described in, for example, Kabat et al., *Sequences of Proteins of Immunological Interest,* 5th Edition, Public Health Service, National Institutes of Health, Bethesda, Md., 1991.

The term "effector function" refers to bioactivities attributed to an immunoglobulin Fc region that vary with immunoglobulin isotype. Examples of immunoglobulin effector functions include: C1q binding and complement-dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake in antigen-presenting cells, down regulation of cell surface receptors (such as B-cell receptors), and B-cell activation.

The term "chimeric antibody" is an antibody molecule in which: (a) a constant region or a portion thereof is modified, substituted, or exchanged such that antigen-binding sites are linked to constant regions of different or modified classes, effector functions and/or species, or disparate molecules imparting new properties (e.g., enzymes, toxins, hormones, growth factors, and drugs) to chimeric antibodies, etc.; or (b) a constant region or a portion thereof is modified, substituted, or exchanged by variable regions with different or modified antigen binding specificities. For example, a mouse antibody can be modified by substituting its constant region for a constant region from a human immunoglobulin. Due to the replacement of a human constant region, the chimeric antibody can retain its specificity for recognizing antigens, while having reduced antigenicity in humans as compared to the original mouse antibody. "Humanized antibody" is an antibody that retains the antigen-specific reactivity of a non-human antibody (such as a mouse monoclonal antibody) and has lower immunogenicity when administered to humans as a therapeutic agent. This can be achieved, for example, by retaining non-human antigen-binding sites and substituting the remainder of the antibodies for their human counterparts (i.e., the portions of the constant and variable regions not involved in binding are the corresponding parts of human antibodies). See, e.g., Padlan, *Anatomy of the antibody molecule, Mol. Immun.,* 1994, 31: 169-217. Other examples of human antibody engineering techniques include, but are not limited to, the Xoma technology disclosed in U.S. Pat. No. 5,766,886.

The term " . . . valent" antibody refers to the number of antigen-binding sites present in an antibody molecule. "Bivalent", "trivalent", and "tetravalent" antibodies refer to the presence of 2 antigen-binding sites, 3 binding sites, and 4 binding sites in an antibody molecule, respectively. In one embodiment, the bispecific antibody reported herein is "tetravalent".

The term "an antibody consisting of 4 polypeptide chains that are substantially bilaterally symmetrical" means that the antibody molecule consists of 4 polypeptide chains, including 2 polypeptide chains in the left and 2 polypeptide chains in the right of the antibody molecule, and the sequences of the 2 polypeptide chains in the left and the 2 polypeptide chains in the right of the antibody molecule have 100% identity, or at least 95% identity or at least 99% identity.

The term "flexible linker peptide" or "linker peptide" refers to a linker peptide consisting of amino acids, such as glycine and/or serine residues used alone or in combination, to link various variable domains in an antibody. In one embodiment, the flexible linker peptide is a Gly/Ser linker comprising an amino acid sequence (Gly$_4$Ser)n, wherein n is a positive integer equal to or greater than 1, for example, a positive integer from 1 to 7. In one embodiment, the flexible linker peptide is (Gly$_4$Ser)$_2$ (SEQ ID NO: 9). Also included within the scope of the present invention is the linker peptide described in WO2012/138475, which is incorporated herein by reference.

As used herein, the term "binding" or "specific binding" means that the binding effect is selective for antigens and can be distinguished from unwanted or non-specific interactions. The ability of an antigen-binding site to bind to a particular antigen can be determined by an enzyme-linked immunosorbent assay (ELISA) or a conventional binding assay known in the art.

"Affinity" or "binding affinity" refers to inherent binding affinity that reflects interactions between members of a binding pair. The affinity of molecule X for its partner Y can be generally represented by the dissociation constant ($K_D$), which is the ratio of dissociation rate constant to association rate constant ($k_{dis}$ and $k_{on}$, respectively). Affinity can be measured by common methods known in the art. One specific method for measuring affinity is the ForteBio kinetic binding assay described herein.

The term "antigen" refers to a molecule that induces an immune response. Such an immune response may involve antibody production or activation of specific immune cells, or both.

Those skilled will understand that any macromolecules, including essentially all proteins or peptides, can be used as antigens. In addition, an antigen may be derived from recombinant or genomic DNA. In some embodiments described herein, a first antigen, a second antigen, and a third antigen are three different antigens.

The terms "tumor-associated antigen" and "cancer antigen" can be used interchangeably to refer to molecules (generally proteins, carbohydrates, or lipids) preferably expressed completely or as fragments (e.g., MHC/peptide) on the surface of cancer cells, compared to normal cells, and the molecules can be used in the preferential targeting of cancer cells by the agent. In some embodiments, the tumor-associated antigen is a cell surface molecule overexpressed in tumor cells compared to normal cells, such as 1-fold overexpression, 2-fold overexpression, 3-fold overexpression, or more fold overexpression compared to normal cells.

In some embodiments, the tumor-associated antigen is a cell surface molecule inappropriately synthesized in tumor cells, such as a molecule comprising deletions, additions or mutations compared to molecules expressed on normal cells. In some embodiments, the tumor-associated antigen is expressed completely or as fragments only on the surface of tumor cells, and is not synthesized or expressed on the surface of normal cells. Many tumor-associated antigens are disclosed in the prior art, such as epidermal growth factor receptor variant III (EGFRvIII), tumor-associated glycoprotein 72 (TAG72), carcinoembryonic antigen (CEA), epithelial cell adhesion molecule (EPCAM), interleukin 11 receptor alpha (IL-IIRa), vascular endothelial growth factor receptor 2 (VEGFR2), epidermal growth factor receptor (EGFR), nerve cell adhesion molecule (NCAM), insulin-like growth factor 1 receptor (IGF-I receptor), melanoma-associated antigen 1 (MAGE-A1), CD72, CD47, and the like.

The term "immune checkpoint" means a class of inhibitory signaling molecules that are present in the immune system, which avoid tissue damage by regulating the persistence and strength of the immune response in peripheral tissues, and participate in maintaining the tolerance to self-antigens (Pardoll D M., *The Blockade of Immune Checkpoints in Cancer Immunotherapy, Nat Rev Cancer*, 2012, 12 (4): 252-264). Studies have found that one of the reasons that tumor cells can escape the immune system in the body and proliferate out of control is that the cells take use of the inhibitory signaling pathway of immune checkpoints, thereby inhibiting the activity of T lymphocytes, disabling T lymphocytes' killing effect on tumors (Yao S, Zhu Y, and Chen L., *Advances in Targeting Cell Surface Signaling Molecules for Immune Modulation. Nat Rev Drug Discov*, 2013, 12 (2): 130-146). Immune checkpoint molecules include, but are not limited to, programmed death 1 (PD-1), PD-L1, PD-L2, cytotoxic T lymphocyte antigen 4 (CTLA-4), LAG-3, and TIM-3.

The term "co-stimulatory molecule" refers to a corresponding binding partner on a T cell that specifically binds to a co-stimulatory ligand to mediate a T-cell co-stimulatory response, such as, but not limited to, proliferation. Co-stimulatory molecules are cell surface molecules other than antigen receptors or ligands thereof that contribute to effective immune responses. Co-stimulatory molecules include, but are not limited to, MHC class I molecules, TNF receptor proteins, immunoglobulin-like proteins, cytokine receptors, integrins, signaling lymphocyte activation molecules (SLAM proteins), activating NK cell receptors, OX40, CD40, GITR, 4-1BB (i.e., CD137), CD27, and CD28. In some embodiments, the "co-stimulatory molecule" is OX40, GITR, 4-1BB (i.e., CD137), CD27, and/or CD28.

The term "cytokine" is a generic term for proteins that are released by a cell population and act as intercellular mediators on another cell. Examples of such cytokines are lymphokines; monokines; interleukins (IL), such as IL-1, IL-1α, IL-2, IL-3, IL-4, IL-5, IL-6, IL-7, IL-8, IL-9, IL-11, IL-12, and IL-15; tumor necrosis factors, such as TNF-α or TNF-β; and other polypeptide factors, including LIF and kit ligands (KL) and γ-interferons. As used herein, the term "cytokine" includes proteins from natural sources or from recombinant cell cultures and biologically active equivalents of native sequence cytokines, including small molecule entities produced by artificial synthesis, and pharmaceutically acceptable derivatives and salts thereof.

An "immunoconjugate" is an antibody conjugated to one or more heterologous molecules, including but not limited to cytotoxic agents.

As used herein, the term "cytotoxic agent" refers to a substance that inhibits or prevents cell function and/or causes cell death or destruction. Cytotoxic agents include, but are not limited to, radioisotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$, and radioisotopes of Lu); chemotherapeutic agents or drugs (e.g., methotrexate, doxorubicin, vinca alkaloids (vincristine, vinblastine, and etoposide), doxorubicin, melphalan, mitomycin C, chlorambucil, zorubicin, or other intercalators); growth inhibitors; enzymes and fragments thereof such as nucleolytic enzymes; antibiotics; toxins such as small molecule toxins or enzymatic toxins of bacterial, fungal, plant or animal sources, including fragments and/or variants thereof; and various anti-tumor agents or anti-cancer agents disclosed below.

The "percent identity (%)" of an amino acid sequence refers to the percentage of amino acid residues in a candidate sequence that are the same as those of a specific amino acid sequence shown in this specification when aligning the candidate sequence with the specific amino acid sequence shown in this specification, with gaps introduced if necessary to achieve maximum percent sequence identity and without considering any conservative replacements as part of sequence identity.

For polypeptide sequences, "conservative modifications" include replacements of, deletions of, or additions to a polypeptide sequence that result in replacement of a certain amino acid with a chemically similar amino acid. Conservative replacement tables that provide functionally similar amino acids are well known in the art. Such conservatively modified variants are additional to polymorphic variants, interspecies homologs, and alleles of the present invention and do not exclude them. The following 8 groups comprise amino acids that are conservatively substituted with each other: 1) alanine (A) and glycine (G); 2) aspartic acid (D) and glutamic acid (E); 3) asparagine (N) and glutamine (Q); 4) arginine (R) and lysine (K); 5) isoleucine (I), leucine (L), methionine (M), and valine (V); 6) phenylalanine (F), tyrosine (Y), and tryptophan (W); 7) serine (S) and threonine (T); and 8) cysteine (C) and methionine (M) (see, for example, Creighton, *Proteins* (1984)). In some embodiments, the term "conservative sequence modification" is used to refer to an amino acid modification that does not significantly affect or alter the binding characteristics of an antibody comprising the amino acid sequence.

The term "N-terminus" refers to the most last amino acid at the N-terminus, and the term "C-terminus" refers to the most last amino acid at the C-terminus.

The term "host cell" refers to a cell into which an exogenous polynucleotide has been introduced, including progeny of such cells. Host cells include "transformants" and "transformed cells", which include primary transformed cells and progeny derived therefrom. Host cells are any type of cell systems that can be used to produce the antibody molecule of the present invention, including eukaryotic cells, e.g., mammalian cells, insect cells, and yeast cells; and prokaryotic cells, e.g., *E. coli* cells. Host cells include cultivated cells, as well as cells within a transgenic animal, a transgenic plant, or a cultivated plant tissue or an animal tissue.

The term "expression vector" refers to a vector comprising a recombinant polynucleotide, which comprises an expression control sequence operably linked to a nucleotide sequence to be expressed. Expression vectors contain sufficient cis-regulatory elements for expression, and other elements for expression can be provided by a host cell or in an in vitro expression system. Expression vectors include all those known in the art, including cosmids, plasmids (e.g., naked or contained in liposomes), and viruses (e.g., lentiviruses, retroviruses, adenoviruses and adeno-associated viruses) incorporated into recombinant polynucleotides.

The terms "individual" and "subject" can be used interchangeably and refer to a mammal. Mammals include, but are not limited to, domesticated animals (e.g., cows, sheep, cats, dogs, and horses), primates (e.g., human and non-human primates such as monkeys), rabbits and rodents (e.g., mice and rats). In particular, individuals are humans.

The term "treatment" refers to a clinical intervention intended to alter the natural progress of the disease in an individual being treated. Desired therapeutic effects include, but are not limited to, preventing the occurrence or recurrence of diseases, alleviating symptoms, reducing any direct or indirect pathological outcomes of diseases, preventing metastasis, delaying disease progression, improving or alleviating conditions, and improving prognosis. In some embodiments, the antibody molecule of the present invention is used to delay the progression of a disease or to slow the progression of a disease.

The term "anti-tumor effect" refers to a biological effect that can be demonstrated by a variety of means, including but not limited to, for example, a decrease in tumor volume, a decrease in number of tumor cells, a decrease in tumor cell proliferation, or a decrease in tumor cell viability. The terms "tumor" and "cancer" are used interchangeably herein and encompass solid and liquid tumors.

The terms "cancer" and "cancerous" refer to or describe a physiological disease in mammals that is typically characterized by unregulated cell growth. Examples of cancers include, but are not limited to, carcinomas, lymphomas, blastomas, sarcomas, and leukemias or lymphoid malignancies. More specific examples of such cancers include, but are not limited to, squamous cell carcinoma (e.g., epithelial squamous cell carcinoma), lung cancer (including small cell lung cancer, non-small cell lung cancer, lung adenocarcinoma, and squamous cell lung cancer), peritoneal cancer, hepatocellular carcinoma, gastric cancer (including gastrointestinal cancer and gastrointestinal stromal cancer), pancreatic cancer, glioblastoma, cervical cancer, ovarian cancer, liver cancer, bladder cancer, urinary tract cancer, liver tumor, breast cancer, colon cancer, rectal cancer, colorectal cancer, endometrial or uterine cancer, salivary gland cancer, kidney cancer, prostate cancer, vulval cancer, thyroid cancer, liver cancer, anal cancer, penile cancer, melanoma, superficial spreading melanoma, lentigo maligna melanoma, acral melanoma, nodular melanoma, multiple myeloma and B-cell lymphoma, chronic lymphocytic leukemia (CLL), acute lymphoblastic leukemia (ALL), hairy cell leukemia, chronic myelogenous leukemia, and post-transplant lymphoproliferative disorder (PTLD), as well as abnormal vascular proliferation associated with phakomatoses, edema (such as those associated with brain tumors), and Meigs syndrome, brain tumor and brain cancer, and head and neck cancer, and related metastases. In certain embodiments, cancers suitable for treatment with the antibody of the present invention include lung cancer (e.g., non-small cell lung cancer), liver cancer, gastric cancer, or colon cancer, including metastatic forms of such cancers.

The term "tumor" refers to all neoplastic cell growth and proliferation regardless of whether malignant or benign, and all pre-cancerous and cancerous cells and tissues. The terms "cancer", "cancerous" and "tumor" are not mutually exclusive when referred to herein.

The term "infectious disease" refers to a disease caused by a pathogen, and includes, for example, a viral infection, a bacterial infection, a parasitic infection, or a fungal infection.

II. Antibody Molecule of the Present Invention

The present invention provides a novel antibody molecule that can be used for immunotherapy, prevention and/or diagnosis of a variety of diseases. The antibody molecule of the present invention comprises at least 4 antigen-binding sites, and can function as a monospecific antibody or a multispecific (e.g., bispecific) antibody, and preferably, function as a multispecific (e.g., bispecific) antibody.

In the generation of monospecific or multispecific (e.g., bispecific) antibodies with multiple polypeptide chains, problems such as undesired inter-chain mispairing, decreased antibody affinity, and decreased stability often occur. The antibody molecule constructed herein can avoid these common problems.

The antibody molecule platform constructed in the application comprises: (i) single-domain antigen-binding sites; (ii) antigen-binding Fab fragments, wherein the single-domain antigen-binding site is located at the N-terminus of a light chain variable domain (VL) of the antigen-binding Fab fragment or the C-terminus of a light chain constant region (CL) of the antigen-binding Fab fragment or the single-domain antigen-binding site is located at the N-terminus of a heavy chain variable domain (VH) or the C-terminus of an immunoglobulin CH1 domain of the antigen-binding Fab fragment, the single-domain antigen-binding site and the antigen-binding Fab fragment bind to the same antigen or different antigens, and the single-domain antigen-binding site and the antigen-binding Fab fragment have or do not have a linker peptide therebetween; and (iii) immunoglobulin Fc domains located at the C-terminus of the single-domain antigen-binding site or the antigen-binding Fab fragment.

In one embodiment, the antibody molecule of the present invention has 4 polypeptide chains, including 2 single-domain antigen-binding sites and 2 Fab fragments, and an Fc region.

In another embodiment, the single-domain antigen-binding sites and the Fab fragments of the antibody molecule of the present invention do not have a linker peptide therebetween.

In yet another embodiment, the single-domain antigen-binding sites and the Fab fragments of the antibody molecule of the present invention have a linker peptide therebetween. The type of the linker peptide is not particularly limited. In embodiments, the linker peptide is a peptide having an amino acid sequence of 1 to 100, particularly 1 to 50, more particularly 1 to 20 amino acids in length. In some embodiments, the linker peptide is (G×S)n or (G×S)nGm, wherein G is glycine, S is serine, x is any integer from 1 to 4, n is any integer from 1 to 7, and m is any integer from 0 to 3. In one specific embodiment, the linker peptide is $(G_4S)_2$ (SEQ ID NO: 9).

The single-domain antigen-binding sites of the antibody molecule of the present invention are a single variable domain capable of specifically binding to a target antigen epitope with high binding affinity, e.g., heavy chain variable domain (VH), light chain variable domain (VL), heavy chain variable domain derived from Camelidae heavy chain antibodies, v-NAR of IgNAR from sharks, camelized human VH domain, humanized Camelidae antibody heavy chain variable domain, and recombinant single domain thereof. In one embodiment, the single-domain antigen-binding sites of the antibody molecule of the present invention are heavy chain variable domains derived from a Camelidae heavy chain antibody, camelized human VH domains and/or humanized Camelidae antibody heavy chain variable domains.

The size, structure, and antigenicity in human subjects of antibodies obtained from Camelidae species (such as camel, alpaca, dromedary, llama, and guanaco) have been characterized in the prior art. Certain natural IgG antibodies from the Camelidae lack light chains and are therefore structurally different from common four-chain antibody structures with two heavy and two light chains in other animals. See PCT/EP 93/02214 (WO94/04678 published on Mar. 3, 1994).

A heavy chain variable domain (also referred to as VHH) of a Camelidae heavy-chain antibody that has high affinity to target antigens can be obtained by genetic engineering processes. See U.S. Pat. No. 5,759,808 issued on Jun. 2, 1998. Similar to other non-humanized antibody fragments, amino acid sequences of Camelidae VHHs can be altered recombinantly to obtain sequences that more closely mimic a human sequence, i.e., "humanized", thereby reducing the antigenicity of the Camelidae VHHs for humans. In addition, key elements derived from Camelidae VHHs can also be transferred to human VH domains to obtain camelized human VH domains. In one embodiment of the present invention, the single-domain antigen-binding sites of the antibody molecule of the present invention are humanized VHHs directed against PD-L1, which have an amino acid sequence set forth in SEQ ID NO: 1 and/or SEQ ID NO: 2. In another embodiment of the present invention, the single-domain antigen-binding sites of the antibody molecule of the present invention are VHHs directed against GITR, which have an amino acid sequence set forth in SEQ ID NO: 24.

A VHH has a molecular weight that is one-tenth the molecular weight of a human IgG molecule, and has a physical diameter of only a few nanometers. A VHH itself has extremely high thermal stability, stability against extreme pH and protease digestion, and low antigenicity. Therefore, in one embodiment of the antibody molecule of the present invention, a VHH is included as a building block, contributing to the stability of the antibody molecule of the present invention and to the low antigenicity in human subjects.

The Fab fragments of the antibody molecule of the present invention can specifically bind to a target antigen epitope with relatively high binding affinity. In one embodiment, the Fab fragments are immunoglobulin Fab fragments, comprising a peptide consisting of an immunoglobulin light chain variable region (VL) and an immunoglobulin light chain constant region (CL) and a peptide consisting of an immunoglobulin heavy chain variable region (VH) and an immunoglobulin heavy chain constant region 1 (CH1), wherein the CL region and the CH1 region are optionally covalently linked by a disulfide bond, thus heterodimerizing the Fab fragments. In another embodiment, the Fab fragments are Fab fragments where the light chain variable region (VL) of an immunoglobulin Fab fragment and the heavy chain variable region (VH) of an immunoglobulin Fab fragment are exchanged, comprising a peptide consisting of an immunoglobulin light chain variable region (VL) and an immunoglobulin heavy chain constant region (CH1) and a peptide consisting of an immunoglobulin heavy chain variable region (VH) and an immunoglobulin light chain constant region (CL), wherein the CL region and the CH1 region are optionally covalently linked by a disulfide bond, thus heterodimerizing the Fab fragments. In yet another embodiment, the Fab fragments are Fab fragments where the light chain constant region (CL) of an immunoglobulin Fab fragment and the heavy chain constant region (CH1) of an immunoglobulin Fab fragment are exchanged, comprising a peptide consisting of an immunoglobulin heavy chain variable region (VH) and an immunoglobulin light chain constant region (CL) and a peptide consisting of an immunoglobulin light chain variable region (VL) and an immunoglobulin heavy chain constant region (CH1), wherein the CL region and the CH1 region are optionally covalently linked by a disulfide bond, thus heterodimerizing the Fab fragments.

As will be appreciated by those skilled in the art, the disulfide bond between the CL region and the CH1 region of a Fab fragment is preferred, but not essential for functioning (Orcutt K D et al., *A modular IgG-scFv bispecific antibody topology, Protein Eng Des Sel.* 2010, 23(4):221-228). Thus, in some embodiments, the Fab fragments of the antibody molecule of the present invention do not comprise a disulfide bond. In this regard, the two chains of a Fab fragment may be engineered in such a way as to interact stably without a disulfide bond. For example, in some embodiments, the two chains of a Fab fragment may be engineered to remove cysteine residues, while still interacting stably and functioning as Fab. In one embodiment, the two chains of a Fab fragment are mutated to promote stable interactions therebetween. For example, the "knob-in-hole" genetic engineering strategy (see, e.g., John B. B. Ridgway et al., *Knobs-into-holes' engineering of antibody CH3 domains for heavy chain heterodimerization. Protein Engineering,* 1996. 9(7): p. 617-21; Shane Atwell et al., *Stable heterodimers for remodeling the domain interface of a homodimer using a phage display library. J. mol. biol.,* 1997.270: p. 26-35) can be used to promote heterodimerization between the two chains of a Fab fragment. Using this strategy, a "knob" structure is created by replacing a small amino acid side chain with a large amino acid side chain at an interface between interacting domains. Accordingly, a "hole" structure is created by replacing a large side chain with a small side chain at an interface between interacting molecules. Thus, also contemplated for use herein is designing variant Fab fragments for specific purposes, e.g., amino acid alterations in a constant domain (CH1 and/or CL), removal of disulfide bonds, etc.

In some embodiments, the Fab fragments of the antibody molecule of the present invention are derived from monoclonal antibodies and may be derived from any type of antibodies, including IgA, IgM, IgD, IgG, IgE and subtypes thereof, e.g., IgG1, IgG2, IgG3 and IgG4. A light chain domain may be derived from a κ chain or a λ chain. In addition, the Fab fragments used herein can also be prepared by recombinant means. In some embodiments, the CH1 domain and the CL domain in the Fab fragments of the antibody molecule of the present invention are both from a corresponding portion of a human immunoglobulin, or have a sequence substantially identical (e.g., having at least 80%, 85%, 90%, 92%, 95%, 97%, 98%, 99% or higher identity) thereto.

The immunoglobulin Fc domain of the antibody molecule of the present invention is capable of extending the in vivo half-life of the antibody of the present invention and providing effector functions. See, for example, International Publication No. WO98/23289; international publication No. WO97/34631; and U.S. Pat. No. 6,277,375.

In one specific embodiment, the Fc domains of the second polypeptide chain and the fourth polypeptide chain of the antibody molecule of the present invention each comprise a hinge region having "CPPC" amino acid residues (SEQ ID NO: 32), and/or respectively comprise Y349C and S354C (according to the Kabat EU numbering system), whereby the second polypeptide chain and the fourth polypeptide chain of the antibody molecule of the present invention form inter-chain disulfide bonds in the Fc domains, which promotes the correct pairing of the second polypeptide chain and the fourth polypeptide chain of the antibody molecule of the present invention.

In one embodiment, the "knob-in-hole" technique is also employed for the immunoglobulin Fc domain of the antibody molecule of the present invention, which enables the modification of interfaces between different chains of the antibody molecule of the present invention, thus facilitating the correct association of each chain of the antibody molecule of the present invention. Generally, this technique involves introducing a "protuberance" at the interface of one chain, and introducing a corresponding "cavity" at the interface of the other chain to be paired with, such that the protuberance can be placed at the cavity. A first preferred interface comprises the CH3 domain from the heavy chain constant domains of one chain and the CH3 domain from the heavy chain constant domains of the other chain to be paired with. The protuberance can be constructed by replacing small amino acid side chains at an interface of the CH3 domain from the heavy chain constant domains of one chain with large side chains, such as tyrosine or tryptophan. The compensating cavity of the same size as, or a similar size to, the protuberance is constructed at an interface of the CH3 domain from the heavy chain constant domains of the other chain to be paired with, by replacing large amino acid side chains with small side chains, such as alanine or threonine. A second preferred interface consists of a light chain CL domain and a heavy chain CH1 domain of the Fab fragment mentioned above, and the correct heterodimerization between the two chains of the Fab fragment is promoted by constructing a protuberance-cavity interaction.

In one embodiment, the Fc region of the antibody molecule of the present invention comprises a modification of the binding affinity to an Fc receptor. In one embodiment, the Fc receptor is an Fcγ receptor, in particular a human Fcγ receptor. In one embodiment, the Fc receptor is an activating Fc receptor. In one embodiment, the modification reduces an effector function of the antibody molecule of the present invention. In one specific embodiment, the effector function is antibody-dependent cell-mediated cytotoxicity (ADCC). In one embodiment, the modification is in the Fc region of the immunoglobulin molecule, particularly in the CH2 region. In one embodiment, the immunoglobulin molecule comprises an amino acid replacement at position 329 (EU numbering) of an immunoglobulin heavy chain. In one specific embodiment, the amino acid replacement is P329G. In one embodiment, the antibody molecule of the present invention comprises amino acid replacements at positions 234 and 235 (EU numbering) of an immunoglobulin heavy chain. In one specific embodiment, the amino acid replacements are L234A and L235A (LALA mutations) (Armour K L et al., *Recombinant human IgG molecules lacking Fcgamma receptor I binding and monocyte triggering activities, Eur. J. Immunol.*, 1999, 29(8):2613-24). In one embodiment, the antibody molecule of the present invention comprises amino acid replacements at positions 234, 235 and 329 (EU numbering) of an immunoglobulin heavy chain. In one specific embodiment, the immunoglobulin molecule comprises amino acid replacements L234A, L235A, and P329G (EU numbering) of an immunoglobulin heavy chain.

At least one single-domain antigen-binding site (e.g., two single-domain antigen-binding sites) and at least one Fab fragment of the antibody molecule of the present invention are capable of specifically binding to at least one antigen. Preferably, the antibody molecule of the present invention binds to two or more antigens, whereby the antibody molecule of the present invention is a multispecific antibody molecule, e.g., a bispecific antibody molecule. The antigens include, but are not limited to, cytokines, growth factors, hormones, signaling proteins, inflammatory mediators, ligands, cell surface receptors, or fragments thereof.

In some embodiments, the antibody molecule of the present invention inhibits signaling pathways of multiple (e.g., two) immune checkpoint molecules; e.g., the antibody molecule of the present invention is a bispecific antibody molecule with a first binding specificity for PD-L1 and a second binding specificity for TIM-3, LAG-3, PD-1, or PD-L2, and functions by inhibiting signaling pathways of the immune checkpoint molecules.

In some embodiments, the antibody molecule of the present invention inhibits signaling pathways of immune checkpoint molecules and agonizes signaling pathways of co-stimulatory molecules; e.g., the antibody molecule of the present invention is a bispecific antibody molecule with a first binding specificity for PD-L1, TIM-3, LAG-3, PD-1, or PD-L2 and a second binding specificity for OX40, GITR, 4-1BB, CD27, or CD28, and functions by inhibiting signaling pathways of the immune checkpoint molecules and agonizing signaling pathways of the co-stimulatory molecules.

In some embodiments, the antibody molecule of the present invention inhibits signaling pathways of immune checkpoint molecules and inhibits aberrant angiogenesis; e.g., the antibody molecule of the present invention is a bispecific antibody molecule with a first binding specificity for PD-L1, TIM-3, LAG-3, PD-1, or PD-L2 and a second binding specificity for VEGF or VEGF receptors, and functions by inhibiting signaling pathways of the immune checkpoint molecules and inhibiting signaling pathways of the VEGF and VEGF receptors.

In some embodiments, the antibody molecule of the present invention agonizes signaling pathways of multiple (e.g., two) co-stimulatory molecules; e.g., the antibody molecule of the present invention is a bispecific antibody molecule with a first binding specificity for OX40 and a second binding specificity for GITR, 4-1BB, CD27, or CD28, and functions by agonizing signaling pathways of the co-stimulatory molecules.

In some embodiments, the antibody molecule of the present invention agonizes signaling pathways of co-stimulatory molecules and inhibits aberrant angiogenesis; e.g., the antibody molecule of the present invention is a bispecific antibody molecule with a first binding specificity for OX40, GITR, 4-1BB, CD27, or CD28 and a second binding specificity for VEGF or VEGF receptors, and functions by agonizing signaling pathways of the co-stimulatory molecules and inhibiting signaling pathways of the VEGF and VEGF receptors.

In some embodiments, the antibody molecule of the present invention inhibits aberrant angiogenesis, inhibits signaling pathways of immune checkpoint molecules, and agonizes signaling pathways of co-stimulatory molecules; e.g., the antibody molecule of the present invention is a trispecific antibody molecule with a first binding specificity for VEGF or VEGF receptors, a second binding specificity for PD-L1, TIM-3, LAG-3, PD-1, or PD-L2, and a third binding specificity for OX40, GITR, 4-1BB, CD27, or CD28, and functions by inhibiting signaling pathways of the VEGF and VEGF receptors, inhibiting signaling pathways of the immune checkpoint molecules and agonizing signaling pathways of the co-stimulatory molecules.

In some embodiments, the antibody molecule of the present invention has any of the structures illustrated in FIGS. 1A-1D of this specification.

As shown in the schematic diagram in FIG. 1A, an exemplary antibody molecule of the present invention is a four-chain antibody molecule comprising 2 Fab fragments, single-domain antigen-binding sites located at the C-terminus of each Fab fragment light chain constant region (CL), and an immunoglobulin Fc domain as the C-terminus of the antibody molecule of the present invention, wherein there is or isn't a linker peptide between the C-terminus of the Fab fragment light chain constant region (CL) and the single-domain antigen-binding sites.

Figure 1B:
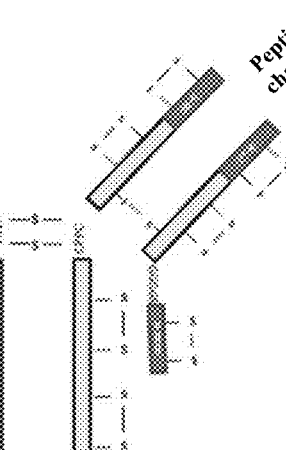

As shown in the schematic diagram in FIG. 1B, an exemplary antibody molecule of the present invention is a four-chain antibody molecule comprising 2 Fab fragments, single-domain antigen-binding sites located at the N-terminus of each Fab fragment light chain variable domain (VL), and an immunoglobulin Fc domain as the C-terminus of the antibody molecule of the present invention, wherein there is or isn't a linker peptide between the N-terminus of the Fab fragment light chain variable domain (VL) and the single-domain antigen-binding sites.

Figure 1C:
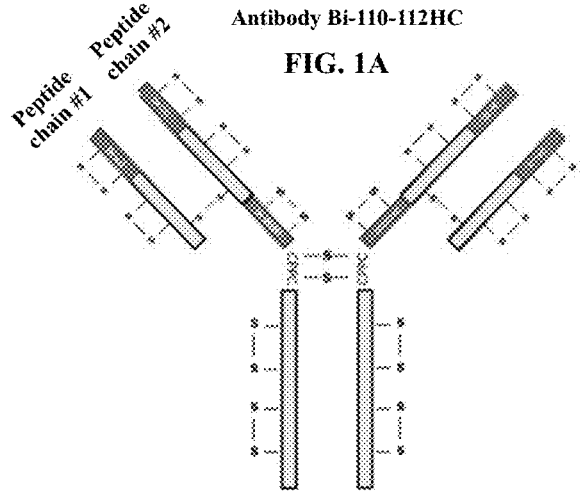

As shown in the schematic diagram in FIG. 1C, an exemplary antibody molecule of the present invention is a four-chain antibody molecule comprising 2 Fab fragments, single-domain antigen-binding sites located at the C-terminus of each Fab fragment CH1 domain, and an immunoglobulin Fc domain as the C-terminus of the antibody molecule of the present invention, wherein there is or isn't a linker peptide between the C-terminus of the Fab fragment CH1 domain and the single-domain antigen-binding sites.

Figure 1D:
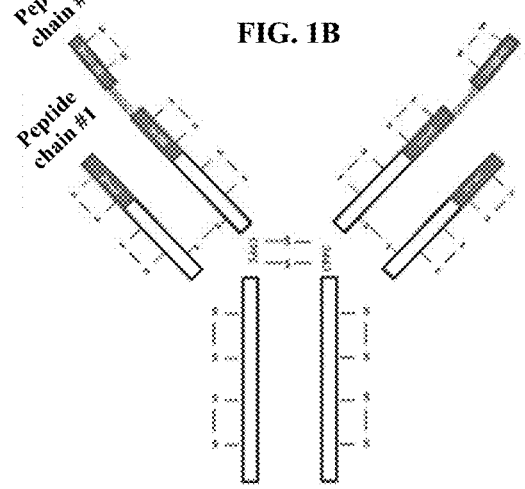
Figure 2A:
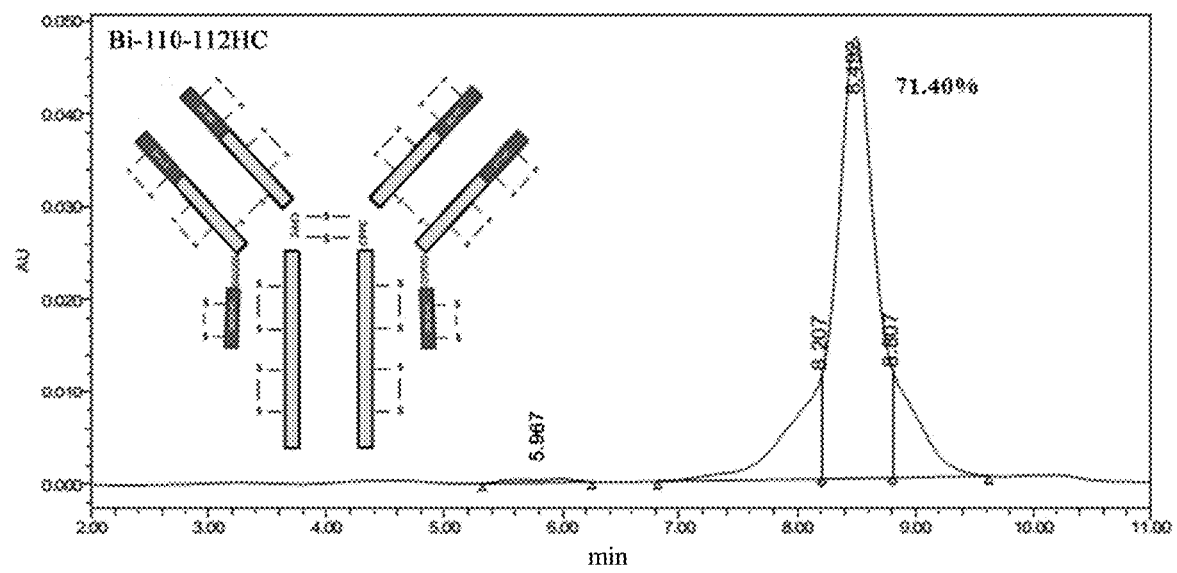
FIGS. 2A-2D respectively show the purity detected by size exclusion chromatography (SEC) of 4 structures of anti-OX40/PD-L1 bispecific antibodies Bi-110-112HC, Bi-113-112HC, Bi-119-112LC and Bi-122-112LC prepared herein. The hinge region comprises the amino acid sequence "CPPC" (SEQ ID NO: 32).
Figure 2B:
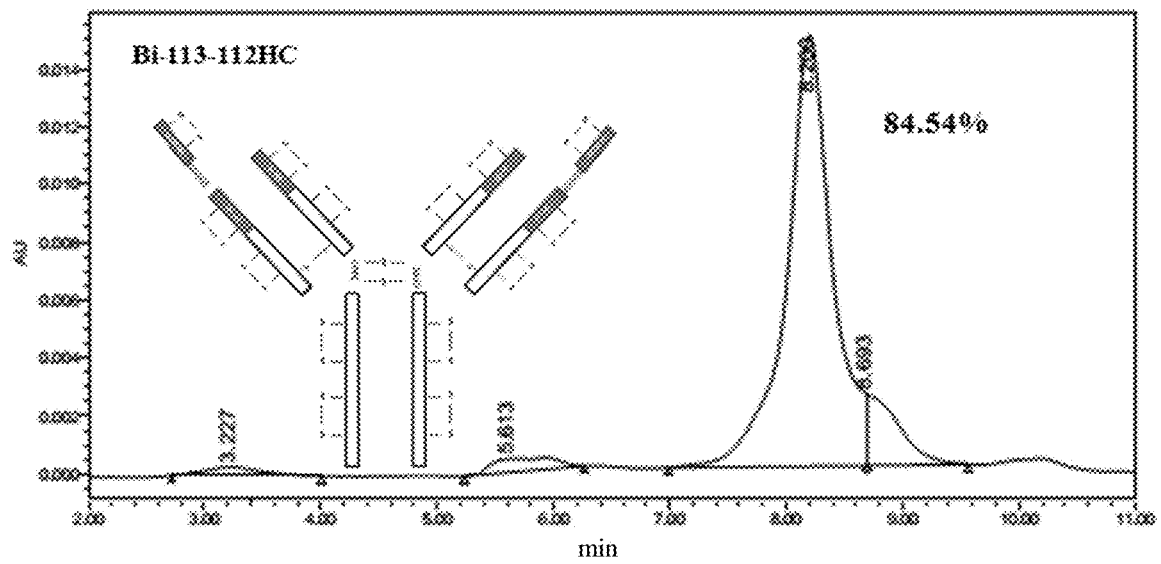
Figure 2C:
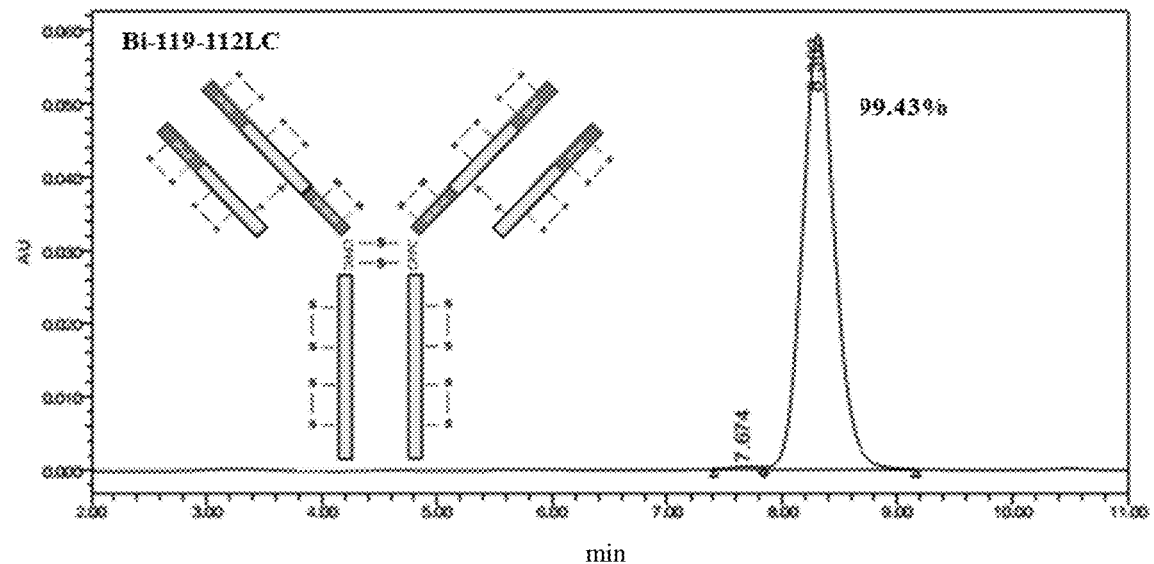
Figure 2D:
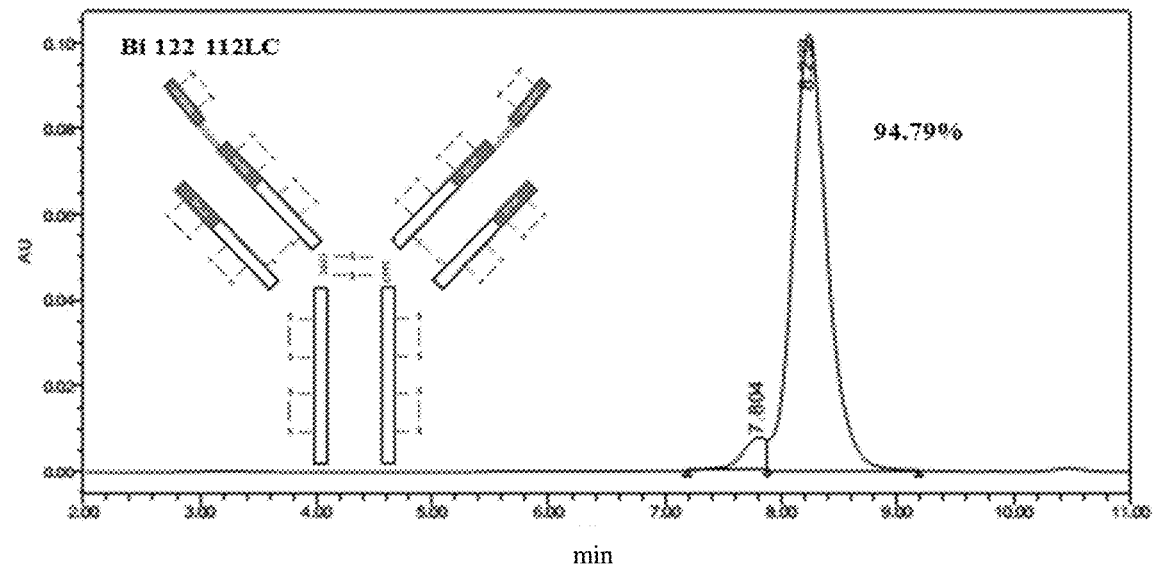

As shown in the schematic diagram in FIG. 1D, an exemplary antibody molecule of the present invention is a four-chain antibody molecule comprising 2 Fab fragments, single-domain antigen-binding sites located at the N-terminus of each Fab fragment heavy chain variable domain (VH), and an immunoglobulin Fc domain as the C-terminus of the antibody molecule of the present invention, wherein there is or isn't a linker peptide between the N-terminus of the Fab fragment heavy chain variable domain (VH) and the single-domain antigen-binding sites.

The following are examples of the antibody molecule of the present invention and regulatory effects of the antibody molecule of the present invention on signaling pathways where an antigen to which the antibody molecule specifically binds is involved.

i) In one embodiment, the antibody molecule of the present invention is an anti-OX40/PD-L1 bispecific antibody or a multispecific antibody.

OX40 (also known as CD134, TNFRSF4 and ACT35) is a cell surface glycoprotein, and a member of the tumor necrosis factor (TNF) receptor superfamily. OX40 is expressed on T lymphocytes and provides co-stimulatory signals for the proliferation and survival of activated T cells. OX40 was initially described as a T cell activation marker on rat CD4 T cells (Paterson D J et al., *Antigens of activated rat T lymphocytes including a molecule of 50,000 Mr detected only on CD4 positive T blasts. Mol Immunol.* 1987; 24:1281-1290) and was subsequently shown to be up-regulated upon TCR engagement (Mallett S. et al., *Characterization of the MRC OX40 antigen of activated CD4 positive T lymphocytes-a molecule related to nerve growth factor receptor. EMBO J.* 1990; 9:1063-1068). OX40 has been identified on CD4+ T cells, CD8+ T cells, NK cells, NKT cells and neutrophilic granulocytes (Paterson D. J. et al., *Antigens of activated Rat T lymphocytes including a molecule of 50,000 M(r) detected only on CD4 positive T blasts, Molecular Immunology,* 1987, 24(12):1281-1290). OX40 signaling can promote co-stimulatory signals to T cells, leading to enhanced cell proliferation, survival, effector function, and migration (Gramaglia I et al., *OX40 ligand: a potent costimulatory molecule for sustaining primary CD4 T cell responses. J Immunol.* 1998; 161:6510-6517; Gramaglia I et al., *The OX40 costimulatory receptor determines the development of CD4 memory by regulating primary clonal expansion. J Immunol.* 2000; 165:3043-3050).

An anti-OX40 antibody functioning as an OX40 agonist is disclosed in the prior art. For example, WO2012/027328 discloses amino acid sequences of heavy and light chain variable regions of the anti-OX40 antibody mAb 106-222 and humanized 106-222 (Hu106), and amino acid sequences of heavy and light chain variable regions of the anti-OX40 antibody mAb 119-122 and humanized 119-122 (Hu119). An anti-OX40 antibody functioning as an OX40 agonist is also disclosed in U.S. Pat. No. 7,959,925, PCT Publication No. WO2006/121810, and Chinese Patent Application No. 201710185399.9. The anti-OX40 antibody is capable of activating OX40, thereby inducing the proliferation of effector T lymphocytes and promoting an immune response to tumor cells expressing a tumor-associated antigen (TAA).

PD-L1, also known as cluster of differentiation 274 (CD274) or B7 homolog 1 (B7-H1), is a 40-kDa type I transmembrane protein. PD-L1 binds to the receptor PD-1 thereof present on activated T cells and down-regulates T cell activation (Latchman et al., 2001, *Nat. Immunol.,* 2:261-8; Carter et al., 2002, *Eur. J. Immunol.,* 32:634-43). PD-L1 expression has been found in many cancers, including human lung cancer, ovarian cancer, colon cancer, and multiple myelomas, and PD-L1 expression is often associated with poor prognosis of cancers (Iwai et al., (2002) *PNAS*, 99:12293-7; Ohigashi et al., (2005) *Clin Cancer Res.*, 11:2947-53; Okazaki et al., (2007) *Intern. Immun.*, 19:813-24; Thompson et al., (2006) *Cancer Res.*, 66:3381-5). It has been proposed that, in some patients with tumors, immunosuppression can be reversed by suppressing local interactions between PD1 and PD-L1.

The anti-PD-L1 antibody Atezolizumab developed by Roche, the anti-PD-L1 antibody Avelumab jointly developed by Merck KGaA and Pfizer, and Durvalumab developed by AstraZeneca have shown their efficacy in treating some patients with tumors. Other anti-PD-L1 antibodies include YW243.55.570 (the heavy and light chain variable regions are set forth in SEQ ID NOs: 20 and 21 in WO2010/077634), the anti-PD-L1 antibody disclosed in WO2007/005874, and so on.

The anti-OX40/PD-L1 bispecific antibody or multispecific antibody of the present invention targets at least OX40 and PD-L1 simultaneously. The Fab fragments and single-domain antigen-binding sites thereof respectively bind to OX40 and PD-L1 molecules or vice versa, thus blocking inhibitory PD-1/PD-L1 signaling pathways and activating OX40/OX40 ligand signaling pathways in T cells and natural killer (NK) cells, and promoting immune responses to diseases.

In one embodiment, the antibody molecule of the present invention comprises single-domain antigen-binding sites specifically binding to PD-L1 and Fab fragments specifically binding to OX40. In one embodiment, the antibody molecule of the present invention comprises single-domain antigen-binding sites specifically binding to OX40 and Fab fragments specifically binding to PD-L1.

The Fab fragments specifically binding to PD-L1 or OX40 comprise 6 CDRs derived from VH/VL pairs of an anti-PD-L1 antibody reported in any prior art (e.g., the anti-PD-L1 antibody exemplified above) and VH/VL pairs of anti-PD-L1 antibodies developed in the future, or sequences having one, two, three, four, five, six or more amino acid alterations (e.g., amino acid replacements or deletions) compared to one or more of the 6 CDRs; or comprise 6 CDRs derived from VH/VL pairs of an anti-OX40 antibody reported in any prior art (e.g., the anti-OX40 antibody exemplified above) and VH/VL pairs of anti-OX40 antibodies developed in the future, or sequences having one, two, three, four, five, six or more amino acid alterations (e.g., amino acid replacements or deletions) compared to one or more of the 6 CDRs. In one embodiment, the anti-OX40 antibody is ADI-20112, which has a heavy chain amino acid sequence set forth in SEQ ID NO: 10 and a light chain amino acid sequence set forth in SEQ ID NO: 15.

The single-domain antigen-binding sites specifically binding to PD-L1 or OX40 comprise heavy chain variable domains (VHs), light chain variable domains (VLs), heavy chain variable domains of antibodies from Camelidae serum that are naturally free of light chain and composed of only two heavy chains, VH-like single domains of IgNAR from sharks, camelized human VH domains, and humanized Camelidae antibody heavy chain variable domains specifically binding to PD-L1 or OX40.

In one embodiment, the anti-OX40/PD-L1 bispecific antibody of the present invention comprises two Fab fragments specifically binding to OX40 and two single-domain antigen-binding sites (e.g., VHHs) specifically binding to PD-L1, each having any of the structures illustrated in FIGS. 1A-1D. The two Fab fragments specifically binding to OX40 specifically bind to the same epitope or different epitopes on OX40 molecules, and the two single-domain antigen-binding sites specifically binding to PD-L1 specifically bind to the same epitope or different epitopes on PD-L1 molecules.

In one embodiment, the Fab fragments specifically binding to OX40 in the anti-OX40/PD-L1 bispecific antibody of the present invention comprise all the 6 heavy chain complementarity determining regions (CDRs) and light chain CDRs in the paired heavy chain and light chain variable region sequences derived from the anti-OX40 antibody ADI-20112 set forth in SEQ ID NOs: 11 and 7, or sequences having one, two, three, four, five, six or more amino acid alterations (e.g., amino acid replacements or deletions) compared to one or more of the 6 CDRs.

In one embodiment, the Fab fragments specifically binding to OX40 in the anti-OX40/PD-L1 bispecific antibody of the present invention comprise the paired heavy chain and light chain variable region sequences derived from the anti-OX40 antibody ADI-20112 set forth in SEQ ID NOs: 11 and 7, or sequences having at least 90%, 91%, 92%, 93%, 94%, 95%, 96%, 97%, 98%, 99% or higher sequence identity compared to the paired heavy chain and light chain variable region sequences.

In one embodiment, the single-domain antigen-binding sites specifically binding to PD-L1 in the anti-OX40/PD-L1 bispecific antibody of the present invention comprise a CDR1 set forth in SEQ ID NO: 3, a CDR2 set forth in SEQ ID NO: 4, and a CDR3 set forth in SEQ ID NO: 5, or sequences having one, two, three, four, five, six or more amino acid alterations (e.g., amino acid replacements or deletions) compared to one or more of the 3 CDRs.

In another embodiment, the single-domain antigen-binding sites specifically binding to PD-L1 in the anti-OX40/PD-L1 bispecific antibody of the present invention comprise an amino acid sequence set forth in SEQ ID NO: 1 and/or SEQ ID NO: 2, or sequences substantially identical (e.g., having at least 80%, 85%, 90%, 92%, 95%, 97%, 98%, 99% or higher identity) thereto.

The CH1 domain and Fc region (comprising the CH2 domain, CH3 domain, and optionally, CH4 domain) in heavy chain constant regions of the anti-OX40/PD-L1 bispecific antibody of the present invention are not specifically restricted in type, and are preferably corresponding domains derived from heavy chain constant regions of IgG1, IgG2 or IgG4 or sequences substantially identical (e.g., having at least 80%, 85%, 90%, 92%, 95%, 97%, 98%, 99% or higher identity) thereto. More preferably, the CH1 domain and Fc region in the heavy chain constant regions are derived from the CH1 domain and Fc region in heavy chain constant regions of human IgG1, or sequences substantially identical (e.g., having at least 80%, 85%, 90%, 92%, 95%, 97%, 98%, 99% or higher identity) thereto.

In one embodiment, the anti-OX40/PD-L1 bispecific antibody of the present invention comprises the CH1 domain and Fc region in heavy chain constant regions of IgG4 (e.g., human IgG4). In one embodiment, the anti-OX40/PD-L1 bispecific antibody of the present invention comprises the CH1 domain and Fc region in heavy chain constant regions of IgG1 (e.g., human IgG1). In another embodiment, the anti-OX40/PD-L1 bispecific antibody of the present invention comprises the CH1 domain in heavy chain constant regions of IgG4 (e.g., human IgG4) and the Fc region in heavy chain constant regions of IgG1 (e.g., human IgG1), or comprises the CH1 domain in heavy chain constant regions of IgG1 (e.g., human IgG1) and the Fc region in heavy chain constant regions of IgG4 (e.g., human IgG4).

In one embodiment, the Fc domains of the second polypeptide chain and the fourth polypeptide chain of the anti- OX40/PD-L1 bispecific antibody of the present invention each comprise a hinge region having "CPPC" amino acid residues (SEQ ID NO: 32), and/or respectively comprise Y349C and S354C (according to the Kabat EU numbering system), whereby the second polypeptide chain and the fourth polypeptide chain of the anti-OX40/PD-L1 bispecific antibody of the present invention form inter-chain disulfide bonds in the Fc domains, which stabilizes the correct pairing of the second polypeptide chain and the fourth polypeptide chain.

In one embodiment, the Fc domains of the second polypeptide chain and/or the fourth polypeptide chain of the anti-OX40/PD-L1 bispecific antibody of the present invention comprise an amino acid mutation which affects antibody effector functions. In one specific embodiment, the amino acid replacement is LALA mutation.

In another embodiment, the anti-OX40/PD-L1 bispecific antibody of the present invention comprises a κ light chain constant region and/or a λ light chain constant region, e.g., a human κ light chain constant region and/or a human λ light chain constant region. In one embodiment, the light chain constant regions comprise an amino acid sequence set forth in SEQ ID NO: 8, or sequences substantially identical (e.g., having at least 80%, 85%, 90%, 92%, 95%, 97%, 98%, 99% or higher identity) thereto.

In one embodiment, the Fc domains of the second polypeptide chain and the fourth polypeptide chain of the anti-OX40/PD-L1 bispecific antibody of the present invention each comprise a stable association of "knob-in-hole". In one embodiment, the amino acid replacement T366W is contained in one of the second polypeptide chain and the fourth polypeptide chain, and the amino acid replacements T366S, L368A, and Y407V (EU numbering) are contained in the other one of the second polypeptide chain and the fourth polypeptide chain. Thereby the protuberance in one chain can be placed at the cavity in the other chain, which facilitates the correct pairing of the second polypeptide chain and the fourth polypeptide chain.

In one embodiment, the immunoglobulin CH1 domain and CL domain of the anti-OX40/PD-L1 bispecific antibody of the present invention respectively comprise a protuberance and a cavity, or vice versa, and the protuberance or cavity in the CH1 domain can be respectively placed at the cavity or protuberance in the CL domain, such that the first polypeptide chain and the second polypeptide chain of the anti-OX40/PD-L1 bispecific antibody of the present invention also form a stable association of "knob-in-hole" with each other.

In a specific embodiment, the anti-OX40/PD-L1 bispecific antibody of the present invention consists of 4 polypeptide chains that are substantially bilaterally symmetrical, wherein the 2 polypeptide chains in the left half of the antibody molecule comprise a first polypeptide chain set forth in SEQ ID NO: 6 and a second polypeptide chain set forth in SEQ ID NO: 10, respectively, or a first polypeptide chain set forth in SEQ ID NO: 14 and a second polypeptide chain set forth in SEQ ID NO: 10, respectively, or a first polypeptide chain set forth in SEQ ID NO: 15 and a second polypeptide chain set forth in SEQ ID NO: 16, respectively, or a first polypeptide chain set forth in SEQ ID NO: 15 and a second polypeptide chain set forth in SEQ ID NO: 17, respectively, or sequences substantially identical (e.g., having at least 80%, 85%, 90%, 92%, 95%, 97%, 98%, 99% or higher identity) to any one of the sequences; accordingly, the 2 polypeptide chains in the right half of the antibody molecule comprise a third polypeptide chain set forth in SEQ ID No: 6 and a fourth polypeptide chain set forth in SEQ ID No: 10, respectively, or a third polypeptide chain set forth in SEQ ID NO: 14 and a fourth polypeptide chain set forth in SEQ ID NO: 10, respectively, or a third polypeptide chain set forth in SEQ ID NO: 15 and a fourth polypeptide chain set forth in SEQ ID NO: 16, respectively, or a third polypeptide chain set forth in SEQ ID NO: 15 and a fourth polypeptide chain set forth in SEQ ID NO: 17, respectively, or sequences substantially identical (e.g., having at least 80%, 85%, 90%, 92%, 95%, 97%, 98%, 99% or higher identity) to any one of the sequences.

The anti-OX40/PD-L1 bispecific antibody of the present invention can bind to PD-L1 and OX40 proteins simultaneously and maintain the affinity constant of the parent antibody, thereby being able to block PD-1/PD-L1 signaling pathways and activate OX40/OX40 ligand signaling pathways in T cells and natural killer (NK) cells. The anti-OX40/PD-L1 bispecific antibody of the present invention can be used for the treatment, prevention, or diagnosis of diseases associated with the signaling pathways.

ii) In one embodiment, the antibody molecule of the present invention is an anti-VEGF/GITR bispecific antibody or a multispecific antibody.

Vascular endothelial growth factor (VEGF), originally known as vascular permeability factor (VPF) (Senger, D R et al., *Tumor cells secrete a vascular permeability factor that promotes accumulation of ascites fluid, Science*, 1983, 219 (4587): 983-985), is a signaling protein produced by cells that stimulate angiogenesis. VEGF, a subfamily of growth factors, is an important signaling protein involved in angiogenesis. Vascular endothelial growth factors and vascular endothelial growth inhibitors are both present in normal tissues. There is a relative balance between the two, which allows normal generation and differentiation of human blood vessels. However, during the development of diseases, such as tumor growth, there is a sharp increase in VEGF family molecules and a regulatory imbalance between the VEGF family and angiogenic inhibitors. Thus, the division, proliferation and migration of vascular endothelial cells are greatly promoted, vascular permeability is enhanced, and tumor cell apoptosis is inhibited, providing a good microenvironment for tumor growth and metastasis (Lapeyre-Prost A et al., *Immunomodulatory Activity of VEGF in Cancer, Int Rev Cell Mol Biol.* 2017; 330: 295-342). The VEGF family comprises six closely related polypeptides, i.e., the six subtypes of highly conserved homodimeric glycoproteins: VEGF-A, VEGF-B, VEGF-C, VEGF-D, VEGF-E and placental growth factor (PLGF), of which the molecular weight ranges from 35 to 44 kDa. The expression of VEGF-A, including splice variants thereof such as $VEGF_{165}$, is associated with the microvessel density of some solid tumors, and the concentration of VEGF-A in tissues is associated with the prognosis of solid tumors such as breast, lung, prostate, and colon cancers. The bioactivity of each member of the VEGF family is mediated by one or more members of the cell surface VEGF receptor (VEGFR) family. The VEGFR family comprises VEGFR1 (also known as Flt-1), VEGFR2 (also known as KDR, Flk-1), VEGFR3 (also known as Flt-4), etc., wherein VEGFR1 and VEGFR2 are closely associated with angiogenesis, while VEGF-C/D/VEGFR3 is closely associated with lymphangiogenesis.

Clinical studies have shown that using anti-VEGF monoclonal antibodies can block the binding of VEGF to receptor thereof. Bevacizumab (trade name: Avastin) developed by Genentech is a recombinant human-mouse chimeric anti-VEGF antibody which, by blocking the binding of VEGF-A to VEGFR, inactivates VEGFR and therefore exerts an anti-angiogenic effect. Bevacizumab is currently used in the first-line treatment of metastatic colorectal cancer and may be used in the future for treating metastatic lung cancer, breast cancer, pancreatic cancer, kidney cancer and other diseases. Bevacizumab is also one of the most successful antibody drugs.

Glucocorticoid-induced tumor necrosis factor receptor (GITR), also known as TNFRSF18, activation-inducible TNFR family member (AITR), CD357 and GITR-D, is the 18th member of the tumor necrosis factor (TNF) receptor superfamily. GITR was initially identified in murine T cell lines treated with dexamethasone (Nocentini G et al., *A new member of the tumor necrosis factor/nerve growth factor receptor family inhibits T cell receptor-induced apoptosis*, Proc Natl Acad Sci USA. 1997; 94(12):6216-21). Other related members of the TNF receptor superfamily include CD40, CD27, 4-1BB, and OX40. Despite being expressed at low levels in primary CD4+ and CD8+ cells, GITR is constitutively expressed in regulatory T cells (Tone M et al., *Mouse glucocorticoid-induced tumor necrosis factor receptor ligand is costimulatory for T cells*, Proc Natl Acad Sci USA. 2003; 100(25):15059-64). However, once GITR expression is induced on effector T cells, the activation, proliferation and cytokine production of effector T cells are promoted. Regarding CD4+CD25+ regulatory T cells (Tregs), Shimizu reported, based on a mixed culture suppression assay, that activation of GITR leads to suppression of functions of Tregs (Shimizu J et al., *Stimulation of CD25 (+)CD4(+) regulatory T cells through GITR breaks immunological self-tolerance*, Nature Immunology 2002; 3:135-42). In a variety of tumor models, stimulation of GITR mediated by the anti-GITR antibody DTA-1 promotes anti-tumor immunity (Cohen A D et al., *Agonist anti-GITR monoclonal antibody induces melanoma tumor immunity in mice by altering regulatory T cell stability and intra-tumor accumulation*, PLoS One. 2010; 5(5):e10436; Coe D et al., *Depletion of regulatory T cells by anti-GITR mAb as a novel mechanism for cancer immunotherapy*, Cancer Immunol Immunother, 2010; 59(9):1367-77).

GITR is activated after binding to GITR ligands (GITRLs) which are predominantly expressed on APC. After activation, GITR can increase resistance to tumor and virus infection, participate in autoimmune/inflammatory processes, and regulate leukocyte extravasation (Cohen A D et al., ibid.; and Cuzzocrea S et al., *Genetic and pharmacological inhibition of GITR-GITRL interaction reduces chronic lung injury induced by bleomycin instillation*, FASEB J. 2007, 21(1):117-129).

Anti-GITR antibodies are described in the following documents: U.S. Pat. No. 7,025,962, European Patent No. 1947183B1, U.S. Pat. Nos. 7,812,135, 8,388,967, 8,591, 886, European Patent No. EP1866339, PCT Publication No. WO2011/028683, U.S. Pat. No. 8,709,424, PCT Publication No. WO2013/039954, International Publication No WO2013/039954, U.S. Publication No. US2014/0072566, International Publication No. WO2015/026684, PCT Publication No. WO2005/007190, PCT Publication No. WO2007/133822, PCT Publication No. WO2005/055808, PCT Publication No. WO99/40196, PCT Publication No. WO2001/03720, PCT Publication No. WO99/20758, U.S. Pat. No. 6,689,607, PCT Publication No. WO2006/083289, PCT Publication No. WO2005/115451, U.S. Pat. No. 7,618, 632, PCT Publication No. WO2011/051726, International Publication No. WO2004060319, and International Publication No. WO2014012479.

The anti-VEGF/GITR bispecific antibody or multispecific antibody of the present invention targets at least VEGF and GITR simultaneously. The Fab fragments and single-domain antigen-binding sites thereof respectively bind to VEGF and GITR molecules or vice versa, thus blocking signaling pathways of the VEGF family, activating effector T cells and inhibiting functions of Treg.

In one embodiment, the antibody molecule of the present invention comprises single-domain antigen-binding sites specifically binding to GITR and Fab fragments specifically binding to VEGF. In one embodiment, the antibody molecule of the present invention comprises single-domain antigen-binding sites specifically binding to VEGF and Fab fragments specifically binding to GITR.

The Fab fragments specifically binding to GITR or VEGF comprise 6 CDRs derived from VH/VL pairs of an anti-GITR antibody reported in any prior art (e.g., the anti-GITR antibody exemplified above) and VH/VL pairs of anti-GITR antibodies developed in the future, or sequences having one, two, three, four, five, six or more amino acid alterations (e.g., amino acid replacements or deletions) compared to one or more of the 6 CDRs; or comprise 6 CDRs derived from VH/VL pairs of an anti-VEGF antibody reported in any prior art (e.g., the anti-VEGF antibody exemplified above) and VH/VL pairs of anti-VEGF antibodies developed in the future, or sequences having one, two, three, four, five, six or more amino acid alterations (e.g., amino acid replacements or deletions) compared to one or more of the 6 CDRs. In one embodiment, the anti-VEGF antibody is Avastin, which has a heavy chain amino acid sequence set forth in SEQ ID NO: 19 and a light chain amino acid sequence set forth in SEQ ID NO: 18.

The single-domain antigen-binding sites specifically binding to GITR or VEGF comprise heavy chain variable domains (VHs), light chain variable domains (VLs), heavy chain variable domains of antibodies from Camelidae serum that are naturally free of light chain and composed of only two heavy chains, VH-like single domains of IgNAR from sharks, camelized human VH domains, and humanized Camelidae antibody heavy chain variable domains specifically binding to GITR or VEGF.

In one embodiment, the anti-VEGF/GITR bispecific antibody of the present invention comprises two Fab fragments specifically binding to VEGF and two single-domain antigen-binding sites (e.g., VHHs) specifically binding to GITR, each having any of the structures illustrated in FIG. 1A, FIG. 1B, FIG. 1D, FIG. 11A and FIG. 11B. The two Fab fragments specifically binding to VEGF specifically bind to the same epitope or different epitopes on VEGF molecules, and the two single-domain antigen-binding sites specifically binding to GITR specifically bind to the same epitope or different epitopes on GITR molecules.

In one embodiment, the Fab fragments specifically binding to VEGF in the anti-VEGF/GITR bispecific antibody of the present invention comprise all the 6 heavy chain complementarity determining regions (CDRs) and light chain CDRs in the paired heavy chain and light chain variable region sequences derived from the anti-VEGF antibody Avastin set forth in SEQ ID NOs: 22 and 20, or sequences having one, two, three, four, five, six or more amino acid alterations (e.g., amino acid replacements or deletions) compared to one or more of the 6 CDRs.

In one embodiment, the Fab fragments specifically binding to VEGF in the anti-VEGF/GITR bispecific antibody of the present invention comprise the paired heavy chain and light chain variable region sequences derived from the anti-VEGF antibody Avastin set forth in SEQ ID NOs: 22 and 20, or sequences having at least 90%, 91%, 92%, 93%, 94%, 95%, 96%, 97%, 98%, 99% or higher sequence identity to the paired heavy chain and light chain variable region sequences.

In one embodiment, the single-domain antigen-binding sites specifically binding to GITR in the anti-VEGF/GITR bispecific antibody of the present invention comprise a CDR1 shown in GFAFGSS (SEQ ID NO: 25), a CDR2 shown in SGGGFGD (SEQ ID NO: 26) and a CDR3 shown in ATDWRKP (SEQ ID NO: 27), or sequences having one, two, three, four, five, six or more amino acid alterations (e.g., amino acid replacements or deletions) compared to one or more of the 3 CDRs.

In another embodiment, the single-domain antigen-binding sites specifically binding to GITR in the anti-VEGF/GITR bispecific antibody of the present invention comprise an amino acid sequence set forth in SEQ ID NO: 24, or sequences substantially identical (e.g., having at least 80%, 85%, 90%, 92%, 95%, 97%, 98%, 99% or higher identity) thereto.

The CH1 domain and Fc region (comprising the CH2 domain, CH3 domain, and optionally, CH4 domain) in heavy chain constant regions of the anti-VEGF/GITR bispecific antibody of the present invention are not specifically restricted in type, and are preferably corresponding domains derived from heavy chain constant regions of IgG1, IgG2 or IgG4 or sequences substantially identical (e.g., having at least 80%, 85%, 90%, 92%, 95%, 97%, 98%, 99% or higher identity) thereto. More preferably, the CH1 domain and Fc region in the heavy chain constant regions are derived from the CH1 domain and Fc region in heavy chain constant regions of human IgG1, or sequences substantially identical (e.g., having at least 80%, 85%, 90%, 92%, 95%, 97%, 98%, 99% or higher identity) thereto.

In one embodiment, the anti-VEGF/GITR bispecific antibody of the present invention comprises the CH1 domain and Fc region in heavy chain constant regions of IgG4 (e.g., human IgG4). In one embodiment, the anti-VEGF/GITR bispecific antibody of the present invention comprises the CH1 domain and Fc region in heavy chain constant regions of IgG1 (e.g., human IgG1). In another embodiment, the anti-VEGF/GITR bispecific antibody of the present invention comprises the CH1 domain in heavy chain constant regions of IgG4 (e.g., human IgG4) and the Fc region in heavy chain constant regions of IgG1 (e.g., human IgG1), or comprises the CH1 domain in heavy chain constant regions of IgG1 (e.g., human IgG1) and the Fc region in heavy chain constant regions of IgG4 (e.g., human IgG4).

In one embodiment, the Fc domains of the second polypeptide chain and the fourth polypeptide chain of the anti-VEGF/GITR bispecific antibody of the present invention each comprise a hinge region having "CPPC" amino acid residues (SEQ ID NO: 32), and/or respectively comprise Y349C and S354C (according to the Kabat EU numbering system), whereby the second polypeptide chain and the fourth polypeptide chain of the anti-VEGF/GITR bispecific antibody of the present invention form inter-chain disulfide bonds in the Fc domains, which stabilizes the correct pairing of the second polypeptide chain and the fourth polypeptide chain.

In one embodiment, the Fc domains of the second polypeptide chain and/or the fourth polypeptide chain of the anti-VEGF/GITR bispecific antibody of the present invention comprise an amino acid mutation which affects antibody effector functions. In one specific embodiment, the amino acid replacement is LALA mutation.

In another embodiment, the anti-VEGF/GITR bispecific antibody of the present invention comprises a κ light chain constant region and/or a λ light chain constant region, e.g., a human κ light chain constant region and/or a human λ light chain constant region. In one embodiment, the light chain constant regions comprise an amino acid sequence set forth in SEQ ID NO: 8, or sequences substantially identical (e.g., having at least 80%, 85%, 90%, 92%, 95%, 97%, 98%, 99% or higher identity) thereto.

In one embodiment, the Fc domains of the second polypeptide chain and the fourth polypeptide chain of the anti-VEGF/GITR bispecific antibody of the present invention each comprise a stable association of "knob-in-hole". In one embodiment, the amino acid replacement T366W is contained in one of the second polypeptide chain and the fourth polypeptide chain, and the amino acid replacements T366S, L368A, and Y407V (EU numbering) are contained in the other one of the second polypeptide chain and the fourth polypeptide chain. Thereby the protuberance in one chain can be placed at the cavity in the other chain, which facilitates the correct pairing of the second polypeptide chain and the fourth polypeptide chain.

In one embodiment, the immunoglobulin CH1 domain and CL domain of the anti-VEGF/GITR bispecific antibody of the present invention respectively comprise a protuberance and a cavity, or vice versa, and the protuberance or cavity in the CH1 domain can be respectively placed at the cavity or protuberance in the CL domain, such that the first polypeptide chain and the second polypeptide chain of the anti-VEGF/GITR bispecific antibody of the present invention also form a stable association of "knob-in-hole" with each other.

In a specific embodiment, the anti-VEGF/GITR bispecific antibody of the present invention consists of 4 polypeptide chains that are substantially bilaterally symmetrical, wherein the 2 polypeptide chains in the left half of the antibody molecule comprise a first polypeptide chain set forth in SEQ ID No: 18 and a second polypeptide chain set forth in SEQ ID No: 21 respectively, or a first polypeptide chain set forth in SEQ ID No: 18 and a second polypeptide chain set forth in SEQ ID No: 28 respectively, or sequences substantially identical (e.g., having at least 80%, 85%, 90%, 92%, 95%, 97%, 98%, 99% or higher identity) to any of the sequences; and accordingly, the 2 polypeptide chains in the right half of the antibody molecule comprise a third polypeptide chain set forth in SEQ ID NO: 18 and a fourth polypeptide chain set forth in SEQ ID NO: 21 respectively, or a third polypeptide chain set forth in SEQ ID NO: 18 and a fourth polypeptide chain set forth in SEQ ID NO: 28 respectively, or sequences substantially identical (e.g., having at least 80%, 85%, 90%, 92%, 95%, 97%, 98%, 99% or higher identity) to any of the sequences.

The anti-VEGF/GITR bispecific antibody of the present invention can bind to GITR and VEGF proteins simultaneously and maintain the affinity constant of the parent antibody, thereby being able to block signaling pathways of the VEGF family and activate GITR/GITR ligand signaling pathways in effector T cells and natural killer (NK) cells. The anti-VEGF/GITR bispecific antibody of the present invention can be used for the treatment, prevention or diagnosis of diseases related to the signaling pathways.

III. Antibody Molecule Variants of the Present Invention

In certain embodiments, amino acid sequence variants of the bispecific antibody exemplified herein are contemplated. For example, it may be desirable to improve the binding affinity and/or other biological properties of the bispecific antibody. Amino acid sequence variants of the bispecific antibody can be prepared by introducing appropriate modifications to the nucleotide sequence encoding the bispecific antibody or by peptide synthesis. Such modifications include, for example, deleting residues from the amino acid sequence of an antibody and/or inserting residues into the amino acid sequence and/or replacing residues in the amino acid sequence. Any combination of deletions, insertions and replacements can be made to obtain a final construct, so long as the final construct possesses the desired characteristics, such as antigen binding effect.

Conservative replacements are shown in Table 1 under the heading "conservative replacements". More obvious changes are shown in Table 1 under the heading "exemplary replacements and are described further below by referring to amino acid side chain categories. Amino acid replacements can be introduced into the antibody of interest and screened for desired activity on the product, for example, retained/improved antigen binding effect or reduced immunogenicity.

TABLE 1

| Primitive residue | Exemplary replacement | Preferred replacement |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Nle | Leu |
| Leu (L) | Nle; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Nle | Leu |

Amino acids can be grouped according to common side chain characteristics:
(1) Hydrophobicity: Nle, Met, Ala, Val, Leu; Ile;
(2) Neutral hydrophilic: Cys, Ser, Thr, Asn; Gln;
(3) Acidic: Asp, Glu;
(4) Alkaline: His, Lys, Arg;
(5) Residues affecting chain direction: Gly, Pro;
(6) Aromatic: Trp, Tyr, Phe.

Non-conservative replacements will exchange members of one of these classes for members of another class.

IV. Immunoconjugate

The antibody molecule of the present invention can be recombinantly fused to or chemically conjugated to (including covalently and non-covalently conjugated to) a heterologous protein or a polypeptide to produce a fusion protein. Methods of fusion or conjugation of a protein, polypeptide or peptide to an antibody are known in the art. See, for example, U.S. Pat. Nos. 5,336,603, 5,622,929 and EP 367,166.

In addition, the antibody molecule of the present invention can be fused to a labeled sequence (such as a peptide) to facilitate purification. In a preferred embodiment, the labeled amino acid sequence is a hexahistidine peptide, such as tags provided in a pQE vector (QIAGEN, Inc., 9259 Eton Avenue, Chatsworth, Calif., 91311), etc., many of which are commercially available. As described in Gentz et al., 1989, Proc. Natl. Acad. Sci. USA 86: 821-824, for example, a hexahistidine provides convenient purification of fusion proteins. Other peptide tags for purification include, but are not limited to, hemagglutinin ("HA") tags, which correspond to epitopes derived from influenza hemagglutinin proteins (Wilson et al., 1984, Cell 37: 767), and "flag" tags.

In other embodiments, the antibody molecule of the present invention is conjugated to a diagnostic or detectable agent. Such antibodies can be used as a part of clinical test methods (e.g., to determine the effect of a particular therapy), for monitoring or predicting the onset, development, progression, and/or severity of a disease or condition. Such diagnosis and detection can be achieved by coupling antibodies to a detectable substance including but not limited to, a variety of enzymes, such as but not limited to, horseradish peroxidase, alkaline phosphatase, β-galactosidase or acetylcholinesterase; prosthetic groups, such as but not limited to, streptavidin/biotin and avidin/biotin; fluorescent substances, such as but not limited to, umbelliferone, fluorescein, fluorescein isothiocyanate, rhodamine, dichlorotriazinylamine fluorescein, dansyl chloride or phycoerythrin; luminescent substances such as but not limited to luminol; bioluminescent substances, such as but not limited to luciferase, luciferin and aequorin; radioactive materials, such as but not limited to, iodine ($^{131}$I, $^{125}$I, $^{123}$I and $^{121}$I), carbon ($^{14}$C), sulfur ($^{35}$S), tritium ($^{3}$H), indium ($^{115}$In, $^{113}$In, $^{112}$In and $^{111}$In), technetium ($^{99}$Tc), thallium ($^{201}$Ti), gallium ($^{68}$Ga and $^{67}$Ga), palladium ($^{113}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Y, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn and $^{117}$Tin; and positron-emitting metal and non-radioactive paramagnetic metal ions used in various positron emission imaging techniques.

The present invention also includes the use of an antibody molecule conjugated to a therapeutic moiety. An antibody molecule can be conjugated to a therapeutic moiety, such as a cytotoxin (such as a cell growth inhibitor or a cell killer), a therapeutic agent, or a radioactive metal ion, e.g., an alpha emitter. The term "cytotoxin" or "cytotoxic agent" includes any substance that is harmful to cells.

In addition, the antibody molecule of the present invention can be conjugated to a therapeutic or drug moiety that modulates a given biological response. The therapeutic or drug moiety should not be interpreted as limited to classic chemotherapeutics. For example, the drug moiety may be a protein, peptide or polypeptide possessing the desired bioactivity. Such proteins may, for example, include toxins such as abrin, ricin A, Pseudomonas exotoxin, cholera toxin, or diphtheria toxin; proteins such as tumor necrosis factors, alpha-interferon, beta-interferon, nerve growth factors, platelet-derived growth factors, tissue plasminogen activators, apoptotic agents, anti-angiogenic agents, or biological response modifiers, such as lymphokines.

In addition, the antibody molecule of the present invention can be conjugated to a therapeutic moiety such as a radioactive metal ion, e.g., an alpha emitter like $^{213}$Bi, or to a macrocyclic chelating agent that conjugates radioactive metal ions (including but not limited to $^{131}$In, $^{131}$LU, $^{131}$Ym, $^{131}$Ho, and $^{131}$Sm) to polypeptides. In certain embodiments, the macrocyclic chelating agent is 1,4,7,10-tetraazacyclododecane-N, N', N", N'''-tetraacetic acid (DOTA), which can be attached to the antibody via a linker molecule. Such linker molecules are well known in the art and are described in Denardo et al., 1998, *Clin Cancer Res.* 4 (10): 2483-90, each of which is incorporated by reference in its entirety.

Techniques for conjugating a therapeutic moiety to an antibody are well known, see, e.g., Amon et al., *Monoclonal Antibodies For Immunotargeting Of Drugs In Cancer Therapy*, cited in *Monoclonal Antibodies And Cancer Therapy*, Reisfeld et al. (authoring), pp. 243-256 (Alan R. Liss, Inc. 1985).

Antibodies can also be attached to a solid phase support, which is particularly useful for immunoassays or purification of target antigens. Such solid phase supports include, but are not limited to, glass, cellulose, polyacrylamide, nylon, polystyrene, polyvinyl chloride, or polypropylene.

V. Production and Purification of the Antibody Molecule of the Present Invention The antibody molecule of the present invention can be obtained, for example, by solid state peptide synthesis (for example, Merrifield solid phase synthesis) or recombinant production. For recombinant production, polynucleotides encoding any polypeptide chain and/or polypeptide chains of the antibody molecule are isolated and inserted into one or more vectors for further cloning and/or expression in host cells. The polynucleotides can be easily isolated and sequenced using conventional methods. In one embodiment, a vector, preferably an expression vector, comprising one or more polynucleotides of the present invention is provided.

Methods known to those skilled in the art can be used to construct expression vectors. The expression vector includes, but is not limited to, a virus, a plasmid, a cosmid, a lambda phage or a yeast artificial chromosome (YAC).

Once the expression vector comprising one or more polynucleotides of the present invention has been prepared for expression, the expression vector can be transfected or introduced into suitable host cells. Various techniques can be used for this purpose, for example, protoplast fusion, calcium phosphate precipitation, electroporation, retroviral transduction, viral transfection, biolistics, liposome-based transfection, or other conventional techniques.

In one embodiment, a host cell comprising one or more polynucleotides of the present invention is provided. In some embodiments, a host cell comprising the expression vector of the present invention is provided. As used herein, the term "host cell" refers to any kind of cell system that can be engineered to produce the antibody molecule of the present invention. Host cells suitable for replicating and supporting the expression of the antibody molecule of the present invention are well-known in the art. Such cells can be transfected or transduced with a specific expression vector as needed, and a large number of cells containing vectors can be cultivated and then seeded in a large-scale fermentor, so as to obtain sufficient antibody molecule of the present invention for clinical application. Suitable host cells include prokaryotic microorganisms, such as *E. coli*, eukaryotic microorganisms, such as filamentous fungi or yeast, or various eukaryotic cells, such as Chinese hamster ovary cells (CHO), insect cells, and the like. A mammalian cell line suitable for suspension growth may be used.

Examples of useful mammalian host cell lines include monkey kidney CV1 line (COS-7) transformed by SV40; human embryonic kidney line (HEK 293 or 293F cells), baby hamster kidney cell (BHK), monkey kidney cell (CV1), African green monkey kidney cell (VERO-76), human cervical cancer cell (HELA), canine kidney cell (MDCK), buffalo rat liver cell (BRL 3A), human lung cell (W138), human liver cell (Hep G2), CHO cell, NS0 cell, myeloma cell line such as YO, NS0, P3X63 and Sp2/0, etc. For reviews of certain mammalian host cell lines suitable for protein production, see, for example, Yazaki and Wu, *Methods in Molecular Biology*, vol. 248 (edited by B. K. C. Lo, Humana Press, Totowa, N.J.), pp. 255-268 (2003). In a preferred embodiment, the host cell is a CHO, HEK293 or NS0 cell.

Standard techniques for expressing exogenous genes in these host cell systems are known in the art. In one embodiment, a method of producing the antibody molecule of the present invention is provided, wherein the method includes culturing a host cell comprising a polynucleotide encoding the antibody molecule as provided herein under conditions suitable for expressing the antibody molecule, and isolating the antibody molecule from the host cell (or host cell culture medium).

The antibody molecule prepared as described herein can be purified by known prior art such as high performance liquid chromatography, ion exchange chromatography, gel electrophoresis, affinity chromatography, size exclusion chromatography, and the like. The actual conditions used to purify a particular protein also depend on factors such as net charge, hydrophobicity, hydrophilicity, etc., and these will be apparent to those skilled in the art.

The purity of the antibody molecule of the present invention can be determined by any one of a variety of well-known analytical methods including size exclusion chromatography, gel electrophoresis, high performance liquid chromatography, and the like. The antibody molecule provided herein can be identified, screened, or characterized for its physical/chemical properties and/or bioactivity through a variety of assays known in the art.

VI. Pharmaceutical Compositions and Kits

In another aspect, the present invention provides a composition, e.g., a pharmaceutical composition comprising the antibody molecule described herein formulated together with a pharmaceutically acceptable carrier. As used herein, the "pharmaceutically acceptable carrier" includes any and all solvents, dispersion media, isotonic agents and absorption delaying agents, and the like that are physiologically compatible. The pharmaceutical composition of the present invention is suitable for intravenous, intramuscular, subcutaneous, parenteral, rectal, spinal or epidermal administration (e.g., by injection or infusion).

Also disclosed herein are compositions obtained by combining the antibody molecule described herein with more than one therapeutic agent which is selected from one, two, or all of the following categories (i)-(iii): (i) drugs that enhance antigen presentation (e.g., tumor antigen presentation); (ii) drugs that enhance effector cell responses (e.g., B cell and/or T cell activation and/or mobilization); or (iii) drugs that reduce immunosuppression.

The compositions of the present invention may be in a variety of forms. These forms include, for example, liquid, semi-solid, and solid dosage forms, such as liquid solutions (e.g., injectable solutions and infusible solutions), dispersions or suspensions, liposomes, and suppositories. The preferred form depends on the intended mode of administration and therapeutic use. Commonly preferred compositions are in the form of injectable solutions or infusible solutions. The preferred mode of administration is parenteral (e.g., intravenous, subcutaneous, intraperitoneal (i.p.), and intramuscular) injection. In one preferred embodiment, the antibody molecule is administered by intravenous infusion or injection. In another preferred embodiment, the antibody molecule is administered by intramuscular, intraperitoneal or subcutaneous injection.

As used herein, the phrases "parenteral administration" and "administered parenterally" mean modes of administration other than enteral and topical administration, typically by injection, and include, but are not limited to, intravenous, intramuscular, intra-arterial, intradermal, intraperitoneal, transtracheal, subcutaneous injection and infusion.

Therapeutic compositions generally should be sterile and stable under the conditions of manufacture and storage. The compositions can be formulated as solutions, microemulsions, dispersions, liposomes, or lyophilized forms. Sterile injectable solutions can be prepared by adding a required amount of an active compound (i.e., antibody molecule) to a suitable solvent, and then filtering and disinfecting the resulting mixture. Generally, dispersions are prepared by incorporating the active compound into a sterile vehicle, which comprises a basic dispersion medium and other ingredients. Coating agents such as lecithin and the like can be used. In the case of dispersions, the proper fluidity of a solution can be maintained by using a surfactant. Prolonged absorption of injectable compositions can be caused by including in the compositions a substance that delays absorption such as monostearate and gelatin.

In certain embodiments, the antibody molecule of the present invention can be administered orally, such as administered orally with an inert diluent or an edible carrier. The antibody molecule of the present invention can also be encapsulated in gelatin capsules with hard or soft shells, compressed into tablets, or incorporated directly into diets of a subject. For oral therapeutic administration, the compound can be incorporated with excipients and used in the form of ingestible tablets, buccal tablets, troches, capsules, elixirs, suspensions, syrups, wafers, and the like. In order to administer the antibody molecule of the present invention by a method other than parenteral administration, it may be necessary to coat the antibody molecule with, or administer the antibody molecule in combination with, a material preventing inactivation. Therapeutic compositions can also be administered using medical devices known in the art.

The pharmaceutical composition of the present invention may comprise a "therapeutically effective amount" or a "prophylactically effective amount" of the antibody molecule of the present invention. The "therapeutically effective amount" refers to an amount effective to achieve a desired therapeutic result at a necessary dosage for a necessary period of time. The therapeutically effective amount can be varied according to a variety of factors such as disease state, age, gender, and weight of the individual. The therapeutically effective amount is an amount in which any toxic or harmful effect is outweighed by the therapeutically beneficial effect. The "therapeutically effective amount" preferably inhibits a measurable parameter (e.g., tumor growth rate) by at least about 20%, more preferably at least about 40%, even more preferably at least about 60%, and still more preferably at least about 80%, relative to untreated subjects. The ability of the antibody molecule of the present invention to inhibit a measurable parameter (e.g., cancer volume) can be evaluated in an animal model system that predicts efficacy in human tumors.

The "prophylactically effective amount" refers to an amount effective to achieve a desired prophylactic result at a necessary dosage for a necessary period of time. Generally, since a prophylactic dose is used in subjects before or at an earlier stage of a disease, the prophylactically effective amount will be less than the therapeutically effective amount.

A kit comprising the antibody molecule described herein is also within the scope of the present invention. The kit may include one or more other elements, including, for example: instructions for use; other reagents, such as a label or a reagent for coupling; a pharmaceutically acceptable carrier; and a device or other materials for administration to a subject.

VII. Uses of the Antibody Molecule

The antibody molecule disclosed herein has diagnostic uses as well as therapeutic and prophylactic uses in vitro and in vivo. For example, these molecules can be administered to in vitro or ex vivo cultivated cells or to a subject, such as a human subject, to treat, prevent, and/or diagnose a variety of antigen-related diseases, such as cancers, autoimmune diseases, acute and chronic inflammatory diseases, and infectious diseases (e.g., chronic infectious diseases or sepsis).

In one aspect, the present invention provides a diagnostic method for detecting the presence of related antigens in a biological sample, such as serum, semen, or urine or tissue biopsy samples (e.g., from a hyperproliferative or cancerous lesion), in vitro or in vivo. The diagnostic method comprises: (i) exposing a sample (and optionally a control sample) to the antibody molecule as described herein or administering the antibody molecule to a subject under conditions that allow interactions, and (ii) detecting the formation of a complex between the antibody molecule and the sample (and optionally the control sample). The formation of a complex indicates the presence of the related antigen and may show the suitability or need for the treatment and/or prevention described herein.

In some embodiments, the related antigen is detected prior to the treatment, e.g., prior to the initial treatment or prior to a certain treatment after a treatment interval. Detection methods that can be used include immunohistochemistry, immunocytochemistry, FACS, ELISA assays, PCR techniques (e.g., RT-PCR), or in vivo imaging techniques. Generally, antibody molecules used in in vivo and in vitro detection methods are directly or indirectly labeled with a detectable substance to facilitate the detection of bound or unbound conjugates. Suitable detectable substances include a variety of biologically active enzymes, prosthetic groups, fluorescent substances, luminescent substances, paramagnetic (e.g., nuclear magnetic resonance active) substances, and radioactive substances.

In some embodiments, the level and/or distribution of related antigens are/is determined in vivo. For example, the antibody molecule of the present invention labeled with a detectable substance is detected in a non-invasive manner, e.g., by using appropriate imaging techniques such as positron emission tomography (PET) scanning. In one embodiment, for example, the level and/or distribution of related antigens are/is determined in vivo by detecting the antibody molecule of the present invention that is detectably labeled with a PET reagent (e.g., $^{18}$F-fluorodeoxyglucose (FDG)).

In one embodiment, the present invention provides a diagnostic kit comprising the antibody molecule described herein and instructions for use.

In another aspect, the present invention relates to the use of the antibody molecule of the present invention in vivo for the treatment or prevention of diseases requiring modulation of an immune response in a subject, thereby inhibiting or reducing the occurrence or recurrence of related diseases such as cancerous tumors, autoimmune diseases, acute and chronic inflammatory diseases and infectious diseases (for example, chronic infectious diseases or sepsis). The antibody molecule of the present invention may be used alone. Alternatively, the antibody molecule can be administered in combination with other anti-cancer therapeutic/prophylactic agents. When the antibody molecule of the present invention is administered in combination with one or more other drugs, such combinations can be administered in any order or simultaneously.

Accordingly, in one embodiment, the present invention provides a method for modulating an immune response in a subject, which includes administering to a subject a therapeutically effective amount of the antibody molecule described herein. In another embodiment, the present invention provides a method for preventing the occurrence or recurrence of a disease in a subject, which includes administering to the subject a prophylactically effective amount of the antibody molecule described herein.

In some embodiments, cancers treated and/or prevented with the antibody molecule include, but are not limited to, solid tumors, hematological cancers (e.g., leukemia, lymphoma, and myeloma such as multiple myeloma), and metastatic lesions. In one embodiment, the cancer is a solid tumor. Examples of solid tumors include malignancies, such as sarcomas and cancers of multiple organ systems, for example, those cancers that invade the lung, breast, ovary, lymphoid, gastrointestinal tract (e.g., colon), anus, genital and genitourinary tract (e.g., kidney, bladder epithelium, bladder cells, and prostate), pharynx, CNS (e.g., brain, neurological or glial cells), head and neck, skin (e.g., melanoma), nasopharynx (e.g., differentiated or undifferentiated metastatic or locally recurrent nasopharyngeal carcinoma) and pancreas, as well as adenocarcinoma, including malignant tumors such as colon cancer, rectal cancer, renal cell carcinoma, liver cancer, non-small cell lung cancer, small intestine cancer, and esophageal cancer. The cancer can be at an early, intermediate, or advanced stage or a metastatic cancer.

In some embodiments, the cancer is selected from melanoma, breast cancer, colon cancer, esophageal cancer, gastrointestinal stromal tumor (GIST), kidney cancer (e.g., renal cell carcinoma), liver cancer, non-small cell lung cancer (NSCLC), ovarian cancer, pancreatic cancer, prostate cancer, head and neck tumors, gastric cancer, and hematological malignant diseases (e.g., lymphoma).

In some embodiments, infectious diseases treated and/or prevented with the antibody molecule include pathogens for which no effective vaccine is currently available or pathogens for which conventional vaccines have not been fully effective. These include, but are not limited to, HIV, (A, B, and C) hepatitis, influenza, herpes, giardia, malaria, leishmania, *Staphylococcus aureus*, and *Pseudomonas aeruginosa*. The blocking effect of the antibody molecule exemplified by the present invention on PD-L1 can be particularly used to fight infections caused by pathogens (such as HIV) that develop mutant antigens as the infection progresses. These mutant antigens can be regarded as foreign antigens when an anti-human PD-L1 antibody is administered, and thus the antibody molecule exemplified by the present invention can stimulate a strong T cell response that is not inhibited by a negative signal through PD-L1.

In some embodiments, the antibody molecule of the present invention is used to treat and/or prevent inflammatory and autoimmune diseases and graft versus host diseases (GvHD) by down-regulating the immune system. Examples of autoimmune diseases that can be treated and/or prevented by administrating the antibody molecule of the present invention include, but are not limited to, alopecia areata, ankylosing spondylitis, autoimmune hepatitis, segmental ileitis, lupus erythematosus, ulcerative colitis, uveitis, etc. Examples of inflammatory diseases that can be treated and/or prevented by administrating the antibody molecule of the present invention include, but are not limited to, asthma, encephalitis, inflammatory bowel disease, allergic disease, septic shock, pulmonary fibrosis, arthritis and chronic inflammation due to chronic viral or bacterial infections.

The following examples are described to assist in understanding the present invention. The examples are not intended and should not be interpreted in any way as limiting the protection scope of the present invention.

EXAMPLES

Example 1: Construction, Expression, Purification and Property Identification of Anti-OX40/PD-L1 Bispecific Antibody Example 1.1. Construction of Anti-OX40/PD-L1 Bispecific Antibody In this example, 4 kinds of anti-OX40/PD-L1 bispecific antibodies with different structures are constructed, and named as: (1) bispecific antibody Bi-110-112HC, the structural diagram of which is shown in FIG. 1A; (2) bispecific antibody Bi-113-112HC, the structural diagram of which is shown in FIG. 1B; (3) bispecific antibody Bi-119-112LC, the structural diagram of which is shown in FIG. 1C; and (4) bispecific antibody Bi-122-112LC, the structural diagram of which is shown in FIG. 1D. The following is a description of each of the four anti-OX40/PD-L1 bispecific antibodies.

(1) As can be seen from the structural diagram in FIG. 1A, the bispecific antibody Bi-110-112HC consists of 4 polypeptide chains that are bilaterally symmetrical, wherein, from the N-terminus to the C-terminus, the 2 polypeptide chains in the left half (i.e., peptide chain #1 and peptide chain #2) have the amino acid sequences set forth in SEQ ID NO: 6 and SEQ ID NO: 10, respectively. Specifically, from the N-terminus to the C-terminus, the peptide chain #1 set forth in SEQ ID NO: 6 comprises: a VL amino acid sequence derived from the anti-OX40 antibody ADI-20112 set forth in SEQ ID NO: 7; a human κ light chain constant region (CL) amino acid sequence set forth in SEQ ID NO: 8 and located at the C-terminus of the VL amino acid sequence; a linker peptide amino acid sequence set forth in SEQ ID NO: 9 and located at the C-terminus of the human κ light chain constant region (CL) amino acid sequence; and an anti-PD-L1 VHH amino acid sequence set forth in SEQ ID NO: 2 and located at the C-terminus of the linker peptide amino acid sequence. The peptide chain #2 set forth in SEQ ID NO: 10 comprises: a VH amino acid sequence derived from the anti-OX40 monoclonal antibody ADI-20112 set forth in SEQ ID NO: 11; a CH1 amino acid sequence derived from human IgG1 set forth in SEQ ID NO: 12, and located at the C-terminus of the VH amino acid sequence; and an Fc region amino acid sequence derived from human IgG1 set forth in SEQ ID NO: 13, and located at the C-terminus of the CH1 amino acid sequence.

(2) As can be seen from the structural diagram in FIG. 1B, the bispecific antibody Bi-113-112HC consists of 4 polypeptide chains that are bilaterally symmetrical, wherein, from the N-terminus to the C-terminus, the 2 polypeptide chains in the left half (i.e., peptide chain #1 and peptide chain #2) have the amino acid sequences set forth in SEQ ID NO: 14 and SEQ ID NO: 10, respectively. Specifically, from the N-terminus to the C-terminus, the peptide chain #1 set forth in SEQ ID NO: 14 comprises an anti-PD-L1 VHH amino acid sequence set forth in SEQ ID NO: 2, a linker peptide amino acid sequence set forth in SEQ ID NO: 9, a VL amino acid sequence derived from the anti-OX40 antibody ADI-20112 set forth in SEQ ID NO: 7, and a human κ light chain constant region (CL) amino acid sequence set forth in SEQ ID NO: 8. The peptide chain #2 has an amino acid sequence set forth in SEQ ID NO: 10.

(3) As can be seen from the structural diagram in FIG. 1C, the bispecific antibody Bi-119-112LC consists of 4 polypeptide chains that are bilaterally symmetrical, wherein, from the N-terminus to the C-terminus, the 2 polypeptide chains in the left half (i.e., peptide chain #1 and peptide chain #2) have the amino acid sequences set forth in SEQ ID NO: 15 and SEQ ID NO: 16, respectively. Specifically, from the N-terminus to the C-terminus, the peptide chain #1 set forth in SEQ ID NO: 15 comprises a VL amino acid sequence derived from the anti-OX40 antibody ADI-20112 set forth in SEQ ID NO: 7, and a human κ light chain constant region (CL) amino acid sequence set forth in SEQ ID NO: 8. From the N-terminus to the C-terminus, the peptide chain #2 set forth in SEQ ID NO: 16 comprises a VH amino acid sequence derived from the anti-OX40 monoclonal antibody ADI-20112 set forth in SEQ ID NO: 11, a CH1 amino acid sequence derived from human IgG1, an anti-PD-L1 VHH amino acid sequence set forth in SEQ ID NO: 2, and an amino acid sequence derived from Fc region of human IgG1 set forth in SEQ ID NO: 13.

(4) As can be seen from the structural diagram in FIG. 1D, the bispecific antibody Bi-122-112LC consists of 4 polypeptide chains that are bilaterally symmetrical, wherein, from the N-terminus to the C-terminus, the 2 polypeptide chains in the left half (i.e., peptide chain #1 and peptide chain #2) have the amino acid sequences set forth in SEQ ID NO: 15 and SEQ ID NO: 17, respectively, and from the N-terminus to the C-terminus, the peptide chain #2 comprises an anti-PD-L1 VHH amino acid sequence set forth in SEQ ID NO: 2, a linker peptide amino acid sequence set forth in SEQ ID NO: 9, a VH amino acid sequence derived from the anti-OX40 monoclonal antibody ADI-20112 set forth in SEQ ID NO: 11, a CH1 amino acid sequence derived from human IgG1 set forth in SEQ ID NO: 12, and an amino acid sequence derived from Fc region of human IgG1 set forth in SEQ ID NO: 13.

Example 1.2. Expression, Purification and Analysis of Anti-OX40/PD-L1 Bispecific Antibody In this example, the nucleotide sequences encoding the peptide chain #1 and peptide chain #2 of the anti-OX40/PD-L1 bispecific antibodies constructed in Example 1.1 were linked to the commercially available eukaryotic expression vector pTT5 via multiple cloning sites, and after expression in eukaryotic cells and purification, anti-OX40/PD-L1 bispecific antibodies Bi-110-112HC, Bi-113-112HC, Bi-119-112LC and Bi-122-112LC were obtained. The specific operation is as follows.

Genewiz Suzhou was entrusted to synthesize the coding nucleotide sequences of the above peptide chains of the bispecific antibodies Bi-110-112HC, Bi-113-112HC, Bi-119-112LC and Bi-122-112LC. The synthesized nucleotide sequences encoding the peptide chains were separately linked into the vector pTT5 using appropriate restriction enzymes and ligases, and recombinant vectors respectively comprising the nucleotide sequences encoding the peptide chains were obtained.

The recombinant vectors were verified to be correct by sequencing and then used for subsequent expression.

HEK293 cells (purchased from Invitrogen) were subcultured in Expi293 cell culture medium (purchased from Invitrogen). The day before transfection, the cell culture was centrifuged to obtain cell precipitation. The cell density was adjusted to $1\times10^6$ cells/mL by suspending the cells with fresh Expi293 cell culture medium. HEK293 cells were further cultivated such that the cell density in the culture on the day of transfection was about $2\times10^6$ cells/mL. F17 culture medium (purchased from Gibco, Product Catalog. No. A13835-01) that was 1/10 the final volume of HEK293 cell suspension was used as a transfection buffer. 200 µg of the prepared recombinant plasmids respectively comprising the nucleotide sequences encoding the peptide chain #1 and the peptide chain #2 at a molar ratio of 1:1 was added to each milliliter of the transfection buffer, and the resulting mixture was mixed well. Then 30 µg of polyethylenimine (PEI) (Polysciences, Catalog No.: 23966) was added, and the resulting mixture was mixed well and incubated at room temperature for 10 min, and then the PEI/DNA mixture was gently poured into HEK293 cell suspension. The culture was mixed gently and the cells were cultivated overnight at 8% $CO_2$ and 36.5° C.

After an overnight incubation, 1/50 of the volume of culture after transfection of 200 g/L FEED (Sigma, Catalog No.: H6784-100G) and 1/50 of the volume of culture after transfection of 200 g/L glucose solution were supplemented to the culture flask. The system was mixed gently and incubated at 8% $CO_2$ and 36.5° C. After 20 h, VPA (Gibco, Catalog No.: 11140-050) was added to a final concentration of 2 mM/L. On day 7 of continuous culturing or when the cell viability was <60%, the culture was collected and centrifuged at 7500 rpm for 30 min. The cell supernatant was filtrated using SARTOPORE (Sartorius, Catalog No.: 5441307H4) and purified by affinity chromatography on an AKTApure system (GE Healthcare).

Specific affinity chromatography purification steps are as follows: A MabSelect SuRe (GE Healthcare, Catalog No.: 17-5438-03) affinity chromatography column was selected and mounted in the AKTApure system. The AKTApure system equipped with a MabSelect SuRe affinity chromatography column was sterilized with 0.1 M NaOH overnight, and then the system was washed and the column was equilibrated with 5 times column volume of a binding buffer (Tris 20 mM, NaCl 150 mM, pH 7.2). The filtered cell supernatant was loaded on the column. The column was reequilibrated with 5-10 times column volume of the binding buffer and monitored to UV flatness using the UV detection device equipped with the AKTApure system. Then, the antibody was eluted with an elution buffer (citric acid+sodium citrate 100 mM, pH 3.5), and samples were collected based on the UV absorption value. Each 1 mL of the collected solution was neutralized with 80 VL of a neutralization buffer (Tris-HCl 2M) for late use.

Collected samples in each fraction tube were analyzed by size exclusion chromatography (SEC). The SEC results are shown in FIG. 2A, FIG. 2B, FIG. 2C and FIG. 2D. The purity of the bispecific antibody Bi-110-112HC is 71.40%, the purity of the bispecific antibody Bi-113-112HC is 84.54%, the purity of the bispecific antibody Bi-119-112LC is 99.43%, and the purity of the bispecific antibody Bi-122-112LC is 94.79%.

The purified bispecific antibody solution was centrifuged in a 15 mL ultrafiltration centrifuge tube at 4,500 rpm for 30 min. The protein was diluted with PBS and further centrifuged at 4,500 rpm for 30 min, and this operation was repeated twice to exchange the buffer. The antibodies after buffer exchange were combined to measure the antibody concentration.

In subsequent experiments, the bispecific antibody Bi-119-112LC with 99.43% main peak purity of monomer was selected for further study.

Example 1.3. Determination of the Dissociation Constant of Anti-OX40/PD-L1 Bispecific Antibody The equilibrium dissociation constant ($K_D$) for the binding of the above exemplary anti-OX40/PD-L1 bispecific antibody Bi-119-112LC of the present invention to OX40 and PD-L1 was determined by a kinetic binding assay using the Octet system manufactured by ForteBio. A ForteBio affinity assay was performed according to the method reported in the literature (Estep, P, et al., High throughput solution Based measurement of antibody-antigen affinity and epitope binning. *MAbs*, 2013, 5(2): p. 270-278). Briefly, the AHC sensor (Pall, Catalog No.: 1506091) was immersed in a SD buffer (PBS 1x, BSA 0.1%, Tween 20 0.05%) and equilibrated at room temperature, half an hour before the experiment. 100 μL of the SD buffer as a blank control (for background subtraction), 100 μL of 100 nM purified bispecific antibody Bi-119-112LC, and anti-PD-L1 humanized Nb-Fc antibody (PCT/CN2017/095884) and the anti-OX40 antibody ADI-20112 (China Patent Application No. 201710185400.8) as controls, and 100 μL of solutions of human PD-L1-his (100 nM) and human OX40-his (100 nM) (Acrobiosystems) diluted in the SD buffer as antigens, were added to wells of a 96-well black polystyrene half-area microplate (Greiner). The anti-human IgG Fc biosensor AHC was immersed in each well containing the antibody solution, and immersed at room temperature for 600 s to load the samples. The sensor was then washed in the SD buffer until it returned to the baseline, and then immersed in a well containing 100 μL of the antigen solution to monitor the binding of the antibody to the antigen. The sensor was then transferred to a well containing 100 μL of the SD buffer to monitor the antibody dissociation. The rotation speed was 400 rpm and the temperature was 30° C. The background-corrected association and dissociation curves were fitted by the Octet analysis software (ForteBio) to generate the binding rate constant ($k_{on}$) and dissociation rate constant ($k_{dis}$), which are then used to calculate the equilibrium dissociation constant ($K_D$). The $k_{on}$, $k_{dis}$ and $K_D$ data of the bispecific antibody Bi-119-112LC and the antigen OX40 or PD-L1 are shown in Table 1 and Table 2.

TABLE 1

Affinity of anti-OX40/PD-L1 bispecific antibody to OX40 as determined by ForteBio kinetic binding assay

| Antibody | Antibodies on AHC tip/human OX40-His in solution (100 nM) [monovalent affinity (M)] | Binding constant $K_{on}$ ($M^{-1} s^{-1}$) | Dissociation constant $k_{dis}$ ($s^{-1}$) |
|---|---|---|---|
| ADI-20112 | 2.15E−07 | 1.35E+05 | 2.90E−02 |
| Bi-119-112LC | 6.07E−08 | 2.20E+05 | 1.33E−02 |

TABLE 2

Affinity of anti-OX40/PD-L1 bispecific antibodies to PD-L1 as determined by ForteBio kinetic binding assay

| Antibody | Antibodies on AHC tip/human PD-L1-His in solution (100 nM) [monovalent affinity (M)] | Binding constant $K_{on}$ ($M^{-1} s^{-1}$) | Dissociation constant $k_{dis}$ ($s^{-1}$) |
|---|---|---|---|
| Bi-119-112LC | 1.31E−08 | 3.22E+05 | 4.23E−03 |
| Humanized Nb-Fc | 1.54E−08 | 2.51E+05 | 3.86E−03 |

From the above data, it can be seen that the bispecific antibody Bi-119-112LC of the present invention can simultaneously bind to PD-L1 and OX40 proteins in solution, and maintain the affinity constants of the parent antibody ADI-20112 and the humanized Nb-Fc to the respective corresponding antigens.

Example 1.4. Analysis on Binding of the Anti-OX40/PD-L1 Bispecific Antibody of the Present Invention to CHO Cells Overexpressing OX40 or PD-L1

The binding of anti-OX40/PD-L1 bispecific antibody Bi-119-112LC of the present invention to CHO cells overexpressing OX40 or PD-L1 was determined by FACS.

Briefly, by using the ExpiCHO™ Expression System Kit (Invitrogen, Catalog No.: A29133) according to the instructions of the manufacturer, the pCHO1.0 vector (Invitrogen) carrying human PD-L1 cDNA (Sino Biological) cloned to a multiple cloning site (MCS) was transfected into Chinese hamster ovary cancer cells (CHO) (Invitrogen) to give CHO cells overexpressing human PD-L1 cells (CHO-PD-L1 cells). The CHO-PD-L1 cells were counted, diluted to 1×10$^6$ cells/mL with a cell culture medium, and added to a U-bottom 96-well plate at 100 μL/well. Then the cell suspension was centrifuged at 400 g on a centrifuge for 5 min to remove the cell culture medium. 100 μL of each of serial dilutions of the bispecific antibody Bi-119-112LC of the present invention and humanized Nb-Fc as a control were added to a U-shaped plate, and then the cells were resuspended and put onto the ice to stand for 30 min. The cell suspension was centrifuged at 400 g for 5 min, and then the supernatant was removed, and the cells were washed with PBS to remove the unbound antibodies. The resulting cell suspension was centrifuged at 400 g for 5 min to remove PBS. 100 μL of the solution of PE-conjugated anti-human Fc antibody (SOUTHERN BIOTECH) diluted at a ratio of 1:200 was added to each well, and the cells were incubated on ice in the absence of light for 30 min. Then the cell suspension was centrifuged at 400 g for 5 min to remove supernatant. The cells were washed with PBS to remove the unbound PE-conjugated anti-human Fc antibody. Then the cells were resuspended with 100 μL of PBS, and the binding of the antibodies to cells was assayed by FACS. The results are shown in FIG. 3.

Figure 3:
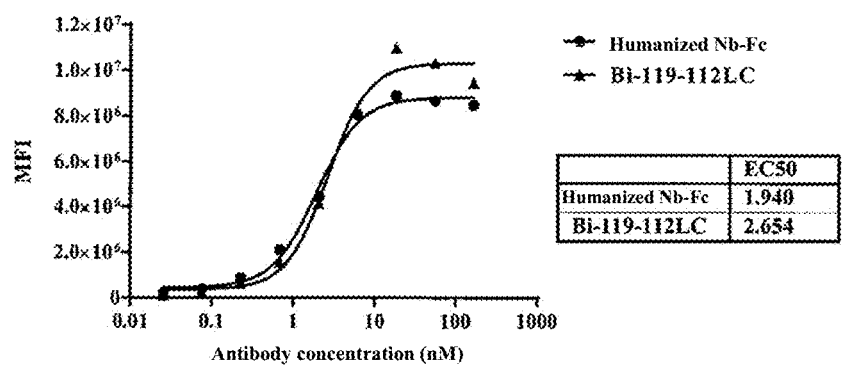
FIG. 3 shows the binding detected by FACS of the anti-OX40/PD-L1 bispecific antibody Bi-119-112LC and an anti-PD-L1 humanized Nb-Fc antibody as a control to CHO cells overexpressing PD-L1. The horizontal axis represents the antibody concentration, and the vertical axis represents the mean fluorescence intensity (MFI).

It can be seen from FIG. 3 that the bispecific antibody Bi-119-112LC of the present invention can bind to PD-L1 expressed on the surface of cells with a binding $EC_{50}$ of 2.654 nM, and has a binding ability similar to that of the parent anti-PD-L1 antibody to PD-L1 expressed on the surface of cells (with an $EC_{50}$ of 1.940 nM).

Likewise, the pCHO1.0 vector (Invitrogen) carrying human OX40 cDNA (Sino Biological Inc.) cloned to a multiple cloning site (MCS) was transfected into Chinese hamster ovary cancer cells (CHO) (Invitrogen) to give CHO cells overexpressing human OX40 cells (CHO-OX40 cells).

FACS assay for CHO-OX40 was carried out. The experimental operation was the same as the above FACS assay for CHO-PD-L1 cells except that a different cell line was used and ADI-20112 antibody was used as a control antibody.

Figure 4:
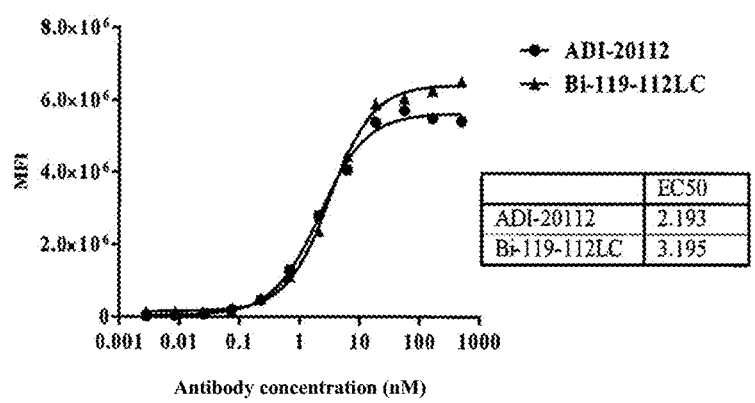
FIG. 4 shows the binding detected by FACS of the anti-OX40/PD-L1 bispecific antibody Bi-119-112LC and an anti-OX40 antibody ADI-20112 as a positive control to CHO cells overexpressing OX40. The horizontal axis represents the antibody concentration, and the vertical axis represents the mean fluorescence intensity (MFI).

The results are shown in FIG. 4. It can be seen from FIG. 4 that the bispecific antibody Bi-119-112LC of the present invention can bind to OX40 expressed on the surface of cells with a binding $EC_{50}$ of 3.195 nM, and has a binding ability similar to that of the parent anti-OX40 antibody to OX40 expressed on the surface of cells (with an $EC_{50}$ of 2.193 nM).

Example 1.5. Analysis on the Anti-OX40/PD-L1 Bispecific Antibody of the Present Invention Simultaneously Binding to CHO Cells Overexpressing OX40 and CHO Cells Overexpressing PD-L1

To verify whether the anti-OX40/PD-L1 bispecific antibody Bi-119-112LC of the present invention can bind simultaneously to target antigens from different cells or not, the cross-linking of different cells induced by the bispecific antibody was tested in this example by flow cytometry. The specific experimental process was as follows.

1) CHO-PD-L1 cells and CHO-OX40 cells were obtained as described in Example 1.4 and cultivated. Cultures containing CHO-PD-L1 cells and CHO-OX40 cells were centrifuged at 400 g for 5 min on a centrifuge, respectively, to remove the cell culture medium. After washed once with PBS, the cells were resuspended in PBS. The cells were counted, with the cell density adjusted to $2\times10^6$ cells/mL. CHO-PD-L1 cells and CHO-OX40 cells were added with CellTracker™ Deep Red (Thermo) and Cell Trace CFSE (Invitrogen) dyes at 1:5000, respectively, and placed at 37° C. for 30 min. The mixture was centrifuged at 400 g for 5 min on a centrifuge, and then the supernatant was remove, and the cells were washed once with PBS.

2) Samples diluted in a gradient (anti-OX40/PD-L1 bispecific antibody Bi-119-112LC, anti-PD-L1 humanized Nb-Fc antibody (PCT/CN2017/095884), and anti-OX40 antibody ADI-20112 (China Patent Application No. 201710185400.8)) were added to a U-bottom 96-well plate. The stained CHO-PD-L1 cells of 1) above were added and mixed (with the final cell density of $1.5\times10^6$ cells/mL). The U-bottom 96-well plate was placed at 4° C. for 30 min, and then the plate was centrifuged at 400 g for 5 min and washed four times with PBS. The cells were then resuspended in PBS.

3) The stained CHO-OX40 cells of 1) above were added to the cell suspension of 2) above in a U-bottom 96-well plate so that the final density of CHO-OX40 cells was adjusted to $1\times10^6$ cells/mL, and FACS assay was carried out after the plate was placed at room temperature for 1 h. The ratio of double positive cells of channel 2 and channel 4 can reflect the cross-linking of cells caused by the anti-OX40/PD-L1 bispecific antibody Bi-119-112LC.

Figure 5:
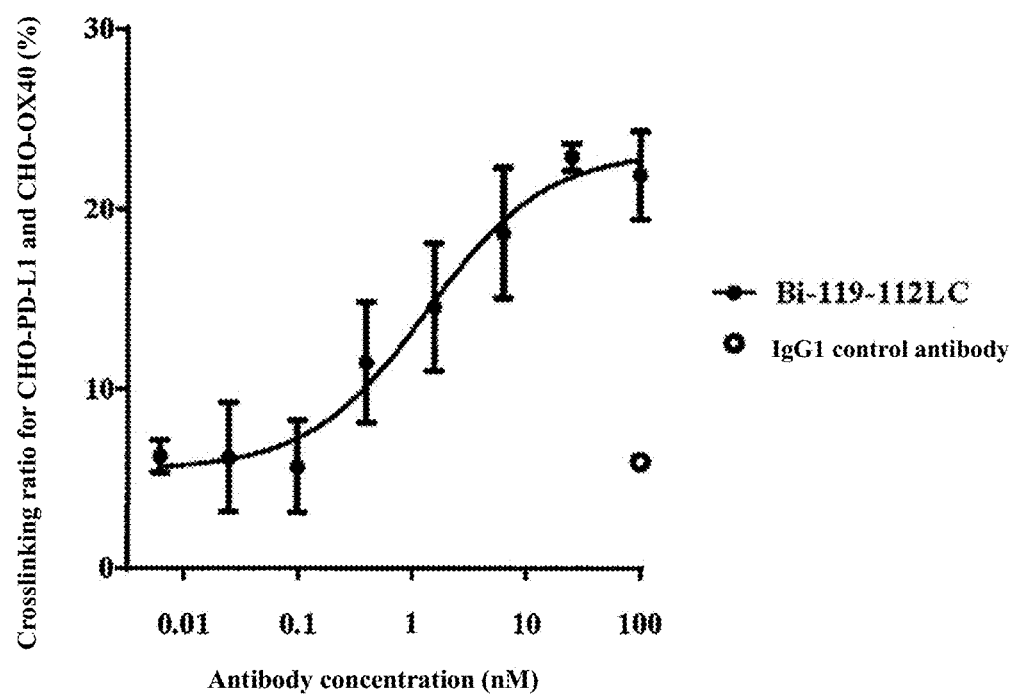
FIG. 5 shows the simultaneous binding of the anti-OX40/PD-L1 bispecific antibody to CHO cells overexpressing OX40 and CHO cells overexpressing PD-L1.

The results of FACS assay are shown in FIG. 5. The anti-OX40/PD-L1 bispecific antibody Bi-119-112LC can induce cross-linking of CHO-PD-L1 cells and CHO-OX40 cells, indicating that the bispecific antibody of the present invention can bind to target antigens from different cell surfaces simultaneously. In this example, the heavy chain (HC) amino acid sequence of the IgG1 negative control is set forth in SEQ ID NO: 29, and the light chain (LC) amino acid sequence of the IgG1 negative control is set forth in SEQ ID NO: 30.

Example 1.6. Analysis on Anti-OX40/PD-L1 Bispecific Antibody of the Present Invention Blocking the Binding of PD-1 to CHO Cells Overexpressing PD-L1

To verify whether the anti-OX40/PD-L1 bispecific antibody of the present invention can block the binding of PD-1 to CHO cells overexpressing PD-L1 or not, the anti-OX40/PD-L1 bispecific antibody of the present invention blocking the binding of PD-1 protein to CHO cells overexpressing PD-L1 was tested in this example by flow cytometry. The specific experimental process was as follows:

1) CHO-PD-L1 cells were obtained as described in Example 1.4 and cultivated. Cultures containing $2.4\times10^7$ CHO-PD-L1 cells were centrifuged at 400 g for 5 min on a centrifuge to remove the cell culture medium. After washed once with PBS, the cells were resuspended in 5 mL of PBS.

2) Cell plating: the CHO-PD-L1 cells of 1) were added to a 96-well U-bottom plate at 50 μL/well for late use.

3) Preparation of sample solutions in a gradient concentration: 200 VL of biotinylated human PD-1 proteins (Acrobiosystems, PD1-H82F2) with a human PD-1 protein concentration of 0.2 mg/mL was added to 5 mL of PBS, and then mixed well. The test samples were diluted with a mixed solution of biotinylated human PD-1 and PBS at 12 concentration points in total, with an initial concentration of 1000 nM and 3-fold dilution at the latter 11 concentration points.

4) The prepared samples in a gradient concentration were added, at 50 μL/well, to a 96-well U-bottom coagulation plate of 2) with cells plated well, and then well mixed. The cells were incubated at 4° C. for 30 min, and then the cell suspension was centrifuged at 400 g for 5 min to remove the supernatant. 150 μL of PBS was added to each well, and the mixture was centrifuged at 400 g for 5 min to remove the supernatant. This operation was repeated three times.

5) 100 μL of Streptavidin-R-phytoerythrin (SAPE) (THERMO, 521388) diluted at a ratio of 1:200 was added to each well, and then the cells were incubated at 4° C. for 30 min.

6) 150 μL of PBS was added to each well, and then the cell suspension was centrifuged at 400 g for 5 min to remove the supernatant. This operation was repeated twice. The cells were resuspended in 100 μL of PBS, and detected by flow cytometer (BD Biosciences, ACCURIC6).

Figure 6:
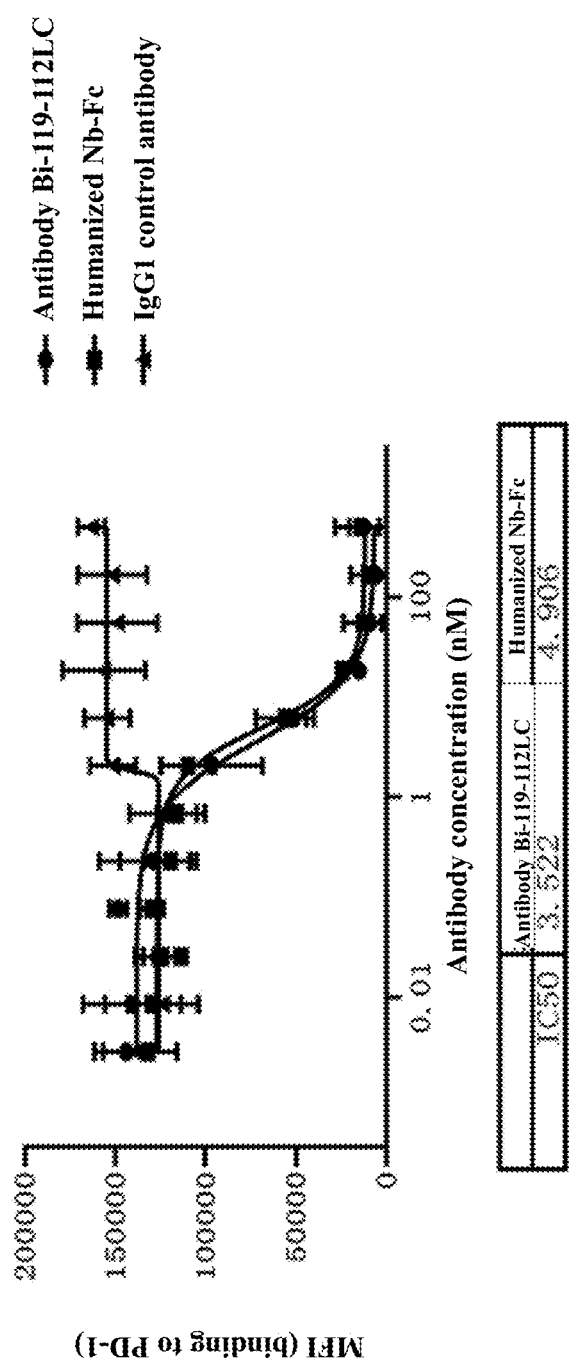
FIG. 6 shows the effect of the anti-OX40/PD-L1 bispecific antibody of the present invention on the binding of human PD-1 to PD-L1, demonstrating that the bispecific antibody Bi-119-112LC of the present invention blocks the binding of human PD-1 to PD-L1, and shows the effect of anti-PD-L1 humanized Nb-Fc as a control and IgG1.

The IgG1 negative control used in this example was the same as that used in Example 1.5 above. The experimental results are shown in FIG. 6. The anti-OX40/PD-L1 bispecific antibody Bi-119-112LC of the present invention can effectively block the binding of PD-1 to CHO cells overexpressing PD-L1, and the blocking activity is similar to that of the anti-PD-L1 humanized Nb-Fc antibody ($IC_{50}$ of the anti-OX40/PD-L1 bispecific antibody is 3.522 nM, and $IC_{50}$ of the anti-PD-L1 humanized Nb-Fc antibody is 4.906 nM).

Example 1.7. Assay of Anti-PD-L1 Activity of Anti-OX40/PD-L1 Bispecific Antibody Based on Luciferase Reporter Genes To determine whether the anti-OX40/PD-L1 bispecific antibody can relieve the inhibitory effect of PD-1/PD-L1 interaction on the NFAT signaling pathway or not, in this example, luciferase reporter genes were used to assay cell lines (Promega, CS187109), and the inhibitory ability of bispecific antibody on the PD-1/PD-L1 interaction were reflected by detecting the expression of luciferase. The specific experimental process was as follows:

Considering that the exploration of an antibody should be based on the understanding of the mechanisms of action (MOA) and the biological activity of the antibody, PD-1/PD-L1 Blockade Bioassay, Cell Propagation Model (Promega) was adopted in this example to study the anti-PD-L1 biological activities of the bispecific antibody of the present invention.

As an MOA-based determination method related to biology, PD-1/PD-L1 Blockade Bioassay of Promega can be used to determine the potency and stability of an antibody capable of blocking the PD-1/PD-L1 interaction. The determination method consists of two types of genetically engineered cell lines:

PD-1 effector cells: Jurkat T cells expressing luciferase induced by the nuclear factor of activated T cells (NFAT) and stably expressing human PD-1.

PD-L1 aAPC/CHO-K1 cells: CHO-K1 cells stably expressing human PD-L1 and cell surface proteins activating corresponding TCRs in an antigen-independent manner.

The binding of PD-1 to PD-L1 can block the signal transduction downstream of NFAT, thereby inhibiting the expression of luciferase. When the PD-1 antibody or the PD-L1 antibody is added, such blocking effect is reversed, and luciferase is expressed, and as a result, a fluorescence signal is detected. This determination method has good sensitivity, specificity, accuracy and stability.

An assay was carried out according to the product instructions of the manufacturer.

1) PD-L1 aAPC/CHO-K1 cells were plated the day before activity assay. The culture supernatant was discarded. The cells were washed with PBS once, and then pancreatin (Gibco, 25200072) was added. The cells were incubated at 37° C. for 3-5 min, and then the digestion was stopped with four-fold the volume of the cell mixture of RPMI1640 (Gibco, 22400-071) culture medium containing 10% FBS (HyClone, SH30084.03), and the cells were collected. A small amount of the cell mixtures was taken to determine the cell concentration, and a needed volume of cell suspension was centrifuged at 400 g for 10 min to remove the supernatant. The cells were resuspended in RPMI1640 (Gibco, 22400-071) culture medium containing 10% FBS (HyClone, SH30084.03) as an assay buffer to achieve a cell density of $4\times10^5$ cells/mL. The cell suspension was added to a 96-well white cell culture plate (Nunclon, 136101) at 100 μL/well, and PBS was added to the side wells of the 96-well white cell culture plate at 200 μL/well. The cells were cultivated overnight in a carbon dioxide incubator at 37° C., 5% $CO_2$.

2) The test samples in a sterile 96-well plate (Nunclon, 442404) were diluted with RPMI1640 culture medium containing 10% FBS at 12 concentration points in total, with an initial concentration of 200 nM and 3-fold dilution from the second concentration point to the 12th concentration point.

3) PD-1 effector cells were collected, counted, and centrifuged at 400 g for 5 min, and then the cells were resuspended in an assay buffer to achieve a cell density of $1.25\times10^6$ cells/mL.

4) The white cell culture plate was taken out from the incubator, and 95 μL of the solution in each well was discarded. Then 40 μL of the diluted antibody of 2) and 40 μL of the treated cells (Jurkat/PD-1 cells) of 3) were added to each well sequentially.

5) The cells were cultivated for 6 h in a carbon dioxide incubator at 37° C., 5% $Co_2$. 6) The white cell culture plate was taken out, and let stand at room temperature for 5-10 min. 7) Bio-Glo™ buffer (Promega, G7940) was thawed and added with the Bio-Glo™ substrate (Promega, G7940), and the mixture was mixed well. The resulting Bio-Glo™ reagent was added to the wells of the aforementioned assay plate at 80 μL/well after 6 h of incubation. The plate was placed at room temperature for 5-10 min.

8) Full wavelength chemiluminescence was collected by a Spectra Max 13 microplate reader (Thermo, Max i3) with a collection time per well of 1000 ms.

Figure 7:
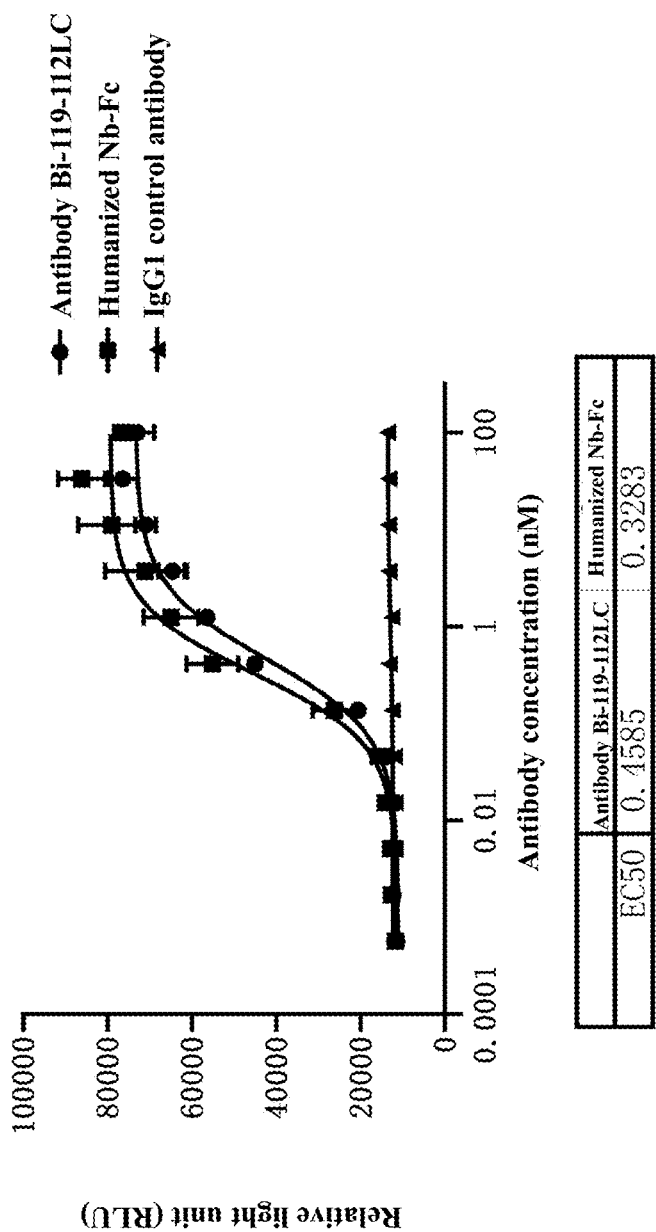
FIG. 7 shows that the anti-OX40/PD-L1 bispecific antibody Bi-119-112LC of the present invention effectively eliminates the blocking of NFAT signaling pathways by PD1/PD-L1 interaction, which leads to the acquisition of a fluorescence signal, and shows the effect of anti-PD-L1 humanized Nb-Fc as a control and IgG1.

The IgG1 negative control used in this example was the same as that used in Example 1.5 above. The experimental results are shown in FIG. 7. The anti-OX40/PD-L1 bispecific antibody Bi-119-112LC of the present invention can effectively relieve the blocking effect of the PD1/PD-L1 interaction on NFAT signaling pathway, and the activity is similar to that of the anti-PD-L1 humanized Nb-Fc antibody (EC so of the anti-OX40/PD-L1 bispecific antibody is 0.4585 nM, and $EC_{50}$ of the anti-PD-L1 humanized Nb-Fc antibody is 0.3283 nM).

Example 1.8. Assay of Anti-OX40/PD-L1 Bispecific Antibody of the Present Invention Mediating PD-L1-Dependent Activation of OX40-Mediated Signaling Pathway Based on Luciferase Reporter Genes To assay the bioactivity of the anti-OX40/PD-L1 bispecific antibody of the present invention in activating the OX40-mediated signaling pathway in the presence of CHO-PD-L1 cells obtained as described in Example 1.4, a stable cell strain Jurkat-OX40-NF-κB-Luc-Rep (Innovent Biologics (Suzhou) Co., Ltd.) was adopted to detect the OX40-mediated transcriptional activation, thus evaluating whether the anti-OX40/PD-L1 bispecific antibody of the present invention has an activator activity of an anti-OX40 antibody or not. Jurkat cells (obtained from ATCC in the USA) introduced with human OX40 constructs (purchased from Sino) and NF-κB-luciferase constructs (NF-κB promoter-luc, Promega) and overexpressing human OX40 were activated with anti-human CD3 (BD Biosciences, Catalog No.: 555329), anti-human CD28 (BD Biosciences, Catalog No.: 555725) and the antibody of the present invention in the solution for 16 h, and then developed with Bio-Glo™ reagent. The specific experimental process was as follows:

Preparation of solution: Assay buffer: 90% RPIM-1640 (Gibco, 22400-071), 10% FBS (HyClone, SH30084.03), 2 μg/mL anti-human CD3 (BD Biosciences, Catalog No.: 555329), 2 μg/mL anti-human CD28 (BD Biosciences, Catalog No.: 555725). Prepare freshly prior to use.

Experimental Procedures:

1) A small amount of cell suspension was taken and the cell density was measured using a cell counting plate. The cell suspension was centrifuged at 400 g for 10 min to remove the supernatant, and the cells were gently resuspended in an assay buffer, wherein the cell density of Jurkat-OX40-NF-κB-Luc-Rep was $4\times10^5$ cells/mL, and the cell density of CHO-PD-L1 was $4\times10^5$ cells/mL.

2) The cell suspension was transferred to a loading slot, and a 96-well white cell culture plate (NUNC, Catalog No.: 136101) was taken out. 50 μL of Jurkat-OX40-NF-κB-Luc-Rep cells and 50 μL of CHO-PD-L1 cell suspension of 1) were added to each well, and test samples were added at an initial concentration of 100 nM, with 3-fold dilution from the second concentration point to the 13th concentration point, 13 concentration points in total, in triplicate.

3) The cells were cultivated for 16 h in a carbon dioxide incubator at 37° C., 5% Co$_2$.

4) The Bio-Glo™ buffer (Promega, Catalog No.: G7940) was thawed and Bio-Glo™ substrate (Promega, Catalog No.: G7940) was added, and the mixture was mixed well. The resulting Bio-Glo™ reagent was added to the wells of the aforementioned assay plate at 80 μL/well after 16 h of incubation. The plate was placed at room temperature for 5-10 min. Full wavelength chemiluminescence was collected by a Spectra Max 13 microplate reader (Thermo, Max i3) with a collection time per well of 1000 ms.

Figure 8:
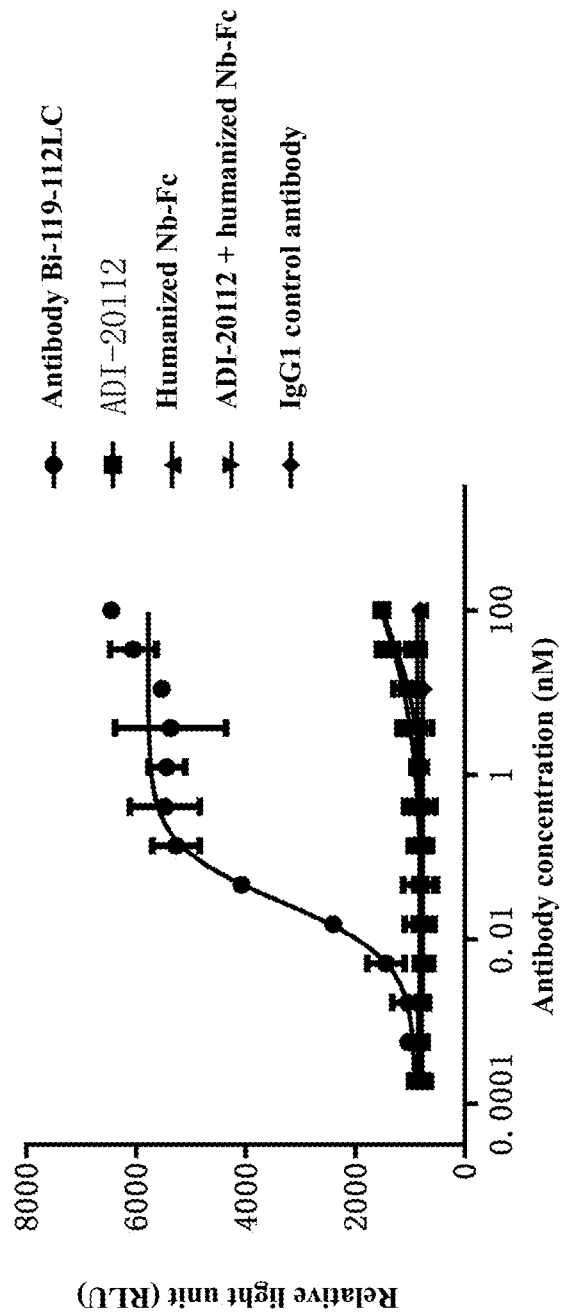
FIG. 8 shows the effect of the anti-OX40/PD-L1 bispecific antibody Bi-119-112LC of the present invention on PD-L1-dependent OX40-mediated signaling pathways, and shows the effect of anti-PD-L1 humanized Nb-Fc, ADI-20112, anti-PD-L1 humanized Nb-Fc+ADI-20112 and IgG1.

The IgG1 negative control used in this example was the same as that used in Example 1.5 above. The experimental results are shown in FIG. 8. In a cell system with PD-L1 expressed, the anti-OX40/PD-L1 bispecific antibody Bi-119-112LC of the present invention has a significant activation effect on the NF-κB signaling pathway, whereas the anti-OX40 antibody ADI-20112 has a lower activation effect on the NF-κB signaling pathway, and the anti-PD-L1 humanized Nb-Fc antibody has no activation effect on the NF-κB signaling pathway. The anti-OX40/PD-L1 bispecific antibody of the present invention has a better activation effect on the NF-κB signaling pathway downstream of OX40 in the presence of PD-L1-expressing cells.

Example 1.9. Thermal Stability Assay of Anti-OX40/PD-L1 Bispecific Antibody of the Present Invention With Differential scanning fluorimetry (DSF), information about protein structure stability can be provided according to the process of fluorescence change in a protein atlas, the configuration change of a protein can be assayed, and the melting temperature ($T_m$) of a protein can be obtained. DSF is adopted in the present example to determine the $T_m$ of anti-OX40/PD-L1 bispecific antibody of the present invention.

The anti-OX40/PD-L1 bispecific antibody Bi-119-112LC of the present invention was diluted to 1 mg/mL in PBS solutions. 196 μL of PBS was added to 4 μL of SYPRO Orange Protein Gel Stain (Gibco, Catalog No.: S6650), so that the SYPRO Orange Protein Gel Stain was 50-fold diluted.

50 μL of the aforementioned solution of the bispecific antibody with a concentration of 1 mg/mL, 10 μL of the aforementioned 50-fold-diluted SYPRO Orange Protein Gel Stain, and 40 μL of water were added to each well of a 96-well PCR plate (Nunc) sequentially. The 96-well PCR plate was put into a 7500 Real Time PCR System (Applied Biosystems, AB/7500) for assay. The temperature of the system was set to rise by 0.5° C./min, and the temperature when a peak absolute value appeared in a fluorescence curve was $T_m$ of the protein.

Figure 9:
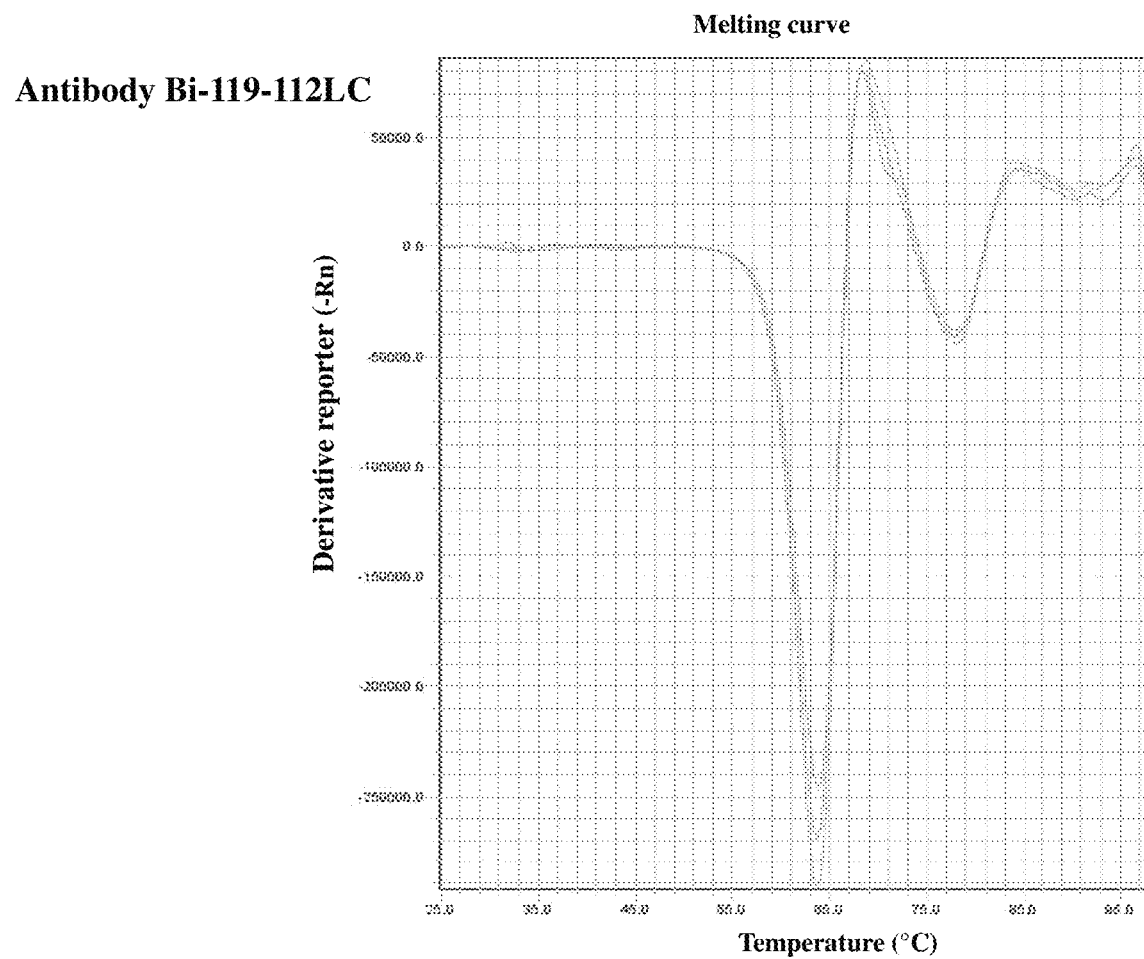
FIG. 9 shows the result of $T_m$ value detected by differential scanning fluorimetry (DSF) of the anti-OX40/PD-L1 bispecific antibody Bi-119-112LC of the present invention.

The experimental results are shown in Table 3 and FIG. 9 below. The bispecific antibody of the present invention has a $T_m$ higher than 60° C., thus having a better thermal stability.

TABLE 3

| $T_m$ of bispecific antibody | | | |
|---|---|---|---|
| Antibody | $T_m$ (° C.) | | Average (° C.) |
| Bi-119-112LC | 63.59   63.59   63.78 | | 63.65 |

Example 1.10. Thermal Stability Assay of the Anti-OX40/PD-L1 Bispecific Antibody of the Present Invention To further confirm the stability of the bispecific antibody, in this example, changes in purity of a batch of prepared antibodies after placing at 40° C. for 0, 1, 3, 7, 10, 20, 30 days were assayed, and thus the long-term thermal stability of the antibody was evaluated. The initial purity of the batch of the prepared antibodies (Bi-119-112LC) was 92.91% as assayed by SEC. The experimental process was as follows: the antibody samples were concentrated to 5 mg/mL (in PBS), then aliquoted into EP tubes at 200 μL/tube and placed at 40° C. in the absence of light. Main peak purity of monomer of the antibody was determined by SEC-HPLC with one tube of sample on day 0, day 1, day 3, day 7, day 10, day 20 and day 30.

The experimental results are shown in Table 4. The anti-OX40/PD-L1 bispecific antibody Bi-119-112LC of the present invention is placed at 40° C. for 30 days, and the main peak of monomer thereof only decreases by 3.69%. The results show that the anti-OX40/PD-L1 bispecific antibody of the present invention has a better thermal stability.

TABLE 4

Changes in proportion of main peak of monomer of bispecific antibody cultivated at 40° C.

| Placed at 40° C. (days) | Bi-119-112LC |
|---|---|
| 0 | 92.91% |
| 1 | 91.51% |
| 3 | 91.10% |
| 7 | 90.93% |
| 10 | 90.45% |
| 20 | 89.72% |
| 30 | 89.22% |

Example 1.11. Assay of Activation Effect of the Anti-OX40/PD-L1 Bispecific Antibody of the Present Invention on Human CD4$^+$ T Cells The activation effect of the anti-OX40/PD-L1 bispecific antibody of the present invention on CD4$^+$ T cells in vitro was assayed in this example. The specific experimental process was as follows:

Human PBMC cells (ALLCELLS, PB005F) were thawed, and let stand for 3 h to give adherent cells (monocytes), then added with 10 mL of AIM V® Medium CTS (GIBCO, A3021002) culture medium. IL4 (20 ng/mL) (R&D, 204-IL) and GM-CSF (10 ng/mL) (R&D, 215-GM) were added to induce monocytes to differentiate into dendritic cells (DC cells). After culturing for 5 days, cytokines inducing maturation of DC (TNFα (1000 U/mL) (R&D, Catalog No.: 210-TA), RhIL-10 (5 ng/mL) (R&D, Catalog No.: 201-LB), RhIL-6 (10 ng/mL) (R&D, Catalog No.: 206-IL), and 1 μM PGE (Tocris, Catalog No.: 2296)) were added. Then the mixture was cultivated for 2 days in a carbon dioxide incubator at 37° C., 5% CO$_2$ as mature DC cells (moDC) of mixed lymphocyte reaction (MLR);

Human PBMC cells (ALLCELLS, Catalog No.: PB005F) were thawed, and CD4$^+$ T cells were isolated according to the instructions of the human CD4$^+$ T cell enrichment kit (STEMCELL, Catalog No.: 19052). Briefly, the aforementioned cell suspension pipetted from the PBMC suspension that had been statically cultivated for 2 h was added to a 20 mL centrifuge tube and centrifuged at 300 g for 10 min. The cell precipitate was resuspended in 500 μL of separating medium and 100 μL of purified antibody provided in the kit, and then incubated at 4° C. for 20 min. The mixture was washed once with separating medium, added with 500 μL of a bead buffer, and then incubated for 15 min. Beads were removed by a magnetic field. The cells were washed once with AIM V® Medium CTS (GIBCO, Catalog No.: A3021002) culture medium. The resulting CD4+ T cells were cultivated with 8 mL of AIM V® Medium CTS culture medium. The resulting cells were added to Dynabeads Human T-Activator CD3/CD28 (INVITROGEN, Catalog No.: 11131D) according to a ratio of CD4+ T cells:anti-CD3/CD28 beads=1:1, and then cultivated for 3 days in a carbon dioxide incubator at 37° C., 5% $CO_2$, to conduct the bead stimulation for CD4+ T cells.

The aforementioned separated DC cells were mixed with CD4+ T cells stimulated by beads, and staphylococcal enterotoxin E superantigen (Toxin technology, Catalog No.: ET404) was added so that the final concentration was adjusted to 1 ng/mL. The mixture was added to wells at 200 μL/well, 12000 DC cells/well, and 120000 CD4+ T cells/well. Then antibody diluted in gradient was added, and the mixture was cultivated for 3 days. The expression level of IL2 in each sample was detected by a Cisbio IL2 detection kit (CISBIO, Catalog No.: 62HIL02PEG), and the activation ability of each antibody on the T cells was reflected by the expression level of IL2 of the antibody.

Figure 10:
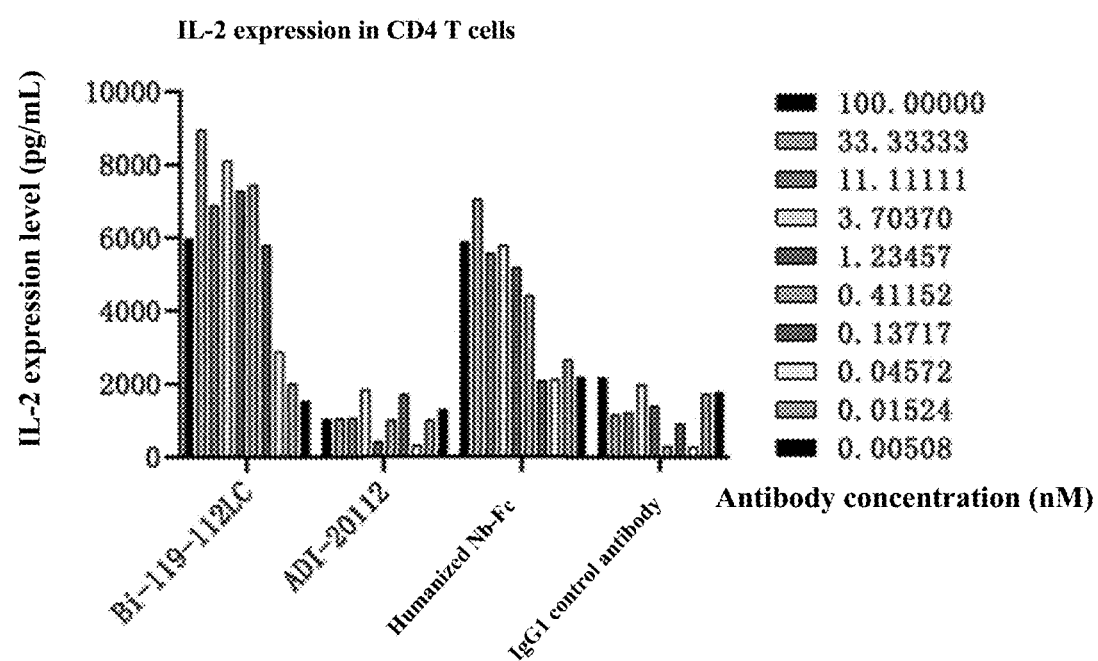
FIG. 10 shows the activation of human T cells by the anti-OX40/PD-L1 bispecific antibody Bi-119-112LC of the present invention, and shows the effect of anti-PD-L1 humanized Nb-Fc, ADI-20112, and IgG1.

The results are shown in FIG. 10. The anti-OX40/PD-L1 bispecific antibody Bi-119-112LC of the present invention can effectively activate human CD4+ T cells in vitro, and the activation effect thereof is better than that of the anti-PD-L1 humanized Nb-Fc antibody and the anti-OX40 antibody ADI-20112.

Figure 11A:
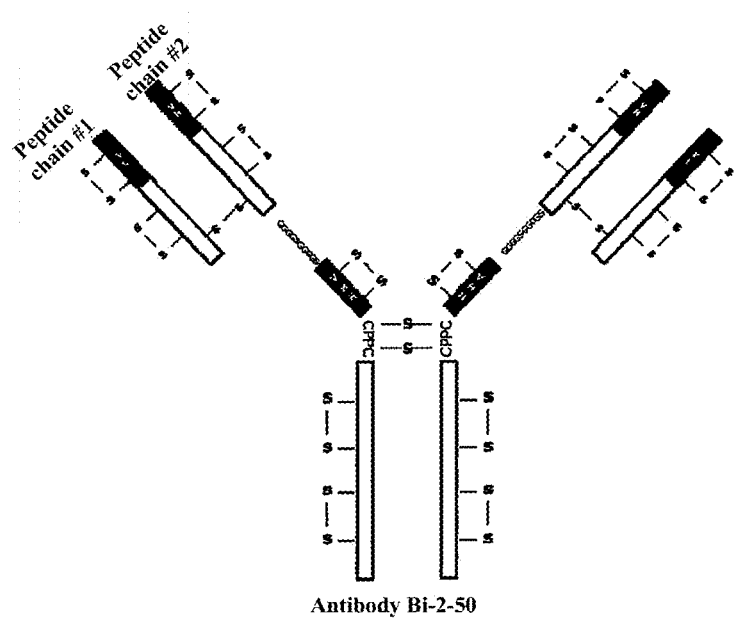
FIGS. 11A-11B illustrate 2 structures of the bispecific antibody of the present invention. The hinge region comprises the amino acid sequence "CPPC" (SEQ ID NO: 32).
Figure 11B:
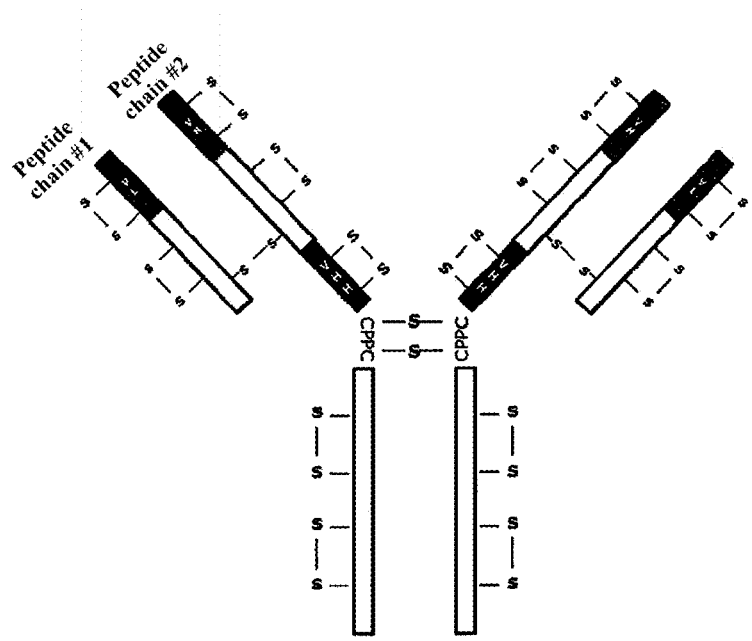

Example 2. Construction, Expression, Purification and Property Identification of Anti-VEGF/GITR Bispecific Antibody Example 2.1. Construction of Anti-VEGF/GITR Bispecific Antibody In this example, two kinds of anti-VEGF/GITR bispecific antibodies with different structures were constructed, and named as (1) bispecific antibody Bi-2-50, the structural schematic diagram of which is shown in FIG. 11A; and (2) the bispecific antibody Bi-2-51, the structural schematic diagram of which is shown in FIG. 11B. The two kinds of anti-VEGF/GITR bispecific antibodies were described below.

(1) As can be seen from the structural schematic diagram of FIG. 11A, the bispecific antibody Bi-2-50 consists of four polypeptide chains that are symmetrical from left to right, wherein, from the N-terminus to the C-terminus, two polypeptide chains in the left half (i.e., peptide chain #1 and peptide chain #2) have the amino acid sequences set forth in SEQ ID NO: 18 and SEQ ID NO: 21, respectively. Specifically, the peptide chain #1 set forth in SEQ ID NO.: 18 comprises a VL amino acid sequence derived from anti-VEGF antibody Avastin set forth in SEQ ID NO: 20 and a human κ light chain constant region (CL) amino acid sequence set forth in SEQ ID NO: 8 and located at the C-terminus of the VL amino acid sequence; the peptide chain #2 set forth in SEQ ID NO: 21 comprises a VH amino acid sequence derived from anti-VEGF monoclonal antibody Avastin set forth in SEQ ID NO: 22, a CH1 amino acid sequence derived from human IgG1 set forth in SEQ ID NO: 23 and located at the C-terminus of the VH amino acid sequence, a linker peptide amino acid sequence set forth in SEQ ID NO: 9 and an anti-GITR VHH amino acid sequence set forth in SEQ ID NO: 24 and located at the C-terminus of the CH1 amino acid sequence, and an Fc region amino acid sequence derived from human IgG 1 set forth in SEQ ID NO: 13.

(2) As can be seen from the structural schematic diagram of FIG. 11B, the bispecific antibody Bi-2-51 consists of four polypeptide chains that are symmetrical from left to right, wherein, from the N-terminus to the C-terminus, two polypeptide chains in the left half (i.e., peptide chain #1 and peptide chain #2) have the amino acid sequences set forth in SEQ ID NO: 18 and SEQ ID NO: 28, respectively. From the N-terminus to the C-terminus, the peptide chain #2 set forth in SEQ ID NO: 28 comprises a VH amino acid sequence derived from the anti-VEGF monoclonal antibody Avastin set forth in SEQ ID NO: 22, a CH1 amino acid sequence derived from human IgG1 set forth in SEQ ID NO: 23, an anti-GITR VHH amino acid sequence set forth in SEQ ID NO: 24 and an Fc region amino acid sequence derived from human IgG1 set forth in SEQ ID NO: 13.

Example 2.2. Expression, Purification and Analysis of Anti-VEGF/GITR Bispecific Antibodies In this example, the nucleotide sequences encoding the peptide chain #1 and peptide chain #2 of the anti-VEGF/GITR bispecific antibodies Bi-2-50 and Bi-2-51 constructed in Example 2.1 were linked to the commercially available eukaryotic expression vector pTT5 via multiple cloning sites, and after expression in eukaryotic cells and purification, anti-VEGF/GITR bispecific antibodies Bi-2-50 and Bi-2-51 were obtained.

Figure 12A:
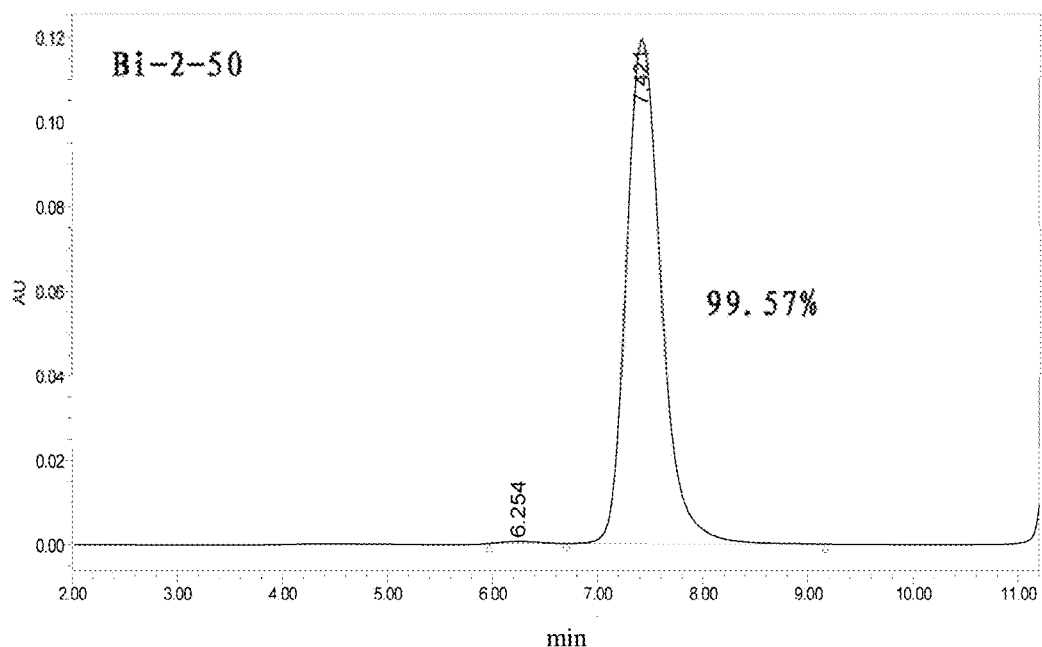
FIGS. 12A-12B respectively show the purity detected by SEC of the anti-VEGF/GITR bispecific antibodies Bi-2-50 and Bi-2-51 prepared herein.
Figure 12B:
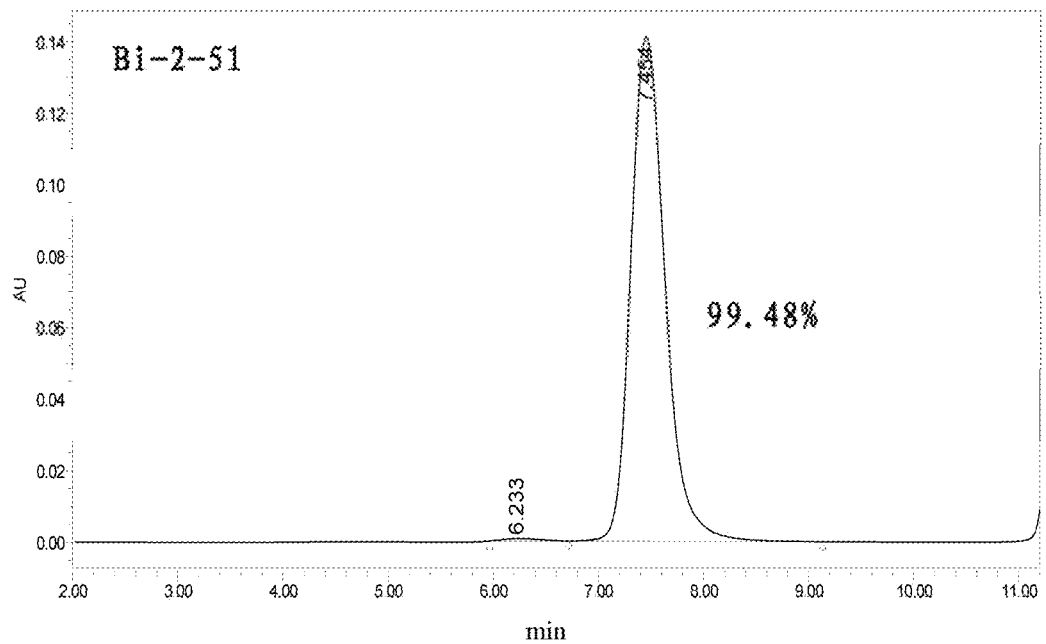

Plasmid transfection, and expression and purification of the anti-VEGF/GITR bispecific antibodies Bi-2-50 and Bi-2-51 were the same as those in Example 1.2. The SEC results of the bispecific antibodies Bi-2-50 and Bi-2-51 are shown in FIG. 12A and FIG. 12B, respectively.

After purification, the anti-VEGF/GITR bispecific antibodies have good purities, with the main peak purities of Bi-2-50 and Bi-2-51 monomers being 99.57% and 99.48%, respectively.

Example 2.3. Determination of Dissociation Constants of Anti-VEGF/GITR Bispecific Antibodies The equilibrium dissociation constant ($K_D$) for the binding of the aforementioned exemplary anti-VEGF/GITR bispecific antibodies Bi-2-50 and Bi-2-51 to VEGF and GITR was determined by a kinetic binding assay using the Octet system (ForteBio). Specific experimental procedures were the same as those in Example 1.3, except that the antibodies and antigens used were different. The results are shown in Tables 5 and 6 below.

An antibody named "hcIgG-10" having an amino acid sequence set forth in SEQ ID NO: 31 comprising, from the N-terminus to the C-terminus, an anti-GITR VHH amino acid sequence set forth in SEQ ID NO: 24, a "DKTHT" peptide fragment and the Fc region amino acid sequence derived from human IgG1 set forth in SEQ ID NO: 13, was used as a parent monospecific antibody against GITR.

TABLE 5

Affinity of anti-VEGF/GITR bispecific antibodies to GITR determined by ForteBio kinetic binding assay

| Antibody | Antibodies on AHC tip/human GITR-His in solution (50 nM) (monovalent affinity (M)) | Binding constant $K_{on}$ ($M^{-1} s^{-1}$) | Dissociation constant $k_{dis}$ ($s^{-1}$) |
|---|---|---|---|
| hcIgG-10 | 2.57E−09 | 2.34E+05 | 6.02E−04 |
| Bi-2-50 | 2.39E−09 | 2.63E+05 | 6.29E−04 |
| Bi-2-51 | 2.31E−09 | 2.54E+05 | 5.85E−04 |

TABLE 6

Affinity of anti-VEGF/GITR bispecific antibodies to VEGF165 determined by ForteBio kinetic binding assay

| Antibody | Antibodies on AHC tip/human VEGF165 in solution (50 nM) (monovalent affinity (M)) | Binding constant $K_{on}$ ($M^{-1} s^{-1}$) | Dissociation constant $k_{dis}$ ($s^{-1}$) |
|---|---|---|---|
| Bi-2-50 | 1.08E−09 | 1.24E+05 | 1.35E−04 |
| Bi-2-51 | 7.70E−10 | 1.49E+05 | 1.15E−04 |
| Avastin | 4.53E−10 | 1.48E+05 | 6.73E−05 |

It can be seen from the data in Tables 5 and 6 that the anti-VEGF/GITR bispecific antibodies Bi-2-50 and Bi-2-51 of the present invention, are both able to bind to VEGF165 (R&D, 293-VE-500) and GITR (AcroBiosystems, GIR-H5228-1MG) proteins in solution, and maintain the affinity constants of the parental antibody Avastin or hcIgG-10.

Example 2.4. Analysis on Binding of the Anti-VEGF/GITR Bispecific Antibody of the Present Invention to CHO Cells Overexpressing VEGF or GITR The binding of the anti-VEGF/GITR bispecific antibodies Bi-2-50 and Bi-2-51 of the present invention to CHO cells overexpressing VEGF or GITR was determined by FACS. Specific experimental procedures were the same as those in Example 1.4, except that the antibodies and antigens used are different. The IgG1 negative control used in this example was the same as that used in Example 1.5 above. The results are shown in FIG. 13.

Figure 13:
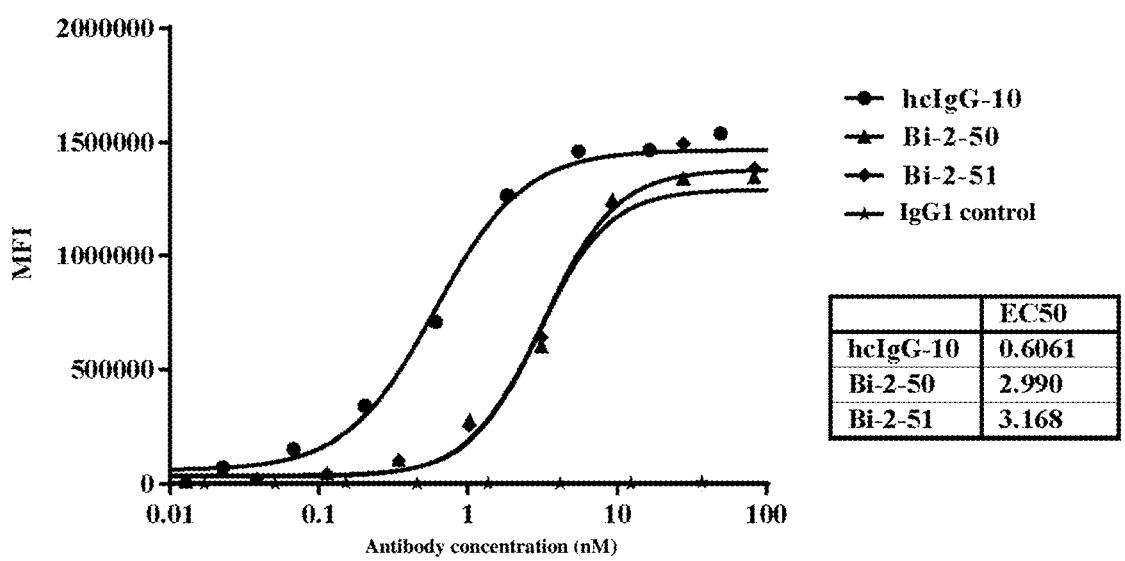
FIG. 13 shows the binding detected by FACS of the anti-VEGF/GITR bispecific antibodies Bi-2-50 and Bi-2-51 to CHO cells overexpressing GITR. The horizontal axis represents the antibody concentration, and the vertical axis represents the mean fluorescence intensity (MFI).

It can be seen from FIG. 13 that the anti-VEGF/GITR bispecific antibodies Bi-2-50 and Bi-2-51 of the present invention are both able to bind to GITR expressed on cell surface with binding $EC_{50}$ of 2.990 nM and 3.168 nM, respectively. The parent antibody hcIgG-10 binds to GITR on cell surface with an $EC_{50}$ of 0.6061 nM.

Although certain representative embodiments and details have been shown for the purpose of illustrating the present invention, it will be apparent to those skilled in the art that various variations and modifications can be made to these embodiments and details without departing from the scope of the subject matter of the present invention. In this respect, the scope of the present invention is limited only by the following claims.

---

The invention claimed is:

1. An antibody molecule, wherein the antibody molecule is an anti-OX40/PD-L1 bispecific antibody, comprising four polypeptide chains, wherein a first polypeptide chain and a second polypeptide chain are paired, wherein a third polypeptide chain and a fourth polypeptide chain are paired, wherein each of the first polypeptide chain and the third polypeptide chain is an immunoglobulin light chain comprising, from the N-terminus to the C-terminus, a light chain variable region and constant domain, and each of the second polypeptide chain and the fourth polypeptide chain comprises, from the N-terminus to the C-terminus, an immunoglobulin heavy chain variable region, an immunoglobulin CH1 domain, a single-domain antigen-binding site VHH, an immunoglobulin CH2 domain, an immunoglobulin CH3 domain, and optionally an immunoglobulin CH4 domain, wherein the immunoglobulin CH2 domain, the immunoglobulin CH3 domain, and optionally the immunoglobulin CH4 domain form an Fc domain;
wherein the VHH specifically binds to PD-L1, the VHH comprising three heavy chain complementarity determining regions (CDRs) set forth in SEQ ID NO: 3, SEQ ID NO: 4 and SEQ ID NO: 5, respectively;
and wherein the immunoglobulin light chain and its paired immunoglobulin heavy chain variable region and immunoglobulin CH1 domain form an Fab fragment which specifically binds to OX40, and wherein the Fab fragment comprises (i) the three heavy chain CDRs of SEQ ID NO: 11, and (ii) the three light chain CDRs of SEQ ID NO: 7.

2. The antibody molecule of claim 1, wherein the immunoglobulin heavy chain constant domains are of an IgG1 immunoglobulin isotype, an IgG2 immunoglobulin isotype, or an IgG4 immunoglobulin isotype, wherein the immunoglobulin light chain is of κ type or λ type.

3. The antibody molecule of claim 1, wherein the Fc domain comprises a hinge region in an immunoglobulin constant portion, and heavy chains of the antibody molecule stably associate with each other via disulfide bonds in the hinge region; optionally, the heavy chain of the antibody molecule comprises a hinge region of "CPPC" (SEQ ID NO: 32) amino acid residues in the Fc domain, such that the heavy chains stably associate with each other via disulfide bonds formed between the amino acid residues in the hinge regions;
optionally, the second polypeptide chain and the fourth polypeptide chain further comprise Y349C and S354C, respectively, or S354C and Y349C, respectively according to the Kabat EU numbering system, such that the heavy chains of the antibody molecule further form inter-chain disulfide bonds with each other in the Fc domain,
optionally, the Fc domain further comprises a mutation that affects effector functions of an antibody, optionally, an LALA mutation.

4. The antibody molecule of claim 1, wherein the Fc domains of the heavy chains of the antibody molecule respectively comprise a protuberance and a cavity, and the protuberance or cavity in the Fc domain of one heavy chain is able to be respectively placed at the cavity or protuberance in the Fc domain of the other heavy chain, such that the heavy chains of the antibody molecule form a "knob-in-hole" stable association with each other; optionally, the immunoglobulin CH1 domain and the light chain constant domain (CL) respectively comprise a protuberance and a cavity, or vice versa, and the protuberance or cavity in the CH1 domain is able to be respectively placed at the cavity or protuberance in the CL domain, such that the heavy and light chains of the antibody molecule form a "knob-in-hole" stable association with each other.

5. The antibody molecule of claim 1, wherein a linker peptide connects the VHH and the Fab fragment, wherein the linker peptide comprises glycine and/or serine residues; optionally, the linker peptide comprises the amino acid sequence (Gly$_4$Ser)n, wherein n is a positive integer ranging from 1 to 7.

6. The antibody molecule of claim 1, wherein the VHH comprises the amino acid sequence set forth in SEQ ID NO: 1 or SEQ ID NO: 2, or a sequence at least 95% identical thereto, and the Fab fragment comprises the heavy chain and light chain variable region sequences of the anti-OX40 antibody set forth in SEQ ID NOs: 11 and 7, respectively, or sequences at least 95% identical thereto;

optionally, the sequence of each of the first polypeptide chain and the third polypeptide chain is set forth in SEQ ID NO: 15, or a sequence at least 95% identical thereto, and the sequence of each of the second polypeptide chain and the fourth polypeptide chain is set forth in SEQ ID NO: 16, or a sequence at least 95% identical thereto.

7. A pharmaceutical composition, comprising the antibody molecule of claim 1 and a pharmaceutically acceptable carrier.

8. A pharmaceutical composition, comprising the antibody molecule of claim 6 a pharmaceutically acceptable carrier.

* * * * *

SEQUENCE LISTING

```
<160> NUMBER OF SEQ ID NOS: 32

<210> SEQ ID NO 1
<211> LENGTH: 132
<212> TYPE: PRT
<213> ORGANISM: Camelus Linnaeus

<400> SEQUENCE: 1

Gln Val Gln Leu Gln Glu Ser Gly Gly Gly Ser Val Gln Ala Gly Gly
1               5                   10                  15

Ser Leu Arg Leu Ser Cys Gln Ala Ser Ala Tyr Thr Ile Ser Arg Asn
            20                  25                  30

Ser Met Gly Trp Phe Arg Gln Ala Pro Gly Lys Gln Arg Glu Gly Val
        35                  40                  45

Ala Ala Ile Glu Ser Asp Gly Ser Thr Ser Tyr Ser Asp Ser Val Lys
    50                  55                  60

Gly Arg Phe Thr Ile Ser Leu Gly Asn Ala Lys Asn Thr Leu Tyr Leu
65                  70                  75                  80

Glu Met Asn Ser Leu Lys Pro Glu Asp Thr Ala Met Tyr Tyr Cys Ala
                85                  90                  95

Ala Pro Lys Val Gly Leu Gly Pro Arg Thr Ala Leu Gly His Leu Ala
            100                 105                 110

Phe Met Thr Leu Pro Ala Leu Asn Tyr Trp Gly Gln Gly Thr Gln Val
        115                 120                 125

Thr Val Ser Ser
    130

<210> SEQ ID NO 2
<211> LENGTH: 132
<212> TYPE: PRT
```

<213> ORGANISM: Artificial sequence
<220> FEATURE:
<223> OTHER INFORMATION: Humanized VHH of anti-PD-L1 antibody

<400> SEQUENCE: 2

Gln Val Gln Leu Gln Glu Ser Gly Gly Gly Leu Val Gln Pro Gly Gly
1               5                   10                  15

Ser Leu Arg Leu Ser Cys Ala Ala Ser Ala Tyr Thr Ile Ser Arg Asn
            20                  25                  30

Ser Met Gly Trp Phe Arg Gln Ala Pro Gly Lys Gly Leu Glu Gly Val
        35                  40                  45

Ala Ala Ile Glu Ser Asp Gly Ser Thr Ser Tyr Ser Asp Ser Val Lys
50                  55                  60

Gly Arg Phe Thr Ile Ser Leu Asp Asn Ser Lys Asn Thr Leu Tyr Leu
65                  70                  75                  80

Glu Met Asn Ser Leu Arg Ala Glu Asp Thr Ala Val Tyr Tyr Cys Ala
                85                  90                  95

Ala Pro Lys Val Gly Leu Gly Pro Arg Thr Ala Leu Gly His Leu Ala
            100                 105                 110

Phe Met Thr Leu Pro Ala Leu Asn Tyr Trp Gly Gln Gly Thr Leu Val
        115                 120                 125

Thr Val Ser Ser
    130

<210> SEQ ID NO 3
<211> LENGTH: 10
<212> TYPE: PRT
<213> ORGANISM: Camelus Linnaeus

<400> SEQUENCE: 3

Ala Tyr Thr Ile Ser Arg Asn Ser Met Gly
1               5                   10

<210> SEQ ID NO 4
<211> LENGTH: 7
<212> TYPE: PRT
<213> ORGANISM: Camelus Linnaeus

<400> SEQUENCE: 4

Ile Glu Ser Asp Gly Ser Thr
1               5

<210> SEQ ID NO 5
<211> LENGTH: 26
<212> TYPE: PRT
<213> ORGANISM: Camelus Linnaeus

<400> SEQUENCE: 5

Ala Ala Pro Lys Val Gly Leu Gly Pro Arg Thr Ala Leu Gly His Leu
1               5                   10                  15

Ala Phe Met Thr Leu Pro Ala Leu Asn Tyr
            20                  25

<210> SEQ ID NO 6
<211> LENGTH: 355
<212> TYPE: PRT
<213> ORGANISM: Artificial Sequence
<220> FEATURE:
<223> OTHER INFORMATION: Amino acid sequence of the peptide chain #1 of
      the anti-OX40/PD-L1 bispecific antibody Bi-110-112HC

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp His Tyr Pro Thr
                85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys Gly Gly Gly Ser Gly Gly Gly Ser Gln
210                 215                 220

Val Gln Leu Gln Glu Ser Gly Gly Leu Val Gln Pro Gly Gly Ser
225                 230                 235                 240

Leu Arg Leu Ser Cys Ala Ala Ser Ala Tyr Thr Ile Ser Arg Asn Ser
            245                 250                 255

Met Gly Trp Phe Arg Gln Ala Pro Gly Lys Gly Leu Glu Gly Val Ala
        260                 265                 270

Ala Ile Glu Ser Asp Gly Ser Thr Ser Tyr Ser Asp Ser Val Lys Gly
        275                 280                 285

Arg Phe Thr Ile Ser Leu Asp Asn Ser Lys Asn Thr Leu Tyr Leu Glu
    290                 295                 300

Met Asn Ser Leu Arg Ala Glu Asp Thr Ala Val Tyr Tyr Cys Ala Ala
305                 310                 315                 320

Pro Lys Val Gly Leu Gly Pro Arg Thr Ala Leu Gly His Leu Ala Phe
                325                 330                 335

Met Thr Leu Pro Ala Leu Asn Tyr Trp Gly Gln Gly Thr Leu Val Thr
            340                 345                 350

Val Ser Ser
        355

<210> SEQ ID NO 7
<211> LENGTH: 106
<212> TYPE: PRT
<213> ORGANISM: Artificial Sequence
<220> FEATURE:
<223> OTHER INFORMATION: VL amino acid sequence of the anti-OX40
      antibody ADI-20112

```
<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp His Tyr Pro Thr
                85                  90                  95

Phe Gly Gly Gly Thr Lys Val Glu Ile Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: Human ? light chain constant region (CL) amino
      acid sequence

<400> SEQUENCE: 8

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 9
<211> LENGTH: 10
<212> TYPE: PRT
<213> ORGANISM: Artificial Sequence
<220> FEATURE:
<223> OTHER INFORMATION: Linker peptide amino acid sequence

<400> SEQUENCE: 9

Gly Gly Gly Gly Ser Gly Gly Gly Gly Ser
1               5                   10

<210> SEQ ID NO 10
<211> LENGTH: 454
<212> TYPE: PRT
<213> ORGANISM: Artificial Sequence
<220> FEATURE:
<223> OTHER INFORMATION: Amino acid sequence of the peptide chain #2 of
      the anti-OX40/PD-L1 bispecific antibody Bi-110-112HC

<400> SEQUENCE: 10
```

-continued

Gln Val Gln Leu Val Glu Ser Gly Gly Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Trp Tyr Ser Glu Thr Gly Thr Ser Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
        180                 185                 190

Val Thr Val Pro Ser Ser Leu Gly Thr Gln Thr Tyr Ile Cys Asn
            195                 200                 205

Val Asn His Lys Pro Ser Asn Thr Lys Val Asp Lys Lys Ala Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
        340                 345                 350

Pro Gln Val Tyr Thr Leu Pro Pro Ser Arg Asp Glu Leu Thr Lys Asn
    355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys

```
                420                 425                 430
Ser Val Met His Glu Ala Leu His Asn His Tyr Thr Gln Lys Ser Leu
        435                 440                 445

Ser Leu Ser Pro Gly Lys
        450

<210> SEQ ID NO 11
<211> LENGTH: 124
<212> TYPE: PRT
<213> ORGANISM: Artificial Sequence
<220> FEATURE:
<223> OTHER INFORMATION: VH amino acid sequence of the anti-OX40
      monoclonal antibody ADI-20112

<400> SEQUENCE: 11

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Trp Tyr Ser Glu Thr Gly Thr Ser Ala Phe Asp
            100                 105                 110

Ile Trp Gly Gln Gly Thr Met Val Thr Val Ser Ser
        115                 120

<210> SEQ ID NO 12
<211> LENGTH: 108
<212> TYPE: PRT
<213> ORGANISM: Artificial Sequence
<220> FEATURE:
<223> OTHER INFORMATION: CH1 amino acid sequence of human IgG1

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr
            100                 105

<210> SEQ ID NO 13
<211> LENGTH: 222
<212> TYPE: PRT
<213> ORGANISM: Artificial Sequence
```

<220> FEATURE:
<223> OTHER INFORMATION: Fc region amino acid sequence of human IgG1

<400> SEQUENCE: 13

```
Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220
```

<210> SEQ ID NO 14
<211> LENGTH: 355
<212> TYPE: PRT
<213> ORGANISM: Artificial Sequence
<220> FEATURE:
<223> OTHER INFORMATION: Amino acid sequence of the peptide chain #1 of the anti-OX40/PD-L1 bispecific antibody Bi-113-112HC

<400> SEQUENCE: 14

```
Gln Val Gln Leu Gln Glu Ser Gly Gly Gly Leu Val Gln Pro Gly Gly
1               5                   10                  15

Ser Leu Arg Leu Ser Cys Ala Ala Ser Ala Tyr Thr Ile Ser Arg Asn
            20                  25                  30

Ser Met Gly Trp Phe Arg Gln Ala Pro Gly Lys Gly Leu Glu Gly Val
        35                  40                  45

Ala Ala Ile Glu Ser Asp Gly Ser Thr Ser Tyr Ser Asp Ser Val Lys
    50                  55                  60

Gly Arg Phe Thr Ile Ser Leu Asp Asn Ser Lys Asn Thr Leu Tyr Leu
65                  70                  75                  80

Glu Met Asn Ser Leu Arg Ala Glu Asp Thr Ala Val Tyr Tyr Cys Ala
                85                  90                  95

Ala Pro Lys Val Gly Leu Gly Pro Arg Thr Ala Leu Gly His Leu Ala
            100                 105                 110
```

```
Phe Met Thr Leu Pro Ala Leu Asn Tyr Trp Gly Gln Gly Thr Leu Val
            115                 120                 125

Thr Val Ser Ser Gly Gly Gly Ser Gly Gly Gly Ser Asp Ile
130                 135                 140

Gln Met Thr Gln Ser Pro Ser Ser Leu Ser Ala Ser Val Gly Asp Arg
145                 150                 155                 160

Val Thr Ile Thr Cys Gln Ala Ser Gln Asp Ile Ser Asn Tyr Leu Asn
                165                 170                 175

Trp Tyr Gln Gln Lys Pro Gly Lys Ala Pro Lys Leu Leu Ile Tyr Asp
            180                 185                 190

Ala Ser Asn Leu Glu Thr Gly Val Pro Ser Arg Phe Ser Gly Ser Gly
        195                 200                 205

Ser Gly Thr Asp Phe Thr Phe Thr Ile Ser Ser Leu Gln Pro Glu Asp
210                 215                 220

Ile Ala Thr Tyr Tyr Cys Gln Gln Ser Asp His Tyr Pro Thr Phe Gly
225                 230                 235                 240

Gly Gly Thr Lys Val Glu Ile Lys Arg Thr Val Ala Ala Pro Ser Val
                245                 250                 255

Phe Ile Phe Pro Pro Ser Asp Glu Gln Leu Lys Ser Gly Thr Ala Ser
            260                 265                 270

Val Val Cys Leu Leu Asn Asn Phe Tyr Pro Arg Glu Ala Lys Val Gln
        275                 280                 285

Trp Lys Val Asp Asn Ala Leu Gln Ser Gly Asn Ser Gln Glu Ser Val
    290                 295                 300

Thr Glu Gln Asp Ser Lys Asp Ser Thr Tyr Ser Leu Ser Ser Thr Leu
305                 310                 315                 320

Thr Leu Ser Lys Ala Asp Tyr Glu Lys His Lys Val Tyr Ala Cys Glu
                325                 330                 335

Val Thr His Gln Gly Leu Ser Ser Pro Val Thr Lys Ser Phe Asn Arg
            340                 345                 350

Gly Glu Cys
        355

<210> SEQ ID NO 15
<211> LENGTH: 213
<212> TYPE: PRT
<213> ORGANISM: Artificial Sequence
<220> FEATURE:
<223> OTHER INFORMATION: Amino acid sequence of the peptide chain #1 of
      the anti-OX40/PD-L1 bispecific antibody Bi-119-112LC

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp His Tyr Pro Thr
                85                  90                  95

Phe Gly Gly Gly Thr Lys Val Glu Ile Lys Arg Thr Val Ala Ala Pro
            100                 105                 110
```

```
Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 16
<211> LENGTH: 588
<212> TYPE: PRT
<213> ORGANISM: Artificial Sequence
<220> FEATURE:
<223> OTHER INFORMATION: Amino acid sequence of the peptide chain #2 of
      the anti-OX40/PD-L1 bispecific antibody Bi-119-112LC

<400> SEQUENCE: 16

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Trp Tyr Ser Glu Thr Gly Thr Ser Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Ala Glu Pro
    210                 215                 220

Lys Ser Cys Asp Lys Gln Val Gln Leu Gln Glu Ser Gly Gly Gly Leu
225                 230                 235                 240

Val Gln Pro Gly Gly Ser Leu Arg Leu Ser Cys Ala Ala Ser Ala Tyr
```

```
                    245                 250                 255
Thr Ile Ser Arg Asn Ser Met Gly Trp Phe Arg Gln Ala Pro Gly Lys
            260                 265                 270
Gly Leu Glu Gly Val Ala Ala Ile Glu Ser Asp Gly Ser Thr Ser Tyr
        275                 280                 285
Ser Asp Ser Val Lys Gly Arg Phe Thr Ile Ser Leu Asp Asn Ser Lys
    290                 295                 300
Asn Thr Leu Tyr Leu Glu Met Asn Ser Leu Arg Ala Glu Asp Thr Ala
305                 310                 315                 320
Val Tyr Tyr Cys Ala Ala Pro Lys Val Gly Leu Gly Pro Arg Thr Ala
                325                 330                 335
Leu Gly His Leu Ala Phe Met Thr Leu Pro Ala Leu Asn Tyr Trp Gly
            340                 345                 350
Gln Gly Thr Leu Val Thr Val Ser Ser Asp Lys Thr His Thr Cys Pro
        355                 360                 365
Pro Cys Pro Ala Pro Glu Leu Leu Gly Gly Pro Ser Val Phe Leu Phe
    370                 375                 380
Pro Pro Lys Pro Lys Asp Thr Leu Met Ile Ser Arg Thr Pro Glu Val
385                 390                 395                 400
Thr Cys Val Val Val Asp Val Ser His Glu Asp Pro Glu Val Lys Phe
                405                 410                 415
Asn Trp Tyr Val Asp Gly Val Glu Val His Asn Ala Lys Thr Lys Pro
            420                 425                 430
Arg Glu Glu Gln Tyr Asn Ser Thr Tyr Arg Val Val Ser Val Leu Thr
        435                 440                 445
Val Leu His Gln Asp Trp Leu Asn Gly Lys Glu Tyr Lys Cys Lys Val
    450                 455                 460
Ser Asn Lys Ala Leu Pro Ala Pro Ile Glu Lys Thr Ile Ser Lys Ala
465                 470                 475                 480
Lys Gly Gln Pro Arg Glu Pro Gln Val Tyr Thr Leu Pro Pro Ser Arg
                485                 490                 495
Asp Glu Leu Thr Lys Asn Gln Val Ser Leu Thr Cys Leu Val Lys Gly
            500                 505                 510
Phe Tyr Pro Ser Asp Ile Ala Val Glu Trp Glu Ser Asn Gly Gln Pro
        515                 520                 525
Glu Asn Asn Tyr Lys Thr Thr Pro Pro Val Leu Asp Ser Asp Gly Ser
    530                 535                 540
Phe Phe Leu Tyr Ser Lys Leu Thr Val Asp Lys Ser Arg Trp Gln Gln
545                 550                 555                 560
Gly Asn Val Phe Ser Cys Ser Val Met His Glu Ala Leu His Asn His
                565                 570                 575
Tyr Thr Gln Lys Ser Leu Ser Leu Ser Pro Gly Lys
            580                 585

<210> SEQ ID NO 17
<211> LENGTH: 596
<212> TYPE: PRT
<213> ORGANISM: Artificial Sequence
<220> FEATURE:
<223> OTHER INFORMATION: Amino acid sequence of the peptide chain #2 of
      the anti-OX40/PD-L1 bispecific antibody Bi-122-112LC

<400> SEQUENCE: 17

Gln Val Gln Leu Gln Glu Ser Gly Gly Gly Leu Val Gln Pro Gly Gly
1               5                   10                  15
```

```
Ser Leu Arg Leu Ser Cys Ala Ala Ser Ala Tyr Thr Ile Ser Arg Asn
            20                  25                  30

Ser Met Gly Trp Phe Arg Gln Ala Pro Gly Lys Gly Leu Glu Gly Val
            35                  40                  45

Ala Ala Ile Glu Ser Asp Gly Ser Thr Ser Tyr Ser Asp Ser Val Lys
 50                      55                  60

Gly Arg Phe Thr Ile Ser Leu Asp Asn Ser Lys Asn Thr Leu Tyr Leu
 65                  70                  75                  80

Glu Met Asn Ser Leu Arg Ala Glu Asp Thr Ala Val Tyr Tyr Cys Ala
                85                  90                  95

Ala Pro Lys Val Gly Leu Gly Pro Arg Thr Ala Leu Gly His Leu Ala
                100                 105                 110

Phe Met Thr Leu Pro Ala Leu Asn Tyr Trp Gly Gln Gly Thr Leu Val
            115                 120                 125

Thr Val Ser Ser Gly Gly Gly Gly Ser Gly Gly Gly Gly Ser Gln Val
        130                 135                 140

Gln Leu Val Glu Ser Gly Gly Gly Val Val Gln Pro Gly Arg Ser Leu
145                 150                 155                 160

Arg Leu Ser Cys Ala Ala Ser Gly Phe Thr Phe Ser Ser Tyr Gly Met
                165                 170                 175

His Trp Val Arg Gln Ala Pro Gly Lys Gly Leu Glu Trp Val Ala Val
            180                 185                 190

Ile Ser Tyr Asp Gly Ser Asn Lys Tyr Tyr Ala Asp Ser Val Lys Gly
                195                 200                 205

Arg Phe Thr Ile Ser Arg Asp Asn Ser Lys Asn Thr Leu Tyr Leu Gln
210                 215                 220

Met Asn Ser Leu Arg Ala Glu Asp Thr Ala Val Tyr Tyr Cys Ala Arg
225                 230                 235                 240

Gly Arg Pro Trp Tyr Ser Glu Thr Gly Thr Ser Ala Phe Asp Ile Trp
                245                 250                 255

Gly Gln Gly Thr Met Val Thr Val Ser Ser Ala Ser Thr Lys Gly Pro
                260                 265                 270

Ser Val Phe Pro Leu Ala Pro Ser Ser Lys Ser Thr Ser Gly Gly Thr
            275                 280                 285

Ala Ala Leu Gly Cys Leu Val Lys Asp Tyr Phe Pro Glu Pro Val Thr
290                 295                 300

Val Ser Trp Asn Ser Gly Ala Leu Thr Ser Gly Val His Thr Phe Pro
305                 310                 315                 320

Ala Val Leu Gln Ser Ser Gly Leu Tyr Ser Leu Ser Ser Val Val Thr
                325                 330                 335

Val Pro Ser Ser Ser Leu Gly Thr Gln Thr Tyr Ile Cys Asn Val Asn
            340                 345                 350

His Lys Pro Ser Asn Thr Lys Val Asp Lys Ala Glu Pro Lys Ser
            355                 360                 365

Cys Asp Lys Thr His Thr Cys Pro Pro Cys Ala Pro Glu Leu Leu
            370                 375                 380

Gly Gly Pro Ser Val Phe Leu Phe Pro Pro Lys Pro Lys Asp Thr Leu
385                 390                 395                 400

Met Ile Ser Arg Thr Pro Glu Val Thr Cys Val Val Val Asp Val Ser
                405                 410                 415

His Glu Asp Pro Glu Val Lys Phe Asn Trp Tyr Val Asp Gly Val Glu
                420                 425                 430

Val His Asn Ala Lys Thr Lys Pro Arg Glu Glu Gln Tyr Asn Ser Thr
```

```
                   435                 440                 445
Tyr Arg Val Val Ser Val Leu Thr Val Leu His Gln Asp Trp Leu Asn
450                         455                 460

Gly Lys Glu Tyr Lys Cys Lys Val Ser Asn Lys Ala Leu Pro Ala Pro
465                     470                  475                 480

Ile Glu Lys Thr Ile Ser Lys Ala Lys Gly Gln Pro Arg Glu Pro Gln
                    485                 490                 495

Val Tyr Thr Leu Pro Pro Ser Arg Asp Glu Leu Thr Lys Asn Gln Val
                500                 505                 510

Ser Leu Thr Cys Leu Val Lys Gly Phe Tyr Pro Ser Asp Ile Ala Val
            515                 520                 525

Glu Trp Glu Ser Asn Gly Gln Pro Glu Asn Asn Tyr Lys Thr Thr Pro
        530                 535                 540

Pro Val Leu Asp Ser Asp Gly Ser Phe Phe Leu Tyr Ser Lys Leu Thr
545                 550                 555                 560

Val Asp Lys Ser Arg Trp Gln Gln Gly Asn Val Phe Ser Cys Ser Val
                565                 570                 575

Met His Glu Ala Leu His Asn His Tyr Thr Gln Lys Ser Leu Ser Leu
            580                 585                 590

Ser Pro Gly Lys
        595

<210> SEQ ID NO 18
<211> LENGTH: 214
<212> TYPE: PRT
<213> ORGANISM: Artificial Sequence
<220> FEATURE:
<223> OTHER INFORMATION: Amino acid sequence of the peptide chain #1 of
      the anti-VEGF/GITR bispecific antibody Bi-2-50

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

-continued

Ala Cys Glu Val Thr His Gln Gly Leu Ser Ser Pro Val Thr Lys Ser
            195                 200                 205

Phe Asn Arg Gly Glu Cys
    210

<210> SEQ ID NO 19
<211> LENGTH: 453
<212> TYPE: PRT
<213> ORGANISM: Artificial Sequence
<220> FEATURE:
<223> OTHER INFORMATION: Heavy chain amino acid sequence of the
      anti-VEGF antibody Avastin

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

```
Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
435                 440                 445

Leu Ser Pro Gly Lys
            450

<210> SEQ ID NO 20
<211> LENGTH: 107
<212> TYPE: PRT
<213> ORGANISM: Artificial Sequence
<220> FEATURE:
<223> OTHER INFORMATION: Light chain amino acid sequence of the
      anti-VEGF antibody Avastin

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105

<210> SEQ ID NO 21
<211> LENGTH: 581
<212> TYPE: PRT
<213> ORGANISM: Artificial Sequence
<220> FEATURE:
<223> OTHER INFORMATION: Amino acid sequence of the peptide chain #2 of
      the anti-VEGF/GITR bispecific antibody Bi-2-50

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
50                  55                  60
```

```
Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Gly Gly Gly Ser Gly Gly Gly Gly Ser Gln Val
225                 230                 235                 240

Gln Leu Gln Glu Ser Gly Gly Gly Leu Val Gln Pro Gly Gly Ser Leu
                245                 250                 255

Arg Leu Ser Cys Ala Ala Ser Gly Phe Ala Phe Gly Ser Ser His Met
            260                 265                 270

Ser Trp Val Arg Arg Ala Pro Gly Lys Gly Leu Glu Trp Val Ser Thr
        275                 280                 285

Ile His Ser Gly Gly Gly Phe Gly Asp Tyr Ala Asn Ser Val Gln Gly
290                 295                 300

Arg Phe Thr Ile Ser Arg Asp Val Ala Lys Asn Thr Leu Tyr Leu Gln
305                 310                 315                 320

Met Asn Ser Leu Lys Pro Glu Asp Thr Ala Ile Tyr Tyr Cys Ala Leu
                325                 330                 335

Ala Thr Asp Trp Arg Lys Pro Pro Gly Gln Gly Thr Gln Val Thr Val
            340                 345                 350

Ser Ser Asp Lys Thr His Thr Cys Pro Pro Cys Pro Ala Pro Glu Leu
        355                 360                 365

Leu Gly Gly Pro Ser Val Phe Leu Phe Pro Pro Lys Pro Lys Asp Thr
        370                 375                 380

Leu Met Ile Ser Arg Thr Pro Glu Val Thr Cys Val Val Val Asp Val
385                 390                 395                 400

Ser His Glu Asp Pro Glu Val Lys Phe Asn Trp Tyr Val Asp Gly Val
                405                 410                 415

Glu Val His Asn Ala Lys Thr Lys Pro Arg Glu Gln Tyr Asn Ser
            420                 425                 430

Thr Tyr Arg Val Val Ser Val Leu Thr Val Leu His Gln Asp Trp Leu
        435                 440                 445

Asn Gly Lys Glu Tyr Lys Cys Lys Val Ser Asn Lys Ala Leu Pro Ala
        450                 455                 460

Pro Ile Glu Lys Thr Ile Ser Lys Ala Lys Gly Gln Pro Arg Glu Pro
465                 470                 475                 480
```

```
Gln Val Tyr Thr Leu Pro Pro Ser Arg Asp Glu Leu Thr Lys Asn Gln
            485                 490                 495

Val Ser Leu Thr Cys Leu Val Lys Gly Phe Tyr Pro Ser Asp Ile Ala
        500                 505                 510

Val Glu Trp Glu Ser Asn Gly Gln Pro Glu Asn Asn Tyr Lys Thr Thr
            515                 520                 525

Pro Pro Val Leu Asp Ser Asp Gly Ser Phe Phe Leu Tyr Ser Lys Leu
        530                 535                 540

Thr Val Asp Lys Ser Arg Trp Gln Gln Gly Asn Val Phe Ser Cys Ser
545                 550                 555                 560

Val Met His Glu Ala Leu His Asn His Tyr Thr Gln Lys Ser Leu Ser
            565                 570                 575

Leu Ser Pro Gly Lys
            580

<210> SEQ ID NO 22
<211> LENGTH: 123
<212> TYPE: PRT
<213> ORGANISM: Artificial Sequence
<220> FEATURE:
<223> OTHER INFORMATION: VH amino acid sequence of the anti-VEGF
      monoclonal antibody Avastin

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
            85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
            115                 120

<210> SEQ ID NO 23
<211> LENGTH: 105
<212> TYPE: PRT
<213> ORGANISM: Artificial Sequence
<220> FEATURE:
<223> OTHER INFORMATION: CH1 amino acid sequence of human IgG1

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95
Lys Val Glu Pro Lys Ser Cys Asp Lys
                100                 105
```

<210> SEQ ID NO 24
<211> LENGTH: 116
<212> TYPE: PRT
<213> ORGANISM: Artificial Sequence
<220> FEATURE:
<223> OTHER INFORMATION: Anti-GITR VHH amino acid sequence

<400> SEQUENCE: 24

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ala Phe Gly Ser Ser
                20                  25                  30

His Met Ser Trp Val Arg Ala Pro Gly Lys Gly Leu Glu Trp Val
            35                  40                  45

Ser Thr Ile His Ser Gly Gly Gly Phe Gly Asp Tyr Ala Asn Ser Val
        50                  55                  60

Gln Gly Arg Phe Thr Ile Ser Arg Asp Val Ala Lys Asn Thr Leu Tyr
65                  70                  75                  80

Leu Gln Met Asn Ser Leu Lys Pro Glu Asp Thr Ala Ile Tyr Tyr Cys
                85                  90                  95

Ala Leu Ala Thr Asp Trp Arg Lys Pro Pro Gly Gln Gly Thr Gln Val
                100                 105                 110

Thr Val Ser Ser
            115
```

<210> SEQ ID NO 25
<211> LENGTH: 7
<212> TYPE: PRT
<213> ORGANISM: Artificial Sequence
<220> FEATURE:
<223> OTHER INFORMATION: Anti-GITR VHH CDR1 amino acid sequence

<400> SEQUENCE: 25

```
Gly Phe Ala Phe Gly Ser Ser
1               5
```

<210> SEQ ID NO 26
<211> LENGTH: 7
<212> TYPE: PRT
<213> ORGANISM: Artificial Sequence
<220> FEATURE:
<223> OTHER INFORMATION: Anti-GITR VHH CDR2 amino acid sequence

<400> SEQUENCE: 26

```
Ser Gly Gly Gly Phe Gly Asp
1               5
```

<210> SEQ ID NO 27
<211> LENGTH: 7
<212> TYPE: PRT
<213> ORGANISM: Artificial Sequence
<220> FEATURE:
<223> OTHER INFORMATION: Anti-GITR VHH CDR3 amino acid sequence

<400> SEQUENCE: 27

```
Ala Thr Asp Trp Arg Lys Pro
```

<210> SEQ ID NO 28
<211> LENGTH: 571
<212> TYPE: PRT
<213> ORGANISM: Artificial Sequence
<220> FEATURE:
<223> OTHER INFORMATION: Amino acid sequence of the peptide chain #2 of the anti-VEGF/GITR bispecific antibody Bi-2-51

<400> SEQUENCE: 28

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Gln Val Gln Leu Gln Glu Ser Gly Gly Gly Leu Val
225                 230                 235                 240

Gln Pro Gly Gly Ser Leu Arg Leu Ser Cys Ala Ala Ser Gly Phe Ala
                245                 250                 255

Phe Gly Ser Ser His Met Ser Trp Val Arg Arg Ala Pro Gly Lys Gly
            260                 265                 270

Leu Glu Trp Val Ser Thr Ile His Ser Gly Gly Phe Gly Asp Tyr
        275                 280                 285

Ala Asn Ser Val Gln Gly Arg Phe Thr Ile Ser Arg Asp Val Ala Lys
    290                 295                 300

Asn Thr Leu Tyr Leu Gln Met Asn Ser Leu Lys Pro Glu Asp Thr Ala
305                 310                 315                 320

Ile Tyr Tyr Cys Ala Leu Ala Thr Asp Trp Arg Lys Pro Pro Gly Gln
                325                 330                 335

Gly Thr Gln Val Thr Val Ser Ser Asp Lys Thr His Thr Cys Pro Pro
            340                 345                 350
```

Cys Pro Ala Pro Glu Leu Leu Gly Gly Pro Ser Val Phe Leu Phe Pro
            355                 360                 365

Pro Lys Pro Lys Asp Thr Leu Met Ile Ser Arg Thr Pro Glu Val Thr
        370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
    450                 455                 460

Gly Gln Pro Arg Glu Pro Gln Val Tyr Thr Leu Pro Pro Ser Arg Asp
465                 470                 475                 480

Glu Leu Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 29
<211> LENGTH: 449
<212> TYPE: PRT
<213> ORGANISM: Artificial Sequence
<220> FEATURE:
<223> OTHER INFORMATION: Heavy chain (HC) amino acid sequence of IgG1

<400> SEQUENCE: 29

Glu Val Arg Leu Leu Glu Ser Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Thr Ser Arg Asp Asp Ser Lys Asn Ala Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Pro Gly Trp Tyr Ala Ala Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Ala Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 30
<211> LENGTH: 214
<212> TYPE: PRT
<213> ORGANISM: Artificial Sequence
<220> FEATURE:
<223> OTHER INFORMATION: Light chain (LC) amino acid sequence of IgG1

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

```
            50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asp Leu Pro Ala Phe
                 85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 343
<212> TYPE: PRT
<213> ORGANISM: Artificial Sequence
<220> FEATURE:
<223> OTHER INFORMATION: Heavy chain (HC) amino acid sequence of the
      anti-GITR antibody hcIgG-10

<400> SEQUENCE: 31

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Phe Ala Phe Gly Ser Ser
            20                  25                  30

His Met Ser Trp Val Arg Arg Ala Pro Gly Lys Gly Leu Glu Trp Val
        35                  40                  45

Ser Thr Ile His Ser Gly Gly Gly Phe Gly Asp Tyr Ala Asn Ser Val
    50                  55                  60

Gln Gly Arg Phe Thr Ile Ser Arg Asp Val Ala Lys Asn Thr Leu Tyr
 65                  70                  75                  80

Leu Gln Met Asn Ser Leu Lys Pro Glu Asp Thr Ala Ile Tyr Tyr Cys
                 85                  90                  95

Ala Leu Ala Thr Asp Trp Arg Lys Pro Pro Gly Gln Gly Thr Gln Val
            100                 105                 110

Thr Val Ser Ser Asp Lys Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190
```

```
Asn Ser Thr Tyr Arg Val Val Ser Val Leu Thr Val Leu His Gln Asp
        195                 200                 205
Trp Leu Asn Gly Lys Glu Tyr Lys Cys Lys Val Ser Asn Lys Ala Leu
    210                 215                 220
Pro Ala Pro Ile Glu Lys Thr Ile Ser Lys Ala Lys Gly Gln Pro Arg
225                 230                 235                 240
Glu Pro Gln Val Tyr Thr Leu Pro Pro Ser Arg Asp Glu Leu Thr Lys
                245                 250                 255
Asn Gln Val Ser Leu Thr Cys Leu Val Lys Gly Phe Tyr Pro Ser Asp
            260                 265                 270
Ile Ala Val Glu Trp Glu Ser Asn Gly Gln Pro Glu Asn Asn Tyr Lys
        275                 280                 285
Thr Thr Pro Pro Val Leu Asp Ser Asp Gly Ser Phe Phe Leu Tyr Ser
    290                 295                 300
Lys Leu Thr Val Asp Lys Ser Arg Trp Gln Gln Gly Asn Val Phe Ser
305                 310                 315                 320
Cys Ser Val Met His Glu Ala Leu His Asn His Tyr Thr Gln Lys Ser
                325                 330                 335
Leu Ser Leu Ser Pro Gly Lys
            340

<210> SEQ ID NO 32
<211> LENGTH: 4
<212> TYPE: PRT
<213> ORGANISM: Artificial Sequence
<220> FEATURE:
<223> OTHER INFORMATION: Synthetic

<400> SEQUENCE: 32

Cys Pro Pro Cys
1
```